United States Patent [19]

Axen

[11] 4,125,712
[45] Nov. 14, 1978

[54] CERTAIN 5,6-DIHYDRO-PROSTACYCLIN ANALOGS

[75] Inventor: Udo F. Axen, Plainwell, Mich.

[73] Assignee: The Upjohn Company, Kalamazoo, Mich.

[21] Appl. No.: 857,236

[22] Filed: Dec. 5, 1977

Related U.S. Application Data

[63] Continuation-in-part of Ser. No. 788,146, Apr. 19, 1977, abandoned, which is a continuation-in-part of Ser. No. 691,400, Jun. 1, 1976, abandoned.

[51] Int. Cl.$^2$ ............................................. C07D 307/93
[52] U.S. Cl. ..................................... 542/421; 542/420; 542/422; 542/426; 542/429; 260/308 D; 260/346.22; 260/346.73
[58] Field of Search ......... 260/308 D, 346.22, 346.73; 542/420, 421, 422, 426, 429

[56] References Cited
PUBLICATIONS

Johnson, et al., J. Am. Chem. Soc. 99, 4182, (1977).

Primary Examiner—Henry R. Jiles
Assistant Examiner—Bernard Dentz
Attorney, Agent, or Firm—Morris L. Nielsen

[57] ABSTRACT

Processes for preparing 5,6-dihydro-prostacyclin analogs, which are 9-deoxy-6,9-cyclic ethers of prostaglandin $F_{1\alpha}$-type compounds, illustrated for example, by a compound of the formula

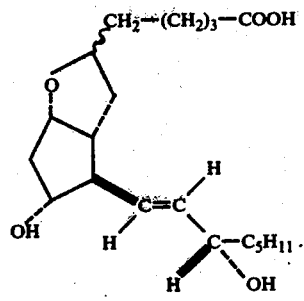

wherein ~ indicates alpha or beta configuration; including the products and intermediates produced therein, said products having pharmacological utility.

There are also provided mercury derivatives of these 5,6-dihydro-prostacyclins, illustrated, for example, by a compound of the formula

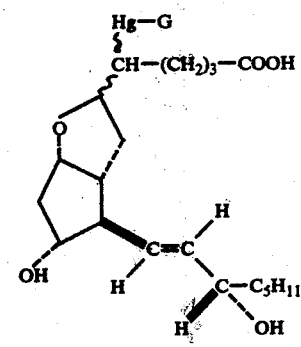

wherein G is nitrato, iodo, chloro, bromo, acetato, trifluoroacetato, or benzoato, and wherein ~ indicates alpha or beta configuration, said products having pharmacological activity, and useful as intermediates in preparing the above compounds.

116 Claims, No Drawings

CERTAIN 5,6-DIHYDRO-PROSTACYCLIN ANALOGS

CROSS REFERENCE TO RELATED APPLICATIONS

This application is a continuation-in-part of copending application Ser. No. 788,146 filed Apr. 19, 1977, now abandoned, which was a continuation-in-part of then copending application Ser. No. 691,400 filed June 1, 1976, now abandoned.

BACKGROUND OF THE INVENTION

This invention relates to products having prostacyclin-like structure and to processes for preparing them. In particular this invention relates to 5,6-dihydro-prostacyclin analogs and to processes for preparing them.

Prostacyclin is an organic compound related to prostaglandins, identified as (5Z)-9-deoxy-6,9α-epoxy-$\Delta^5$-PGF$_1$, and represented by the formula:

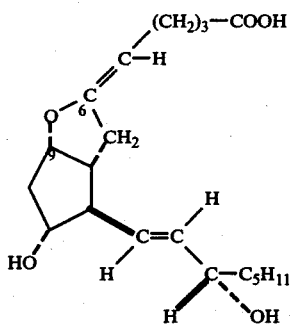

See R. A. Johnson et al., Prostaglandins 12, 915 (1976) and J. Am. Chem. Soc. 99, 4182 (1977).

The prostaglandins and analogs are well-known organic compounds derived from prostanoic acid which has the following structure and atom numbering:

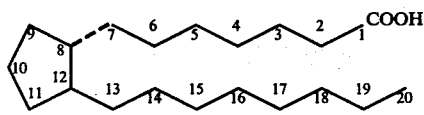

As drawn hereinafter the formulas represent a particular optically active isomer having the same absolute configuration as PGF$_{1\alpha}$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

Somewhat related compounds have been reported by C. Pace-Asciak et al., in Biochemistry, Vol. 10, pages 3657-3664 (1971), including, for example:

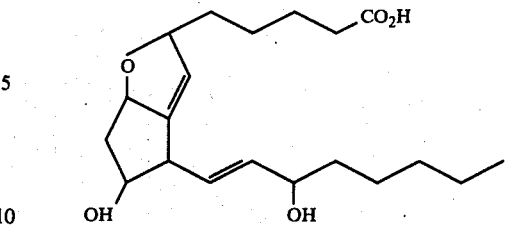

Prostacyclin and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undesirable gastrointestinal effects from systemic administration of prostaglandin synthetase inhibitors.

Because of these biological responses, prostacyclin and prostacyclin-type compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart-lung machines. Additionally whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the recipient, or to two or all of those at a total steady state dose of about 0.001-1.0 μg./ml. of whole blood. These compounds are also useful in preparing platelet-rich concentrates from blood for use in treating thrombocytopenia or in chemotherapy.

Prostacyclin and prostacyclin-type compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostacyclin and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Prostacyclin and prostacyclin-type compounds are also useful in reducing the undesirable gastrointestinal effects resulting from systemic administration of anti-inflammatory prostaglandin synthetase inhibitors, and are used for that purpose by concomitant administration of the prostacyclin or prostacyclin-type compound and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds, Prostacyclin and prostacyclin-type compounds are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostacyclin or prostacyclin-type compound is administered along with the anti-inflammatory prostaglandin synthetase inhibitor either by the same route of administration or by a different route. For example, if the anti-inflammatory substance is being administered orally, the prostacyclin or prostacyclin-type compound is also administered orally, or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostacyclin or prostacyclin-type compound is also administered rectally. Further, the prostacyclin derivative can be conveniently administered orally or, in the case of women, vaginally. It is especially convenient when the administration route is to be the same for both anti-inflammatory substance and prostacyclin or prostacyclin-type compound to combine both into a single dosage form.

The dosage regimen for the prostacyclin or prostacyclin-type compound in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular prostacyclin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostacyclin or prostacyclin-type compound to reduce and then substantially to eliminate those undesirable effects.

Prostacyclin or prostacyclin-type compounds are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the prostacyclin or prostacyclin-type compound can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

Prostacyclin or prostacyclin-type compounds are effectively administered to human asthma patients by oral inhalation or by aerosol inhalation.

For administration by the oral inhalation route with conventional nebulizers or by oxygen aerosolization it is convenient to provide the prostacyclin ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

Prostacyclin or prostacyclin-type compounds are useful in mammals, including man, as nasal decongestants and are used for this purpose in a dose range of about 10 $\mu$g. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, nonobstructive mesenteric ischemia, arteritis lymphangitis and the like. These examples are included to be illustrative and should not be construed as limiting the term peripheral vascular disease. For these conditions the prostacyclin compounds are administered orally or parenterally via injection or infusion directly into a vein or artery.

The dosages of these compounds are in the range of 0.01-1.0 $\mu$g. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Patent No. 74/0149 referenced as Derwent Farmdoc No. 58,400V. See Elliott, et al., Lancet, January 18, 1975, pp. 140–142.

Prostacyclin or prostacyclin-type compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

Prostacyclin or prostacyclin-type compounds are further useful for controlling the reproductive cycle in menstruating female mammals, including humans. By the term menstruating female mammals is meant animals which are mature enough to menstruate, but not so old that regular menstruation has ceased. For that purpose the prostacyclin compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostacyclin or prostacyclin-type compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostacyclin compounds is also useful in operative gynecology such as D and C (Cervical Dilation and Uterine Curettage) where mechanical dilation may cause perforation of the uterus, cervical tears, or infections. It is also useful for diagnostic procedures where dilation is necessary for tissue examination. For these purposes, the prostacyclin compound is administered locally or systemically.

The prostacyclin compound, for example, is administered orally or vaginally at doses of about 5 to 50 mg. per treatment of an adult female human, with from one to five treatments per 24 hour period. Alternatively the compound is administered intramuscularly or subcutaneously at doses of about 1 to 25 mg. per treatment. The exact dosages for these purposes depend on the age, weight, and condition of the patient or animal.

Prostacyclin and prostacyclin-type compounds are further useful in domestic animals as in abortifacients (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostacyclin compound is injected or applied in a feed at doses of 0.1-100 mg. per animal and may be combined with other agents such as steroids. Dosing schedules will depend on the species treated. For example, mares are given the prostacyclin compound 5 to 8 days after ovulation and return to estrus. Cattle are treated at regular intervals over a 3 week period to advantageously bring all into estrus at the same time.

Prostacyclin or prostacyclin-type compounds increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

These prostacyclin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, nonmalignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared.

For those purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostacyclin or prostacyclin-type compounds are useful as antiflammatory agents for inhibiting chronic inflammation in mammals including the swelling and other unpleasant effects thereof using methods of treatment and dosages generally in accord with U.S. Pat. No. 3,885,041, which patent is incorporated herein by reference.

SUMMARY OF THE INVENTION

It is the purpose of this invention to provide novel products having pharmacological activity. It is a further purpose to provide processes for preparing these products and their intermediates.

The presently provided cyclic ethers include compounds of the following formulas:

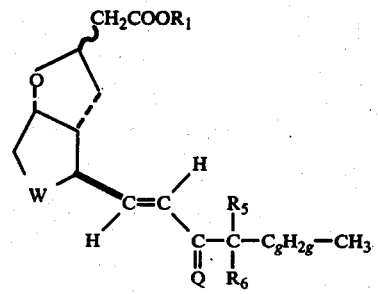

III

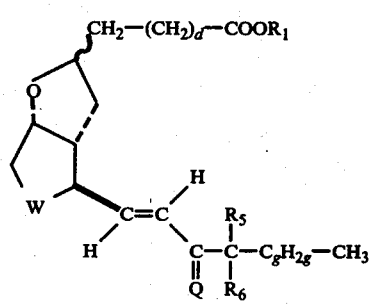

IV

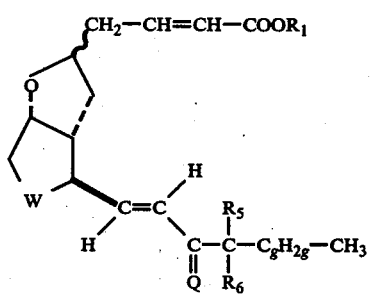

V

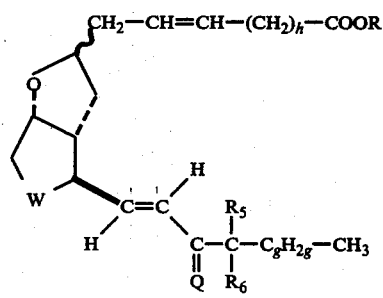

VI

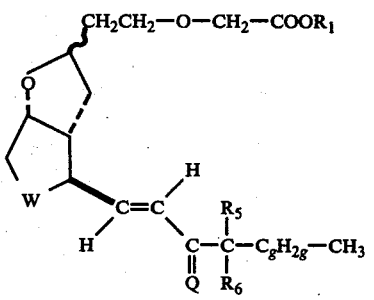

VII

-continued

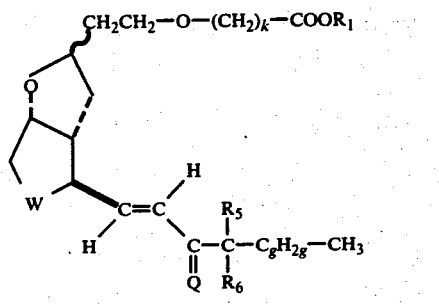  VIII

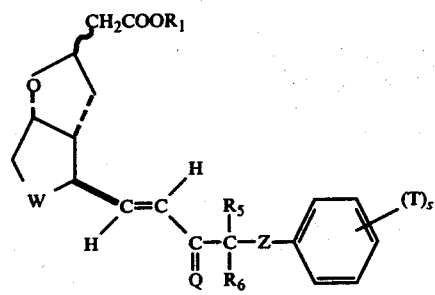  IX

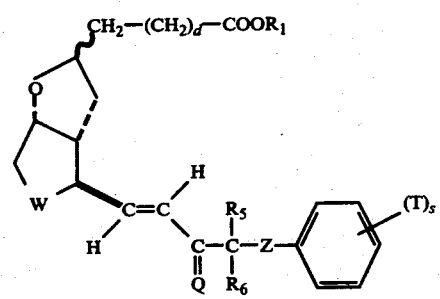  X

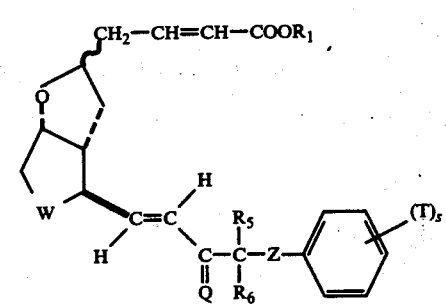  XI

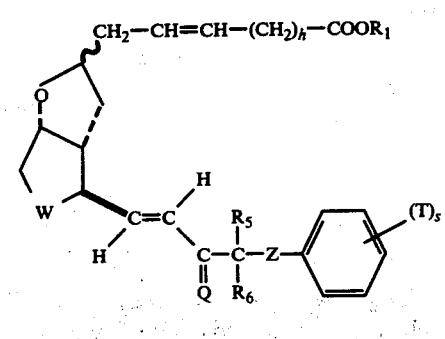  XII

-continued

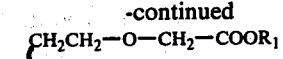  XIII

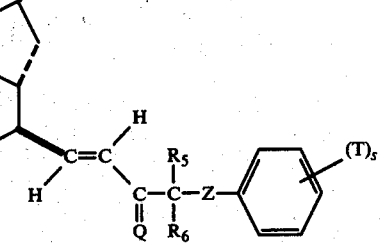

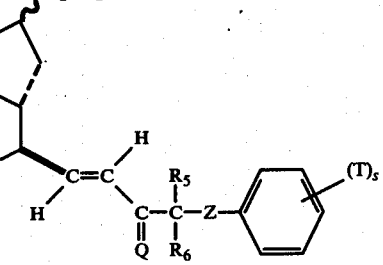  XIV

There are also provided cyclic ethers of the following formulas:

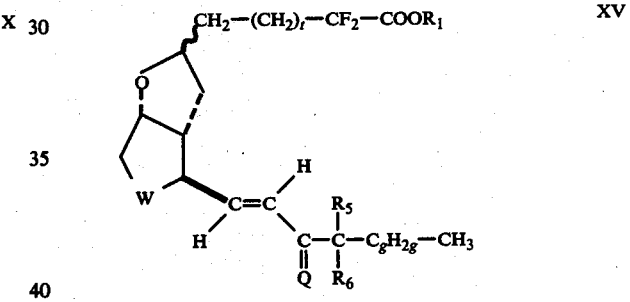  XV

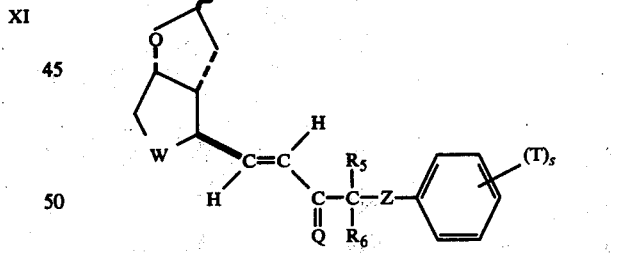  XVI

In formulas III–XIV, and in other formulas hereafter, including formulas in the Charts, the terms "$d$", "$h$", "$k$", and the like are as defined in the TABLE included herein. Reference to that Table will establish what is intended to be represented by each formula.

TABLE
Definition of Terms for Formulas

A is
a valence bond or —$(CH_2)_h$— where $h$ is 1, 2, or 3.

D is
(1) a valence bond; (2) —$(CH_2)_d$— where $d$ is 1, 2, 3, 4, or 5; (3) —CH=CH—A— where A is a valence bond or —$(CH_2)_h$— where $h$ is 1, 2, or 3; or (4) —CH- $_2$—O—CH$_2$—Y— where Y is a valence bond or —(CH$_2$)$_k$— where $k$ is 1 or 2.

D' is
—CH$_2$—CH=CH—A— or —(CH$_2$)$_t$—CF$_2$— wherein A is a valence bond or —(CH$_2$)$_h$— where $h$ is 1, 2, or 3; and wherein $t$ is 2, 3, or 4.

E is
alkyl of 1 to 4 carbon atoms, inclusive, phenyl, phenyl substituted with 1 to 2 fluoro, chloro, or alkyl of 1 to 4 carbon atoms, inclusive, or aralkyl of 7 to 12 carbon atoms, inclusive.

G is
nitrato, iodo, chloro, bromo, acetato, trifluoroacetato, or benzoato.

L is
(1) a valence bond, (2) —(CH$_2$)$_d$— wherein $d$ is 1 to 5 inclusive, (3) —(CH$_2$)$_t$—CF$_2$— wherein $t$ is 2, 3, or 4, (4) —CH$_2$—CH=CH—A— wherein A is a valence bond or —(CH$_2$)$_h$— wherein $h$ is 1, 2, or 3, or (5) —CH$_2$—O—CH$_2$—Y— wherein Y is a valence bond or —(CH$_2$)$_k$— wherein $k$ is 1 or 2.

L$_1$ is

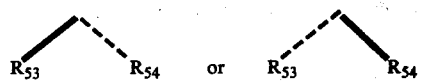 or 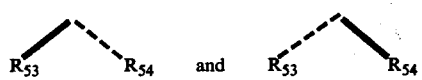

or a mixture of

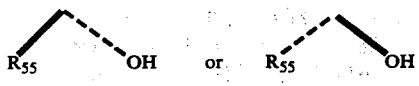 and 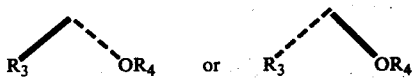

wherein R$_{53}$ and R$_{54}$ are hydrogen, methyl, or fluoro, being the same or different, with the proviso that one of R$_{53}$ and R$_{54}$ is fluoro only when the other is hydrogen or fluoro.

L$_2$ and L$_3$ are
hydrogen, alkyl of one to 4 carbon atoms, inclusive, or —COOR$_{51}$, wherein R$_{51}$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted 1, 2, or 3 chloro or alkyl of 1 to 3 carbon atoms, inclusive; being the same or different, with the proviso that not more than one of L$_2$ and L$_3$ is —COOR$_{51}$.

M is
—(CH$_2$)$_h$ wherein $h$ is 1, 2, or 3.

M$_1$ is

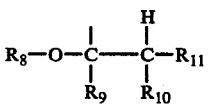

wherein R$_{55}$ is hydrogen or methyl.

Q is

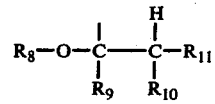

wherein R$_3$ is hydrogen or alkyl of 1 to 4 carbon atoms, inclusive, and wherein R$_4$ is hydrogen, tetrahydropyran-2-yl, tetrahydrofuranyl, 1-ethoxyethyl or a group of the formula

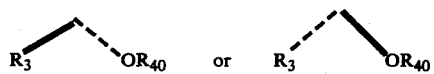

wherein R$_8$ is alkyl of 1 to 18 carbon atoms, inclusive, cycloalkyl of 3 to 10 carbon atoms, inclusive, aralkyl of 7 to 12 carbon atoms, inclusive, phenyl, or phenyl substituted with 1, 2, or 3 alkyl of 1 to 4 carbon atoms, inclusive, wherein R$_9$ and R$_{10}$ are the same or different, being hydrogen, alkyl of 1 to 4 carbon atoms, inclusive, phenyl or phenyl substituted with 1, 2, or 3 alkyl of 1 to 4 carbon atoms, inclusive, or, when R$_9$ and R$_{10}$ are taken together, —(CH$_2$)$_a$— or —(CH$_2$)$_b$—O—(CH$_2$)$_c$— wherein $a$ is 3, 4, or 5, $b$ is 1, 2, or 3, and $c$ is 1, 2, or 3 with the proviso that $b$ plus $c$ is 2, 3, or 4, and wherein R$_{11}$ is hydrogen or phenyl.

Q$_1$ is

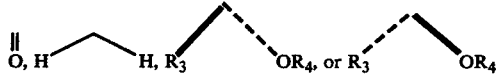

wherein R$_3$ is as defined above, and wherein R$_{40}$ is the same as R$_4$ defined above except that it does not include hydrogen, but includes only the blocking groups such as tetrahydropyran-2-yl.

Q$_2$ is

wherein R$_3$ and R$_4$ are as defined above for Q.

Q$_3$ is

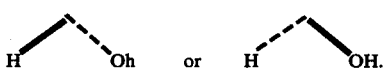

wherein R$_3$ is hydrogen or alkyl of 1 to 4 carbon atoms, inclusive.

Q$_4$ is

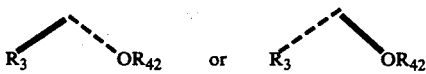

Q$_5$ is

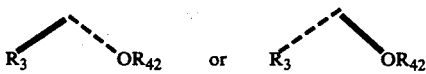

wherein R$_{42}$ is (1) tetrahydropyran-2-yl, (2) tetrahydrofuranyl, (3) 1-ethoxyethyl, (4) a group of the formula

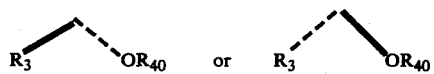

wherein R$_8$ is alkyl of 1 to 18 carbon atoms, inclusive, cycloalkyl of 3 to 10 carbon atoms, inclusive, phenyl, or phenyl substituted with one, 2, or 3 alkyl of one to 4 carbon atoms, inclusive, wherein R$_9$ and R$_{10}$ are the same or different, being hydrogen, alkyl of 1 to 4 carbon atoms, inclusive, phenyl or phenyl substituted with 1, 2, or 3 alkyl of 1 to 4 carbon atoms, inclusive, or, when $R_9$ and $R_{10}$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4, and wherein $R_{11}$ is hydrogen or phenyl, or (5) a silyl group of the formula $-Si(E)_3$ wherein E is alkyl of 1 to 4 carbon atoms, inclusive, phenyl, phenyl substituted with 1 or 2 fluoro, chloro, or alkyl of 1 to 4 carbon atoms, inclusive, or aralkyl of 7 to 12 carbon atoms, inclusive.

$Q_6$ is

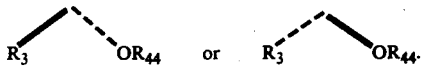

wherein $R_{44}$ is $R_{42}$ as defined for $Q_5$ and hydrogen.

$R_1$ is
 hydrogen or alkyl of 1 to 8 carbon atoms, inclusive, or a pharmacologically acceptable cation.

$R_2$ is

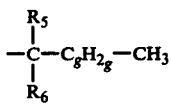 (1)

wherein $C_gH_{2g}$ is alkylene of 1 to 9 carbon atoms, inclusive, with 1 to 5 carbon atoms, inclusive, in the chain between $-CR_5R_6-$ and terminal methyl, wherein $R_5$ and $R_6$ are hydrogen, alkyl of 1 to 4 carbon atoms, inclusive, or fluoro, being the same or different, with the proviso that one of $R_5$ and $R_6$ is fluoro only when the other is hydrogen or fluoro; or

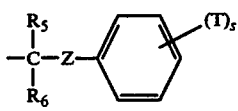 (2)

wherein $R_5$ and $R_6$ are as defined above with the proviso that neither $R_5$ nor $R_6$ is fluoro when Z is oxa $(-O-)$; wherein Z represents an oxa atom $(-O-)$ or $C_jH_{2j}$ wherein $C_jH_{2j}$ is a valence bond or alkylene of 1 to 9 carbon atoms, inclusive, with 1 to 6 carbon atoms, inclusive between $-CR_5R_6-$ and the phenyl ring; wherein T is alkyl of 1 to 4 carbon atoms, inclusive, fluoro, chloro, trifluoromethyl, or $-OR_7-$ wherein $R_7$ is alkyl of 1 to 4 carbon atoms, inclusive, and $s$ is 0, 1, 2, or 3, with the proviso that not more than two T's are other than alkyl and when $s$ is 2 or 3 the T's are either the same or different.

$R_3$ is
 hydrogen or alkyl of 1 to 4 carbon atoms.

$R_4$ is
 hydrogen, tetrahydropyran-2-yl, tetrahydrofuranyl, 1-ethoxyethyl or a group of the formula

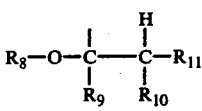

wherein $R_8$ is alkyl of 1 to 18 carbon atoms, inclusive, cycloalkyl of 3 to 10 carbon atoms, inclusive, aralkyl of 7 to 12 carbon atoms, inclusive, phenyl, or phenyl substituted with 1, 2, or 3 alkyl of 1 to 4 carbon atoms, inclusive, wherein $R_9$ and $R_{10}$ are the same or different, being hydrogen, alkyl of 1 to 4 carbon atoms, inclusive, phenyl or phenyl substituted with 1, 2, or 3 alkyl of 1 to 4 carbon atoms, inclusive, or when $R_9$ and $R_{10}$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4, and wherein $R_{11}$ is hydrogen or phenyl.

$R_5$ and $R_6$ are
 hydrogen, alkyl of 1 to 4 carbon atoms, inclusive, or fluoro, being the same or different, with the proviso that one of $R_5$ and $R_6$ is fluoro only when the other is hydrogen or fluoro, and with the further proviso that, when Z is oxa $(-O-)$ as defined below, neither $R_5$ nor $R_6$ is fluoro.

$R_7$ is
 alkyl of 1 to 4 carbon atoms, inclusive.

$R_8$ is
 alkyl of 1 to 18 carbon atoms, inclusive, cycloalkyl of 3 to 10 carbon atoms, inclusive, aralkyl of 7 to 12 carbon atoms, inclusive, phenyl, or phenyl substituted with 1, 2, or 3 alkyl of 1 to 4 carbon atoms, inclusive.

$R_9$ and $R_{10}$ are
 the same or different, being hydrogen, alkyl of 1 to 4 carbon atoms, inclusive, phenyl or phenyl substituted with 1, 2, or 3 alkyl of 1 to 4 carbon atoms, inclusive, or, when $R_9$ and $R_{10}$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4.

$R_{11}$ is
 hydrogen or phenyl.

$R_{12}$ is
 alkyl of 1 to 8 carbon atoms, inclusive.

$R_{13}$ is
 the group $-\overset{+}{P}(C_6H_5)_3$ or $-P(O)(OR_{12})_2$ wherein $R_{12}$ is as defined above.

$R_{14}$ is
 hydrogen or an alkali metal cation.

$R_{15}$ is
 alkyl of 1 to 3 carbon atoms, inclusive.

$R_{16}$ is
 (1) $-COOR_{17}$
 (2) $-CH_2OH$
 (3) $-CH_2N(R_{18})_2$

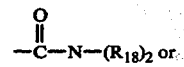 (4)

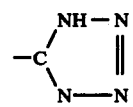 (5)

wherein $R_{17}$ is (a) hydrogen, (b) alkyl of 1 to 12 carbon atoms, inclusive, (c) cycloalkyl of 3 to 10 carbon atoms, inclusive, (d) aralkyl of 7 to 12 carbon atoms, inclusive, (e) phenyl, (f) phenyl with 1, 2, or 3 chloro or alkyl of 1 to 4 carbon atoms, inclusive, or (g) 2-naphthyl; and wherein $R_{18}$ is hydrogen, alkyl of 1 to 12 carbon atoms, inclusive, benzyl, or phenyl, being the same or different.

$R_{17}$ is
 as defined in $R_{16}$ above.

$R_{18}$ is
as defined in $R_{16}$ above.

$R_{19}$ is
(a) alkyl of 1 to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with 1, 2, or 3 chloro or alkyl of 1 to 4 carbon atoms, inclusive, (f) 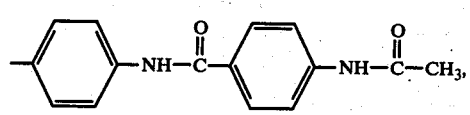

(g) 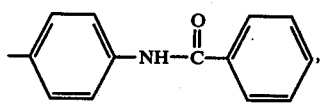

(h) 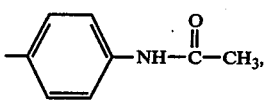

(i) 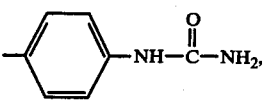

(j) 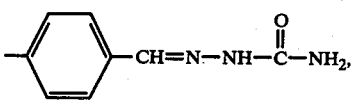

(k) 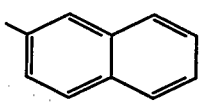

(l) 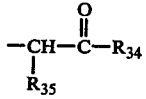

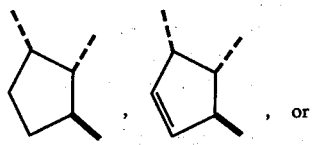

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl,
(m) hydrogen; or
(n) a pharmacologically acceptable cation.

$R_{20}$ is

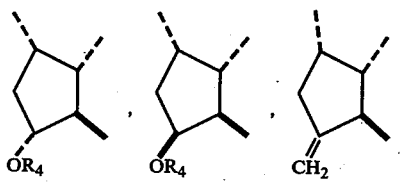

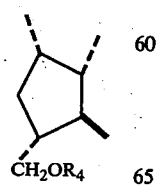

wherein $R_4$ is as defined above.

$R_{21}$ is
the same as $R_{20}$ defined above except that $R_4$ therein is replaced with $R_{40}$ as defined below, i.e. excluding hydrogen.

$R_{22}$ is

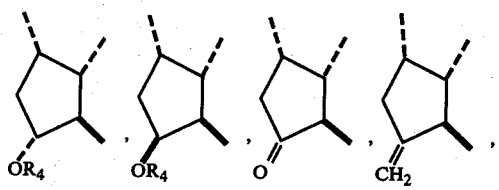

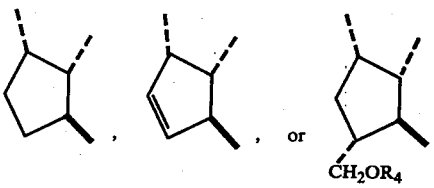

wherein $R_4$ is as defined above.

$R_{25}$ includes
$R_2$, as defined above, and

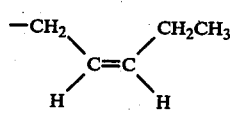

$R_{23}$ is

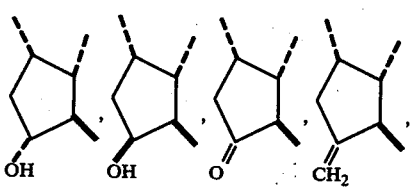

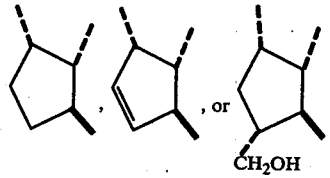

$R_{24}$ is

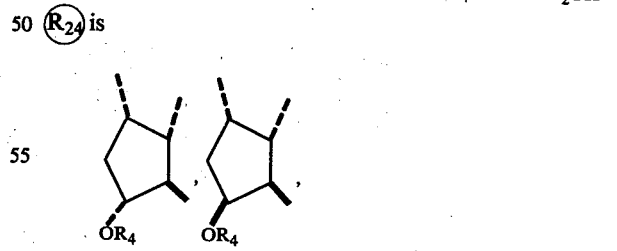

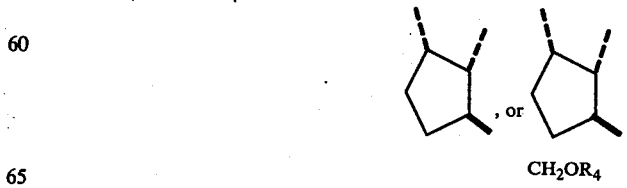

$R_{26}$ is
a carboxyacyl blocking group:

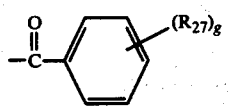 (1)

wherein $R_{27}$ is alkyl of 1 to 4 carbon atoms, inclusive, phenylalkyl of 7 to 10 carbon atoms, inclusive, phenyl or nitro, and g is 0 to 5, inclusive, provided that not more than two $R_{27}$'s are other than alkyl, and that the total number of carbon atoms in the $R_{27}$'s does not exceed 10 carbon atoms:

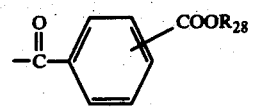 (2)

wherein $R_{28}$ is alkyl of 1 to 4 carbon atoms, inclusive; or

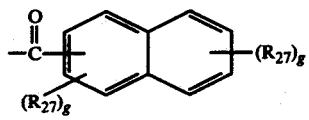 (3)

wherein $R_{27}$ and g are as defined above.
$R_{27}$ is
as defined in $R_{26}$ above.
$R_{28}$ is
as defined in $R_{26}$ above.
$R_{30}$ is
(1) —COOR$_{19}$
(2) —CH$_2$OH
(3) —CH$_2$N(R$_{18}$)$_2$,

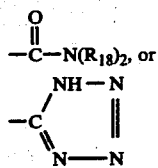

wherein $R_{19}$ is
(a) alkyl of 1 to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with 1, 2, or 3 chloro or alkyl of 1 to 4 carbon atoms, inclusive,

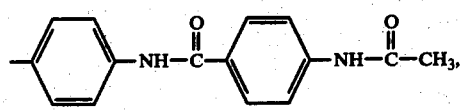 (f)

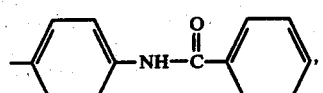 (g)

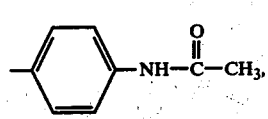 (h)

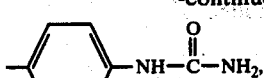 (i)

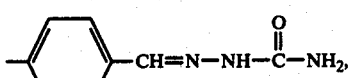 (j)

 (k)

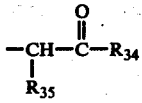 (l)

wherein $R_{34}$ is phenyl, p-bromophenyl, p-bi-phenylyl, p-nitrophenyl, p-benzamidophenyl, or 2-naphthyl, and wherein $R_{35}$ is hydrogen or benzoyl,
(m) hydrogen; or
(n) a pharmacologically acceptable cation; and wherein $R_{18}$ is hydrogen, alkyl of one to 12 carbon atoms, inclusive, benzyl, or phenyl, being the same or different.
$R_{31}$ is
(1) —COOR$_{32}$
(2) —CH$_2$OH, with the proviso that $R_{31}$ is not —CH$_2$OH when D is a valence bond,
(3) —CH$_2$N(R$_{18}$)$_2$,

wherein $R_{32}$ is
(a) cycloalkyl of 3 to 10 carbon atoms, inclusive,
(b) aralkyl of 7 to 12 carbon atoms, inclusive,
(c) phenyl,
(d) phenyl substituted with 1, 2, or 3 chloro or alkyl of 1 to 4 carbon atoms, inclusive,

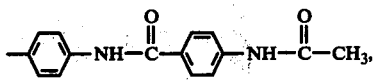 (e)

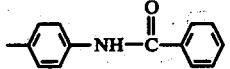 (f)

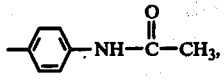 (g)

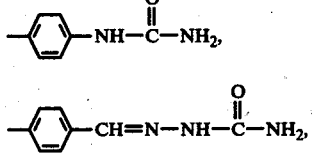

-continued

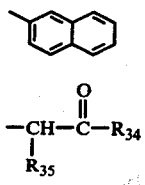, or

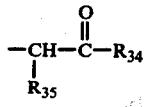

wherein $R_{34}$ is phenyl, p-bromophenyl, p-bi-phenylyl, p-nitrophenyl, p-benzamidophenyl, or 2-naphthyl,
wherein $R_{35}$ is hydrogen or benzoyl, and
wherein $R_{18}$ is hydrogen, alkyl of one to 12 carbon atoms, inclusive, benzyl, or phenyl, being the same or different; wherein ~ indicates attachment in alpha or beta configuration; including
the lower alkanoates thereof.

$R_{32}$ is
  as defined in $R_{31}$ above.
$R_{33}$ is
  iodo or bromo.
$R_{34}$ is
  phenyl, p-bromophenyl, p-biphenylyl, p-nitrophenyl, p-benzamidophenyl, or 2-naphthyl.
$R_{35}$ is
  hydrogen or benzoyl.
$R_{36}$ is
  (1) —COOR$_{37}$
  (2) —CH$_2$OH
  (3) —CH$_2$N(R$_{18}$)$_2$

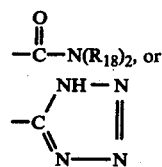

wherein $R_{37}$ is
  (a) alkyl of 1 to 12 carbon atoms, inclusive,
  (b) cycloalkyl of 3 to 10 carbon atoms, inclusive,
  (c) aralkyl of 7 to 12 carbon atoms, inclusive,
  (d) phenyl,
  (e) phenyl substituted with 1, 2, or 3 chloro or alkyl of 1 to 4 carbon atoms, inclusive,

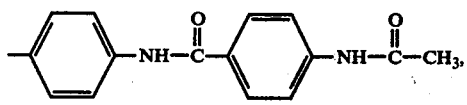

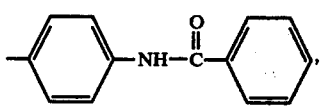

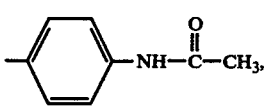

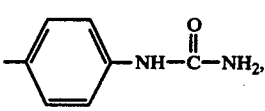

-continued

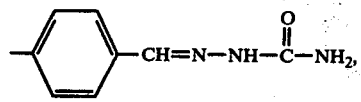

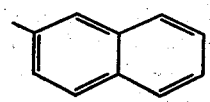

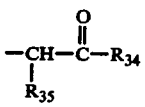

wherein $R_{34}$ is phenyl, p-bromophenyl, p-bi-phenylyl, p-nitrophenyl, p-benzamidophenyl, or 2-naphthyl, and wherein $R_{33}$ is hydrogen or benzoyl, or
(m) hydrogen; and wherein $R_{18}$ is hydrogen, alkyl of one to 12 carbon atoms, inclusive, benzyl, or phenyl, being the same or different.

$R_{37}$ is
  as defined above in $R_{36}$.
$R_{38}$ is
  bromo or chloro.
$R_{40}$ is
  the same as $R_4$ defined above except that it does not include hydrogen, but only the blocking groups such as tetrahydropyran-2-yl.
$(R_{41})$ is

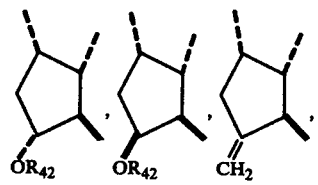

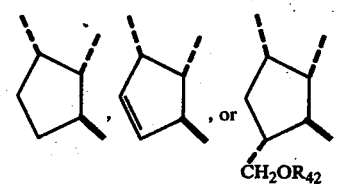

wherein $R_{42}$ includes $R_{40}$ blocking groups as defined above, together with silyl groups of the formula- Si(E)$_3$ wherein E is alkyl of 1 to 4 carbon atoms, inclusive, phenyl, phenyl substituted with one or 2 fluoro, chloro, or alkyl of 1 to 4 carbon atoms, inclusive, or aralkyl of 7 to 12 carbon atoms, inclusive.

$R_{42}$ is
  as defined in $(R_{41})$. $(R_{43})$

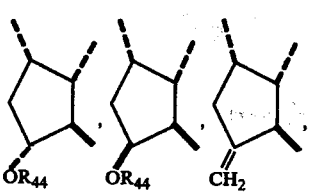

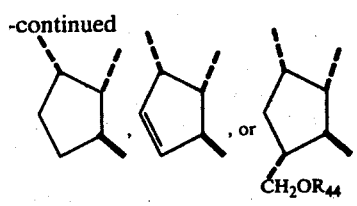

wherein $R_{44}$ includes $R_{42}$ blocking groups and hydrogen.

$R_{44}$ is
is as defined in $R_{43}$.

$R_{51}$ is
hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted 1, 2, and 3 chloro or alkyl of one to 3 carbon atoms, inclusive.

$R_{53}$ and $R_{54}$ are
hydrogen, methyl, or fluoro, being the same or different, with the proviso that one of $R_{53}$ and $R_{54}$ is fluoro only when the other is hydrogen or fluoro.

$R_{55}$ is
hydrogen or methyl.

$R_{57}$ is
(1) $-(CH_2)_m-CH_3-$,

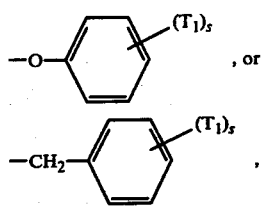

wherein m is 1 to 5, inclusive, $T_1$ is chloro, fluoro, trifluoromethyl, alkyl of 1 to 3 carbon atoms, inclusive, or alkoxy of 1 to 3 carbon atoms, inclusive, and s is 0, 1, 2, or 3, the various $T_1$'s being the same or different, with the proviso that not more than two $T_1$'s are other than alkyl.

$R_{58}$ is
hydrogen or hydroxy.

T is
alkyl of one to 4 carbon atoms, inclusive, fluoro, chloro, trifluoromethyl or $-OR_7-$ wherein $R_7$ is hydrogen or alkyl of one to 4 carbon atoms, inclusive, and s is 0, 1, 2, or 3, with the proviso that not more than two T's are other than alkyl and when s is 2 or 3 the T's are either the same or different.

$T_1$ is
chloro, fluoro, trifluoromethyl, alkyl of 1 to 3 carbon atoms, inclusive, or alkoxy of 1 to 3 carbon atoms, inclusive, and s is 0, 1, 2, or 3, the various $T_1$'s being the same or different, with the proviso that not more than two $T_1$'s are other than alkyl.

W is

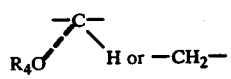

wherein $R_4$ is as defined above.

X is
trans—CH=CH—, cis—CH=CH—, —C≡C—, or —CH$_2$CH$_2$—.

X' is
cis—CH=CH—, —C≡C—, or —CH$_2$CH$_2$—.

Y is
a valence bond or —(CH$_2$)$_k$— where k is 1 or 2.

$Y_1$ is
trans—CH=CH—; —C≡C— or —CH$_2$CH$_2$—.

Z is
an oxa atom (-O-) or $C_jH_{2j}$ is a valence bond or alkylene of one to 9 carbon atoms, inclusive, substituted with 0, 1, or 2 fluoro, with 1 to 6 carbon atoms, inclusive between —CR$_5$R$_6$— and the phenyl ring.

$Z_1$ is
(1) cis—CH=CH—CH$_2$—(CH$_2$)$_g$—CH$_2$—, or
(2) cis—CH=CH—CH$_2$—(CH$_2$)$_g$—CF$_2$—, wherein g is 1, 2, or 3.

a is
3, 4, or 5.

b is
1, 2, or 3.

c is
1, 2, or 3 with the proviso that b plus c is 2, 3, or 4.

d is
an integer of 1 to 5, inclusive.

g (as to (R$_{27}$)$_g$ in carboxyacyl groups) is
0 to 5, inclusive, g (as to —(CH$_2$)$_g$— in $Z_1$ of Preparation 1) is
1, 2, or 3.

h is
1, 2, or 3.

k is
1 or 2.

m is
1 to 5, inclusive.

s is
0, 1, 2, or 3.

t is
2, 3, or 4.

Hal is
chloro, bromo, or iodo.

THP is
tetrahydropyran-2-yl.

Ts is
p-toluenesulfonyl.

The symbol ~ (wavy line) indicates
attachment in alpha or beta configuration.

$C_gH_{2g}$ is
alkylene of one to 9 carbon atoms, inclusive, with one to 5 carbon atoms, inclusive, in the chain between —CR$_5$R$_6$— and terminal methyl.

$C_jH_{2j}$ is
a valence bond or alkylene of 1 to 9 carbon atoms, inclusive, substituted with 0, 1, or 2 fluoro, with 1 to 6 carbon atoms, inclusive between —CR$_5$R$_6$— and the phenyl ring.

The carbon atoms are numbered as for prostanoic acid (1), except that the carbon atoms in longer or shorter side chains are named, following the usual convention, as "nor" or "homo" atoms. Thus, in compound V above, the —CH=CH— group is at the "3,4" position and C-2 is a "nor" atom.

By way of illustration, formula III represents 9-deoxy-6ξ,9α epoxy-2,3,4-trinor-PGF$_1$, ethyl ester, when $C_gH_{2g}$ is trimethylene, Q is

$R_1$ is ethyl, $R_5$ and $R_6$ are hydrogen, and W is

Formula XI represents 9-deoxy-3,4-trans-didehydro-6ξ,9α-epoxy-17-phenyl-2,18,19,20-tetranor-PGF$_1$, methyl ester when Q is

$R_1$ is methyl, $R_5$ and $R_6$ are hydrogen, s is zero, W is

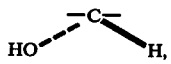

and Z is methylene. When W is —CH$_2$—, the compounds are named as derivatives of 11-deoxy-PGF$_1$.

For those compounds of formula III–XVI wherein Q is

i.e. wherein the C-15 hydroxyl or ether group is attached to the side chain in alpha configuration, the configuration at C-15 is identical with that of the naturally occuring prostaglandins such as PGE$_1$ obtained from mammalian tissues. The 15-epimer compounds are represented by formulas III–XVI when Q is

and are identified variously as "15-epi" or "15β" by the appropriate prefix in the name. As is known in the art, "R" and "S" designations depend on the neighboring substituents. See R. S. Cahn, J. Chem. Ed. 41, 116 (1964).

Included among the compounds disclosed herein are 9-deoxy-6,9-epoxy compounds corresponding to the compounds of formula III–XVI having, at $C_{17}$ and $C_{18}$, cis—CH=CH—, as illustrated by the formula:

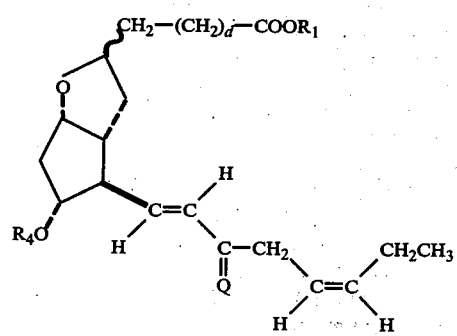

XVII

Also included are 9-deoxy-6,9-epoxy compounds corresponding to those of formula III–XVII except that "W" in the cyclopentane ring is replaced with

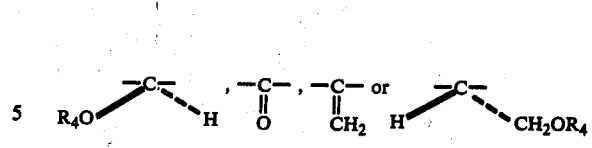

Also included are corresponding compounds wherein the cyclopentane ring is unsaturated between $C_{10}$ and $C_{11}$. Illustrative are compounds of the following formulas:

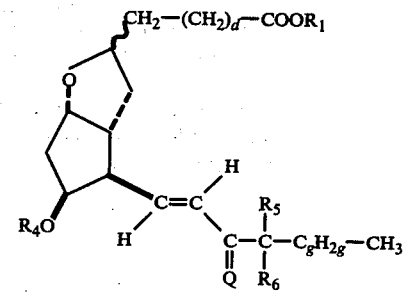

XVIII

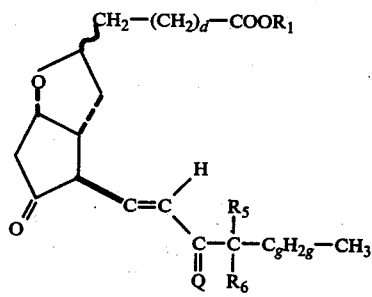

XIX

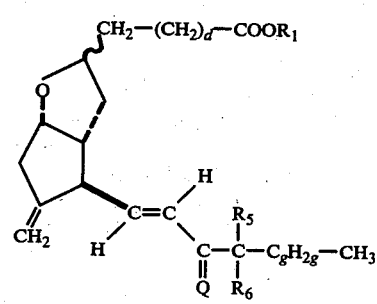

XX

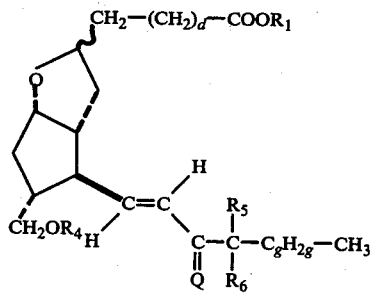

XXI

-continued

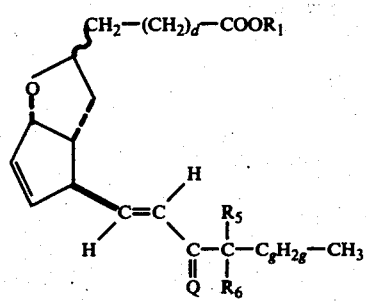
XXII

Also included within the compounds disclosed herein are 9-deoxy-6,9-epoxy compounds corresponding to those of formulas III-XXII wherein the $C_{13}$-$C_{14}$ trans —CH=CH— group is replaced by cis—CH=CH—, —C≡C—, or —CH$_2$CH$_2$—. Merely illustrative but not limiting are compounds of the following formulas:

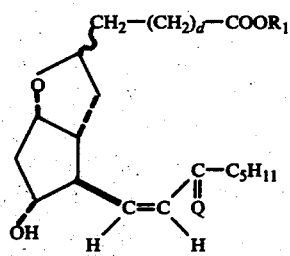
XXIII

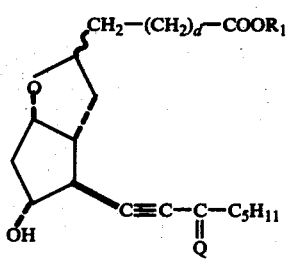
XXIV

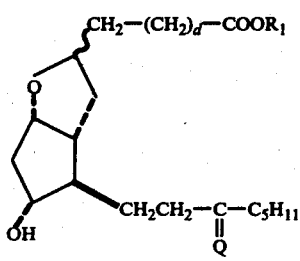
XXV

Still further included within the compounds disclosed herein are 9-deoxy-6,9-epoxy compounds corresponding to those of formulas III-XXVI wherein the $C_2$ carboxylic acid, ester, or salt group is replaced by

—CH$_2$OH
—CH$_2$N(R$_{18}$)$_2$

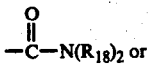

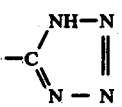

Merely illustrative but not limiting are compounds of the following formulas:

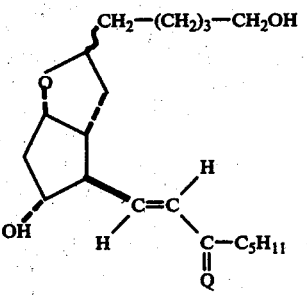
XXVI

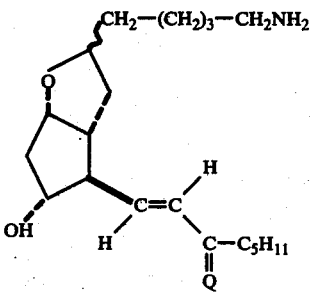
XXVII

-continued

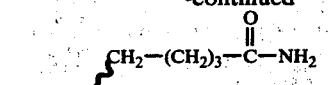
XXVIII

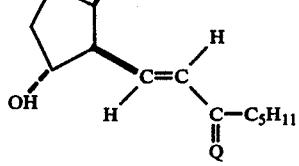
XXIX

Included within these formula-III through -XXIX compounds are the isomers wherein ∼ is in alpha or beta configuration. The nomenclature for these isomers may refer to "α" or "β" substitution at C-6 or, preferably, it may follow the "R" and "S" usage, for which see R. S. Cahn, cited above. See Nelson, J. Medic, Chem. 17, 911 (1974). and J. Am. Chem. Soc. 99, 7362 (1977).

Although these formulas represent specific optical isomers, it is intended that the compounds are claimed not only in their purified form but also in mixtures, including racemic mixtures or mixtures of the enantiomeric forms.

With regard to formulas III to XXIX, examples of alkyl of 1 to 4 carbon atoms, inclusive, are methyl, ethyl, propyl, butyl, and isomeric forms thereof. Examples of alkyl of 1 to 8 carbon atoms, inclusive, are those given above and pentyl, hexyl, heptyl, octyl, and isomeric forms thereof. Examples of alkyl of 1 to 18 carbon atoms, inclusive, are those given above and nonyl, decyl, undecyl, dodecyl, tridecyl, tetradecyl, pentadecyl, hexadecyl, heptadecyl, octadecyl, and isomeric forms thereof. Examples of cycloalkyl of 3 to 10 carbon atoms, inclusive, which includes alkyl-substituted cycloalkyl, are cyclopropyl,
2-methylcyclopropyl,
2,2-dimethylcyclopropyl,
2,3-diethylcyclopropyl,
2-butylcyclopropyl,
cyclobutyl,
2-methylcyclobutyl,
3-propylcyclobutyl,
2,3,4-triethylcyclobutyl,
cyclopentyl,
2,2-dimethylcyclopentyl,
2-pentylcyclopentyl,
3-tert-butylcyclopentyl,
cyclohexyl,
4-tert-butylcyclohexyl,
3-isopropylcyclohexyl,
2,2-dimethylcyclohexyl,
cycloheptyl,
cyclooctyl,
cyclononyl, and
cyclodecyl.

Examples of aralkyl of 7 to 12 carbon atoms, inclusive, are benzyl,
phenethyl,
1-phenylethyl,
2-phenylpropyl,
4-phenylbutyl,
3-phenylbutyl,
2-(1-naphthylethyl), and
1-(2-naphthylmethyl).

Examples of phenyl substituted by alkyl of 1 to 4 carbon atoms, inclusive, are (o-, m-, or p-)tolyl,
p-ethylphenyl,
p-tert-butylphenyl, and
2,5-dimethylphenyl.

Examples of alkylene of 1 to 9 carbon atoms, inclusive, with 1 to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on 1 or more carbon atoms thereof, e.g. —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH$_2$—CH(CH$_3$)—. Examples of alkylene of 1 to 9 carbon atoms, inclusive, substituted with 0, 1, or 2 fluoro, with 1 to 6 carbon atoms in the chain, within the scope of $C_jH_{2j}$ as defined above, are those given above for $C_gH_{2g}$ and hexamethylene, including hexamethylene with one or more alkyl substituents on one or more carbon atoms thereof, and including those alkylene groups with 1 or 2 fluoro substituents on 1 or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CH$_2$—CHF—, —CF$_2$—CH$_2$—CH$_2$—CH$_2$—CH$_2$—, —CH$_2$—CH$_2$—CH$_2$—CF$_2$—CH$_2$—CH$_2$—, and —CH$_2$—CH$_2$—CH$_2$—CH$_2$—CH$_2$—CF$_2$.

Examples of

as defined above are phenyl,
(o-, m-, or p-)tolyl,
(o-, m-, or p-)ethylphenyl,
(o-, m-, or p-)propylphenyl,
(o-, m-, or p-)butylphenyl, (o-, m-, or p-)isobutylphenyl,
(o-, m-, or p-)tert-butylphenyl, 2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-o(o-, m-, or p-)tolyl,
4-butyl-m-tolyl,
6-tert-butyl-m-tolyl,
4-isoproply-2,6-xylyl,
3-propyl-4-ethylphenyl,
(2,3,4-, 2,3,5,-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-chloro-3-fluorophenyl,
(3-, or 4-)chloro-2-fluorophenyl,
α,α,α-trifluoro-(o-, m-, or p-,)tolyl,
(o-, m-, or p-)methoxyphenyl,
(o-, m-, or p-)ethoxyphenyl,
(4- or 5-)chloro-2-methoxyphenyl, and
2-chloro(4- or 5-)methoxyphenyl, Accordingly there is provided a cyclic ether of the formula

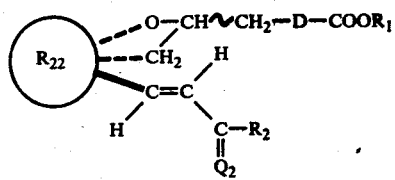  XXX

There is also provided a cyclic ether of the formula

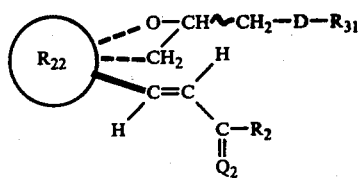  XXXI including the lower alkanoates thereof.
There is also provided a cyclic ether of the formula

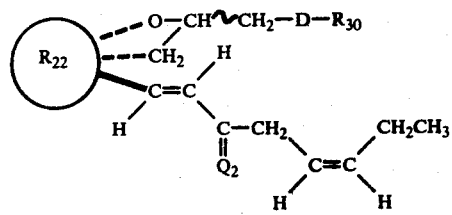  XXXII including the lower alkanoates thereof.
There is further provided a cyclic ether of the formula

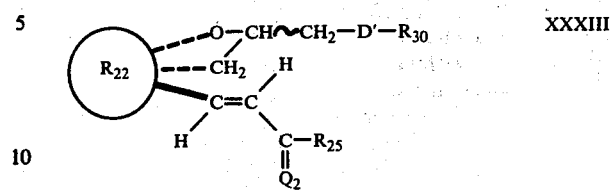  XXXIII including the lower alkanoates thereof.
There is still further provided a cyclic ether of the formula

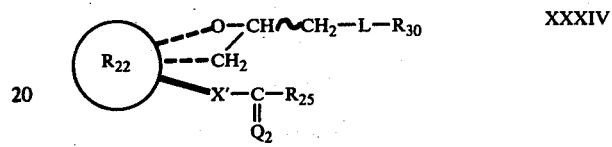  XXXIV including the lower alkanoates thereof.
Included within the scope of $R_{22}$ in formula III, and following the above nomenclature, are 11β compounds, 11-deoxy-11-oxo (PGD) compounds, 11-deoxy-11-methylene compounds, 11-deoxy compound, 11-deoxy-10,11-didehydro compounds, and 11-deoxy-11-hydroxymethyl compounds.

Considering the scope of $R_{30}$ in formula III, there are included acids, esters, salts, 2-decarboxy-2-hydroxymethyl compounds, amides, and 2-decarboxy-2-tetrazolyl compounds.

Included in this invention are the pharmacologically acceptable salts when $R_1$ is hydrogen. Pharmacologically acceptable salts of these formula III–XXV, XXX, and XXXII–XXXIV compounds useful for the purposes described herein are those with pharmacologically acceptable metal cations, ammonium, amine cations, or quarternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternayr ammonium cations are tetramethylammonium, tetraethylammonium, benzyltrimethylammonium, phenyltriethylammonium, and the like.

The novel 5,6-dihydro-prostacyclin-type compounds of formula IV-XXXIV wherein $R_4$ is hydrogen have qualitatively the same pharmacological properties described above for prostacyclin or prostacyclin-type compounds and can be used for the same purposes and in the same manner described above. But quite surprisingly, these novel 5,6-dihydro-prostacyclin-type compounds are substantially more specific with regard to potency in causing prostacyclin-like biological responses. Therefore each of these novel prostacyclin analogs is more useful than prostacyclin for at least one of the pharmacological purposes indicated above. Use of the novel analog for that purpose results in smaller undesired side effects than when prostacyclin is used for the same purpose. Moreover, because of its prolonged activity, fewer and smaller doses of the novel analog can frequently be used to attain the desired result.

These 5,6-dihydro-prostacyclin-type compounds are especially useful for inhibition of platelet aggregation in blood for either in vivo or in vitro applications described above.

To obtain the optimum combination of biological response specificity, potency, and duration of activity, certain compounds within the scope of the formulas IV-XXXIV are preferred. For example it is preferred that Q be

wherein it is especially preferred that $R_3$ be hydrogen or methyl.

However, for those compounds in which $R_2$ is

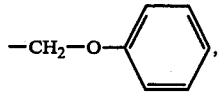

it is equally preferred that Q be

wherein $R_3$ is hydrogen or methyl.

Compounds of formula III are especially useful as intermediates as disclosed herein. Compounds of formulas IV-XXXIV wherein $R_4$ is tetrahydropyranyl or a blocking group as defined herein are useful as intermediates, as disclosed herein, for example in transformations from one to another of the compounds of XXX-XXXIV.

Another preference, for the compounds of formulas III-XXV and XXX, is that $R_1$ in $-COOR_1$ be either hydrogen or alkyl or 1 to 4 carbon atoms, inclusive, especially methyl or ethyl, for optimum absorption on administration, or a salt of a pharmacologically acceptable cation. Likewise, it is preferred, for the compounds of formulas XXXII-XXXIV, that $R_{19}$ when $R_{30}$ is $-COOR_{19}$ be either hydrogen or alkyl of 1 to 12 carbon atoms, inclusive, especially methyl or ethyl, for optimum absorption on administration, or a salt of a pharmacologically acceptable cation.

For purposes of stability on long storage, it is preferred that $R_{32}$ in $-COOR_{32}$ for compounds of formulas XXXII-XXXIV be amido-substituted phenyl or substituted phenacyl, as illustrated herein.

For oral administration it is preferred that $R_{31}$ in compounds of formula XXXI or that $R_{30}$ in compounds of formulas XXXII-XXXIV be

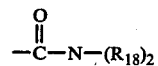

wherein $R_{18}$ is hydrogen, alkyl of 1 to 12 carbon atoms, inclusive, benzyl, or phenyl, especially hydroen or alkyl of 1 to 4 arbon atoms, and more especially hydrogen or methyl, both $R_{18}$'s being the same or different.

When $R_2$ in the compounds of formulas III-XIV and XXX-XXXI, or $R_{25}$ in the compounds of formulas XXXIII-XXXIV is

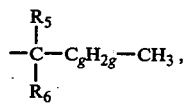

it is preferred that $C_gH_{2g}$ be alkylene of 2, 3, or 4 carbon atoms, and especially that it be trimethylene. It is further preferred that $R_5$ and $R_6$ be hydrogen, methyl, ethyl, or fluoro, eing the same or different. It is further preferred, when $R_5$ and $R_6$ are not hydrogen, that both $R_5$ and $R_6$ be methyl or fluoro. It is especially preferred that $R_2$ or $R_{25}$ be n-pentyl, 1,1-dimethylpentyl, or 1,1-difuloropentyl.

When $R_2$ in the compoundds of formulas III-XIV and XXX-XXXI, or $R_{25}$ in the compounds of formulas XXXIII-XXXIV is

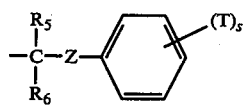

it is preferred that "s" be either 0 or 1. When "s" is not 0, it is preferred that T be methyl, chloro, fluoro, trifluoromethyl, or methoxy with meta or para attachment to the phenyl ring. When Z is oxa (—O—), it is preferred that $R_5$ and $R_6$ be hydrogen, methyl, or ethyl, being the same or different. It is further preferred, when $R_5$ and $R_6$ are not hydrogen, that both $R_5$ and $R_6$ be methyl. When Z is $C_jH_{2j}$, it is preferred that $C_jH_{2j}$ be a valence bond, methylene, or ethylene. It is especially preferred that $R_2$ or $R_{25}$ be

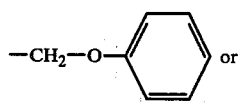 or

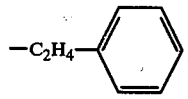

As to variations in $R_{22}$ in the compounds of formulas XXX–XXXIV, it is preferred that $R_{22}$ be

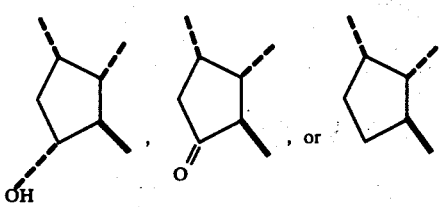

As to variations in D in compounds of formulas XXX–XXXII, and in L in compounds of formula XXXIV, it is preferred that D or L be $-(CH_2)_3-$, $-(CH_2)_4-$, or $-(CH_2)_5-$, and especially $-(CH_2)_3-$.

There are also provided mercury compounds of the formula

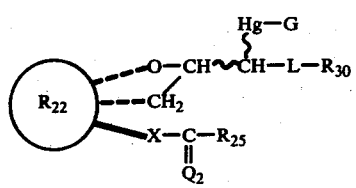

LXXXII wherein G is nitrato, iodo, chloro, bromo, acetato, trifluoroacetato, or benzoato; and wherein L, $Q_2$, $R_{22}$, $R_{25}$, $R_{30}$, X, and ~ are as defined above.

There are also provided mercury compounds of the formula

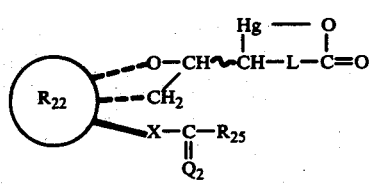

LXXXIII wherein L, $Q_2$, $R_{22}$, $R_{25}$, X, and ~ are as defined above.

The novel mercury compounds disclosed herein are useful for pharmacological purposes. They have antiprotozoal and antisyphilitic activity and are consequently effective in treating streptococci and staphylococci. They have anti microbial activity and are useful for topical antiseptic treatment for animals, including humans, useful domestic animals, pets, zoological specimens, and laboratory animals. They are further useful in ophthalmiatrics.

For these purposes, these mercury compounds are preferably administered topically, for example in alcoholic solution at 0.002 to 0.01% concentration with a benzalkonium chloride as a preservative, or as a lotion, cream, or ointment in 0.5–5.0% concentration in combination with the usual pharmaceutically acceptable diluents. The exact application and concentration depends on such factors as the age, weight and condition of the subject.

Certain mercury compounds within the scope of formula XXXV are preferred for optimum biological response specificity, potency, and duration of activity. For example it is preferred that $Q_2$ be

wherein $R_4$ is hydrogen; it is further preferred that L be trimethylene. When $R_3$ is alkyl, it is preferred that $R_3$ be methyl. Likewise, as to $R_{30}$, when $R_{19}$ in $-COOR_{19}$ is alkyl, it is preferred that $R_{19}$ be alkyl of 1 to 4 carbon atoms, especially methyl. Another preference is that G be chloro or acetato.

The cyclic ethers of formulas XXX–XXXIV, including those of formulas III–XIV, are produced by reactions and procedures described and exemplified hereinafter, as shown schematically in the charts.

Chart A will make clear the steps by which a cyclic ether of the formula

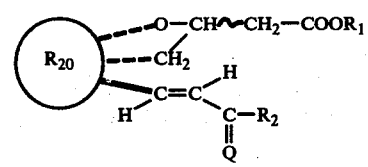

XL is prepared by starting with a lactone of the formula

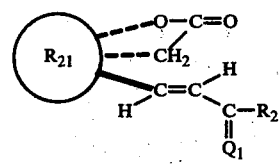

XXXVII and (a) reducing that lactone to a formula-XXXVIII lactol, (b) reacting that lactol with an anion derived rom a substituted acetate of the formula $R_{12}OOC-CH_2-R_{13}$ wherein $R_{12}$ is alkyl of 1 to 8 carbon atoms, inclusive, and $R_{13}$ is the group $-P(C_6H_5)_3$ or $-P(O)(OR_{12})_2$, to produce a compound of formula XXXIX, and (c) transforming the product of step (b) to the formula-XL compound by methods known in the art, including acid hydrolysis of blocking groups $R_{40}$, saponification of ester groups $R_{12}$, and reesterification as desired within the scope of $R_1$. Separation of XL isomers is achieved by silica gel chromatography.

In Chart A, the terms Q, $R_1$, $R_2$, and ~ have the same meanings as defined above.

CHART A

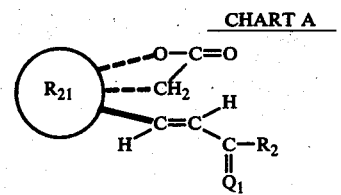

XXXVII

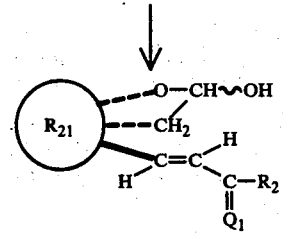

XXXVIII

-continued
CHART A

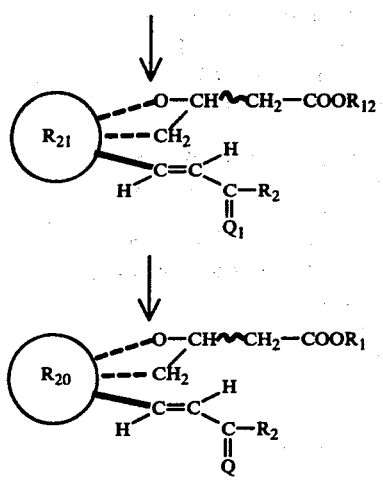

The formula-XXXVII lactone reactants are known in the art or are available by processes known in the art. For example, when R₂₁ is where THP is tetrahydropyran-2-yl and R₂ is alkyl, see Corey et al., J. Am. Chem. Soc. 92, 397 (1970), and U.S. Pat. No. 3,931,279 issued to N. A. Nelson; when R₂ is phenyl-substituted, see U.S. Pat. No. 3,987,087 issued to G. L. Bundy, and Derwent Farmdoc Abstracts, Nos. 76,383T, 5,789U, 73,279U, and 6,479W.

When R₂₁ is these 11β lactones are obtained by isomerizing a corresponding lactone having the 11α configuration, with suitable blocking at the C-15 position if desired, by methods known in the art, such as by way of the 11-mesylate or 11-tosylate. For application of the 11-benzoate for example, see Mitsunobu et al., J. Am. Chem. Soc. 94, 679 (1972).

When R₂₁ is and R₂ is alkyl, see U.S. Pat. No. 3,931,279 and Derwent Farmdoc Abstract No. 10,695V; when R₂ is phenyl-substituted, also see U.S. Pat. No. 3,931,279.

When R₂₁ is a suitable starting material is

See E. J. Corey et al., Tetrahedron Lett. 107 (1972). After introduction of the R₂-containing side chain by known methods including the Wittig reaction and reduction of the 15-oxo group, the methyl ether is hydrolyzed to the lactone in acid.

When R₂₁ is the lactone is available or prepared by processes known in the art. See Ger. Offen. 2,437,622 and Derwent Farmdoc Abstract No. 12,714W. For example a compound of the formula is reduced at the —COOH position to the corresponding —CH₂OH compound using diborane.

When R₂₁ is the hydroxylmethyl compound immediately above is converted first to a tosylate

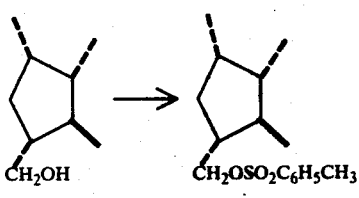

by known methods such as reaction with toluenesulfonyl chloride in 50% excess in the presence of pyridine at above 25° C.; the tosyl group is then exchanged with iodide, e.g. sodium iodide in acetone at about 25°–40° C. to form the corresponding iodomethyl compound;

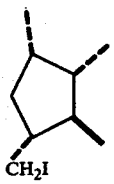

that iodomethyl compound is then dehydroiodinated, for example with potassium tert-butoxide in tetrahydrofuran at −50° C. or below, to yield the methylene compound:

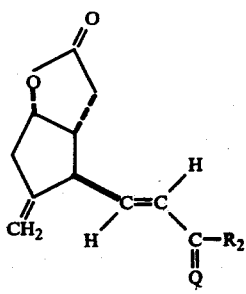   LXXXV

The formula-XXXVIII lactol is obtained on reduction of lactone XXXVII without reducing the ethylenic group. For this purpose, diisobutylaluminum hydride is used as known in the art. The reduction is preferably done at −60° to −78° C.

The formula-XXXIX intermediate is obtained from the lactol by reaction with an anion derived from either a phosphonoacetate of the formula

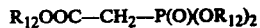   LXXIV or a carboxymethylphosphonium compound of the formula

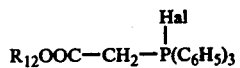   LXXV wherein $R_{12}$ is alkyl of 1 to 8 carbon atoms, inclusive and Hal is chloro, bromo, or iodo. Alternatively, the phosphonium compound may be referred to by its ylid form,

   LXXVa

The reaction is done in the presence of a base, preferably potassium t-butoxide or sodium hydride for LXXIV, or potassium t-butoxide, sodium ethoxide, benzyltrimethylammonium hydroxide, or, preferably, an alkali metal hydroxide for LXXV, usually at 0°–25° C.

The formula-XL product is obtained on replacement of the $R_{40}$ blocking groups with hydrogen, by acid hydrolysis, for example in dilute acetic acid, aqueous citric acid, or aqueous phosphoric acid-tetrahydrofuran. When $R_1$ in the product is different than $R_{12}$, transformation is brought about by methods known in the art, including saponification to yield the acid, optionally followed by esterification. Esters are conveniently prepared by interaction of the acid with an appropriate diazohydrocarbon. For example, when diazomethane is used, the methyl esters are produced. Similar use of diazoethane, diazobutane, and 1-diazo-2-ethylhexane for example, gives the ethyl, butyl, and 2-ethylhexyl esters, respectively. Of these esters, it is preferred that $R_1$ be methyl or ethyl.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol 8, pp. 389–394 (1954).

An alternative method for esterification of the acid compounds herein comprises transformations of the free acid to the corresponding silver salt, followed by interaction of that salt with an alkyl iodide. Examples of suitable iodides are methyl iodide, ethyl iodide, butyl iodide, and isobutyl iodide. The silver salts are prepared by conventional methods, for example, by dissolving the acid in cold dilute aqueous ammonia, evaporating the excess ammonia at reduced pressure, and then adding the stoichiometric amount of silver nitrate.

As for all of the reactions described herein, the duration of the reaction is readily determined by monitoring with TLC (thin layer chromatography).

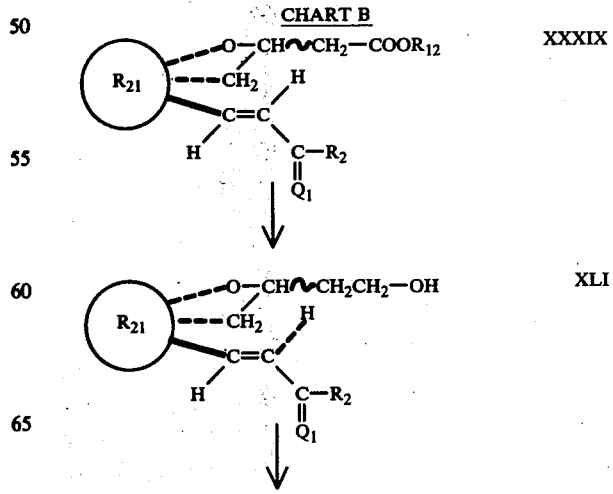

CHART B

-continued
CHART B

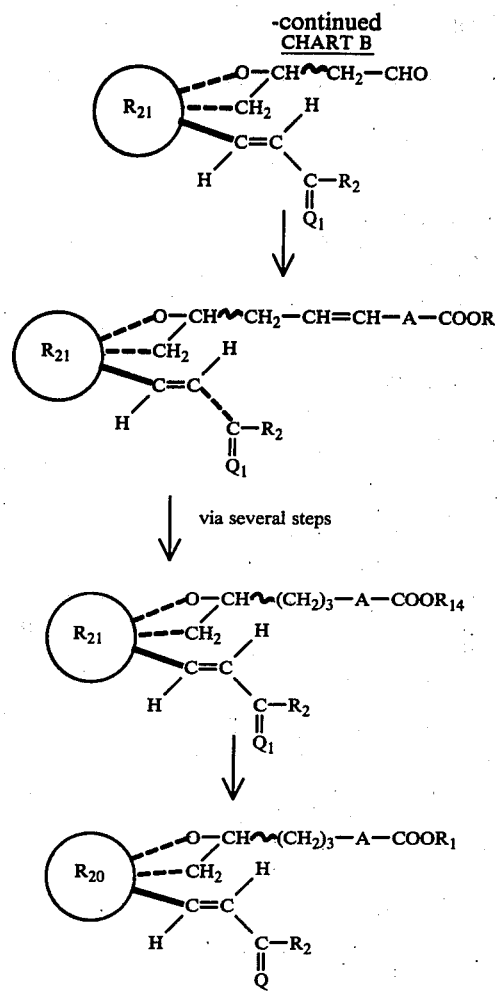

Chart B shows the steps for preparing a cyclic ether of formula XLV by starting with a formula-XXXIX intermdiate of Chart A, reducing that formula-XXXIX ester to a hydroxyethyl compound of formula XLI, oxidizing that formula-XLI alcohol to an aldehyde of formula XLII, subjecting that formula-XLII aldehyde to a Wittig alkylation either (1) with an anion derived from a substituted acetate of the formula $R_{12}OO$-$C$—$CH_2$—$R_{13}$ wherein $R_{12}$ and $R_{13}$ are as defined above to form a compound represented by the formula

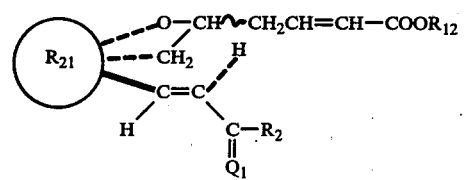

or (2) with an anion derived from an ω-carboxyalkyltriphenylphosphonium halide of the formula

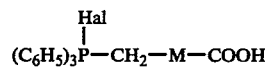

wherein M is —$(CH_2)_h$ wherein $h$ is 1, 2, or 3 and Hal is chloro, bromo, or iodo to form a compound represented by the formula

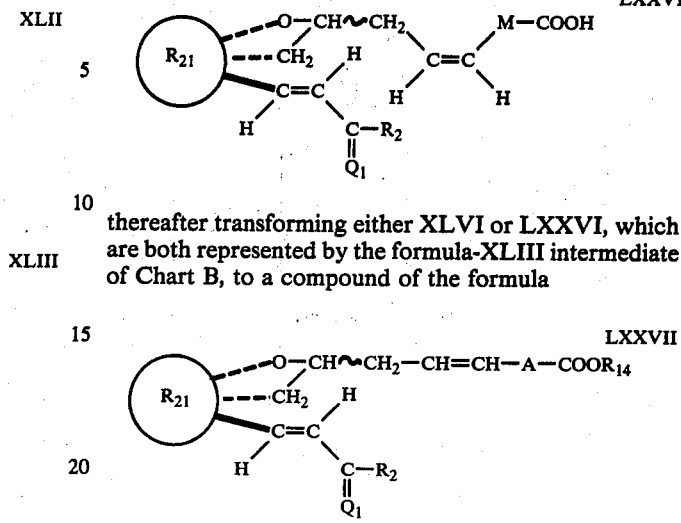

thereafter transforming either XLVI or LXXVI, which are both represented by the formula-XLIII intermediate of Chart B, to a compound of the formula

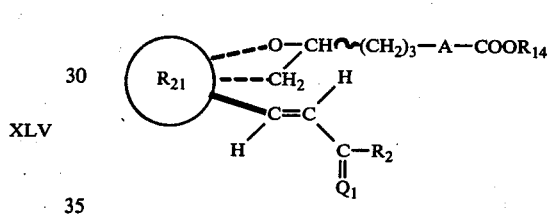

That compound LXXVII is then subjected to selective reduction of the 3,4-ethylenic unsaturation to form a compound of the formula

XLIV and that compound XLIV is then transformed by known methods to the desired formula-XLV cyclic ether.

In Chart B and in the following charts, the terms Q, $Q_1$, $R_1$, $R_2$, $R_{12}$, $R_{20}$, $R_{21}$, and ~ have the same meaning as for Chart A. The term "A" represents a valence bond or —$(CH_2)_h$— wherein $h$ is 1, 2, or 3. The term $R_{14}$ represents hydrogen or an alkali metal cation, e.g. sodium, potassium, or lithium.

In Chart B, the formula-XXXIX intermediates are produced by the steps in Chart A above.

A formula-XLI alcohol is obtained from a formula-XXXIX ester on reduction, by methods known in the art, for example using lithium aluminum hydride or lithium trimethoxyaluminum hydride in a solvent such as diethyl ether or tetrahydrofuran.

The formula-XLII aldehyde is obtained by oxidation of the —$CH_2OH$ of XLI to —CHO, avoiding decomposition of the cyclic ether ring. Useful for this purpose are pyridinium chlorochromate, Jones reagent, Pfitzner-Moffatt reagent and especially, Collins' reagent (pyridine-$CrO_3$) at about 0°–15° C.

The formula-XLIII compound is obtained by Wittig alkylation using an anion derived from an appropriate phosphonate or phosphonium compound. If "A" is a valence bond, a compound of the formula $R_{12}OO$-$C$—$CH_2$—$R_{13}$ is used, wherein $R_{12}$ is alkyl of 1 to 8 carbon atoms, inclusive, and $R_{13}$ is the group —$\overset{+}{P}(C_6H_5)_3$ or —$P(O)(OR_{12})_2$. See for example D. H. Wadsworth et al., J. Org. Chem. 30, 680 (1965) as to phosphonates. See also Organic Reactions Vol. 14, Chapter 3, John Wiley and Sons, Inc., N.Y. (1965) as to the Wittig reaction. When A is a valence bond, the 3,4-ethylenic group of the XLIII compound is predominately in the trans form. When A is —(CH$_2$)$_h$— wherein $h$ is 1, 2, or 3, the appropriate reagent for the Wittig alkylation is an anion derived from an ω-carboxyalkyl-triphenylphosphonium halide of the formula

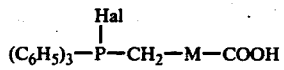   LXXVIII wherein M is (CH$_2$)$_h$ and Hal is chloro, bromo, or iodo. The resulting 3,4-ethylenic group of compound XLIII is then predominately in the cis form.

The formula-XLIII compounds are useful intermediates for preparing the formula-V, -VI, -XI, and -XII end products, following hydrolysis of the blocking groups and conversion of R$_{12}$ to R$_1$ as required. Isomerization of cis to trans or trans to cis, if desired, is accomplished, for example, by ultraviolet radiation as disclosed in U.S. Pat. No. 3,759,978, followed by separation of the product as by chromatography.

Continuing with Chart B, the formula-XLIV compounds are obtained from the formula-XLIII compounds by selective reduction of the 3,4-ethylenic unsaturation. For this purpose several methods are available: For XC above, that of Dennis et al., Tetrahedron Lett. 1821 (1968), utilizing for the acids or salts a cyanonickel complex and sodium borohydride, or preferably, catalytic reduction over 5% palladium (or rhodium) on carbon at about 0° C. for the esters.

Finally, the formula-XLV products are obtained by hydrolysis of the blocking groups and converstion of R$_{14}$ to R$_1$ as required.

Methods of separating the products similar to those known in the art are employed, including extraction, chromatography, crystallization, and the like.

Chart C shows the steps for preparing a cyclic ether of formula XLVII by starting with a formula-XXXVIII lactol of Chart A, reacting that lactol with a 4-(triphenylphosphoranylidene) crotonic acid ester, for example the methyl ester (Buchta et al., Chem. Ber. 92, 3111 (1959)) obtained from the corresponding phosphonium compound. The reaction is done in a temperature range of 70°-120° C. and is conveniently done in refluxing benzene to yield the formula-XLVI intermediate. The product XLVII is obtained on hydrolysis of the blocking groups and conversion of R$_{12}$ to R$_1$ as required.

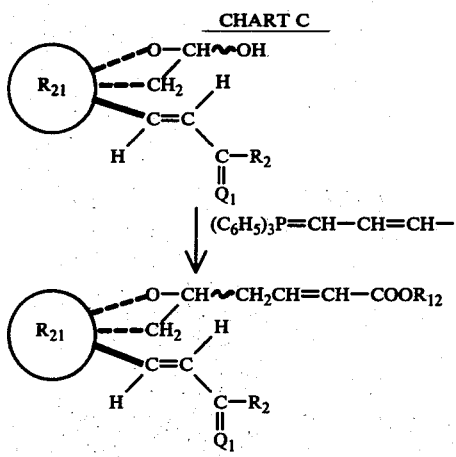

-continued
CHART C

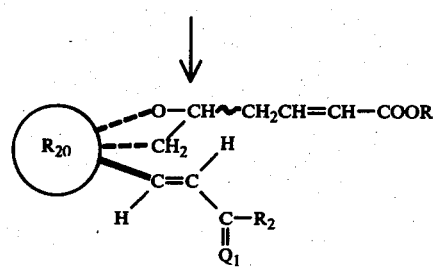

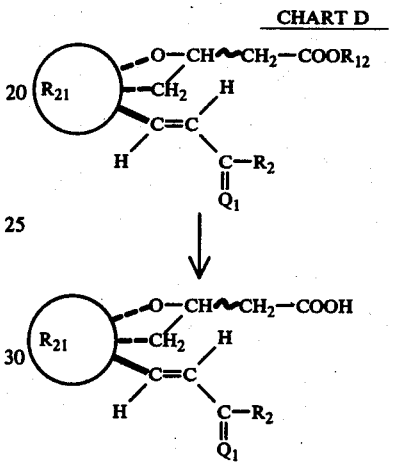

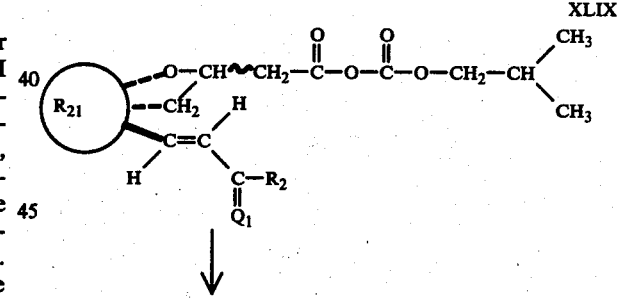

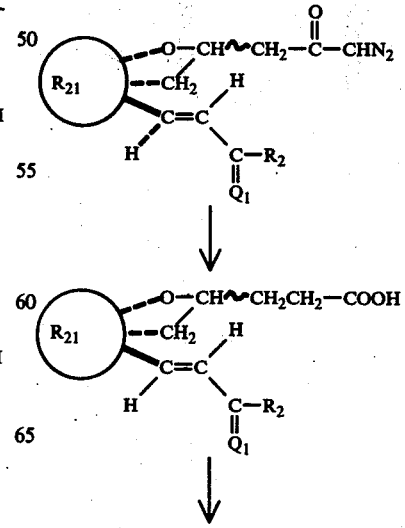

-continued
CHART D

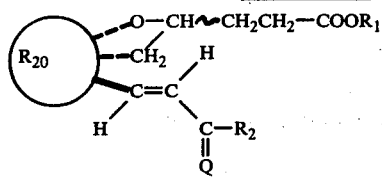
LII

Chart D shows the steps for preparing a cyclic ether of formula LII by starting with a formula-XXXIX ester of Chart A, (a) saponifying that ester to form acid XLVIII, (b) forming a mixed anhydride of formula XLIX, (c) forming a diazoketone of formula L, (d) forming a compound of formula LI, and (e) forming the desired formula-LII product.

The formula-XXXIX compound is saponified to yield the acid XLVIII, for example in an aqueous alkaline medium, such as sodium hydroxide to form an alkaline salt which is then acidified to yield the free acid.

The acid XLVIII is converted to anhydride XLIX by reaction with isobutylchloroformate in the presence of an organic tertiary amine. The anhydride is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the acid XLVIII. The reaction is preferably done in a solvent and for this purpose acetone is preferred, although other relatively nonpolar solvents are used such as acetonitrile, dichloromethane and chloroform. The reaction is run in the presence of a tertiary amine, for example triethylamine, and the coformed amine hydrochloride usually crystallizes out, but need not be removed for the next step.

Diazoketone L, obtained by reaction of anhydride XLIX with diazomethane, yields compound LI on contacting with water and a catalyst such as colloidal silver, platinum, or copper. See Bachmann et al., Org. Reactions Vol. 1, page 38 (1942). Thereafter compound LI yields a 6ξ,9α-epoxy ether within the scope of formula IV or X by methods described herein.

CHART L

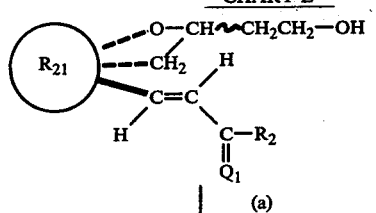
XLI (a)

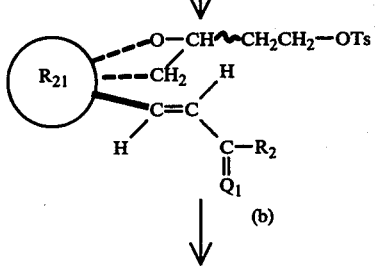
LXXXVI (b)

-continued
CHART L

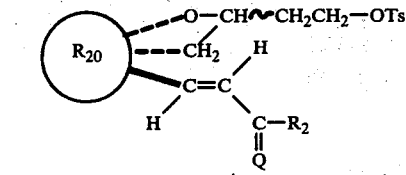
LXXXVII (c)

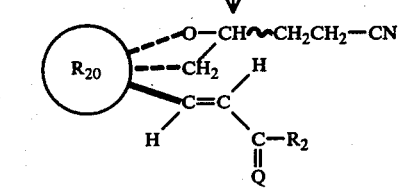
LXXXVIII (d)

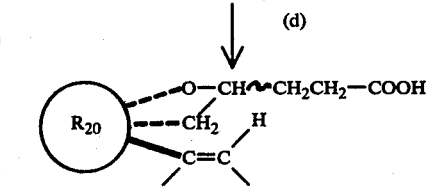
LXXXIX (e)

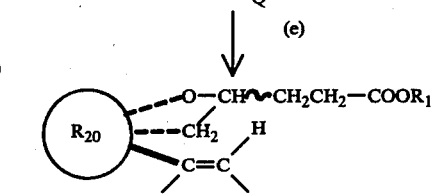
LII

Chart L, herein, shows the steps of an alternate process for preparing a cyclic ether of formula LII by starting with a formula-XLI hydroxyethyl compound of Chart B, (a) transforming that formula-XLI alcohol to tosylate LXXXVI, (b) optionally removing blocking groups such as THP groups by acid hydrolysis to form compound LXXXVII, (c) exchanging tosylate groups with nitrile groups to form nitrile LXXXVIII, (d) hydrolyzing that nitrile to acid LXXXIX, and (e) optionally forming esters within the scope of formula LII. In Chart L, the terms Q, $Q_1$, $R_1$, $R_2$, $R_{20}$, $R_{21}$, and ~ are as used above for Chart A, and Ts represents the p-toluenesulfonyl ("tosyl") group.

Tosylate LXXXVI is formed by treating the alcohol XLI with p-toluenesulfonyl chloride in excess tertiary amine, preferably pyridine, at room temperature. Thereafter blocking groups are optionally removed, as by acid hydrolysis, to form a compound represented by formula LXXXVII.

Nitrile LXXXVIII is obtained on treating the tosylate with sodium or potassium cyanide in a solvent such as hexamethylphosphoramide, dimethylformamide, dimethylsulfoxide, or N-methyl pyrrolidone. The reaction proceeds smoothly at room temperature.

Acid LXXXIX is formed by alkaline hydrolysis of the nitrile, with subsequent acidification as known in the art.

Finally, esters within the scope of LII are made if desired by methods known or disclosed herein.

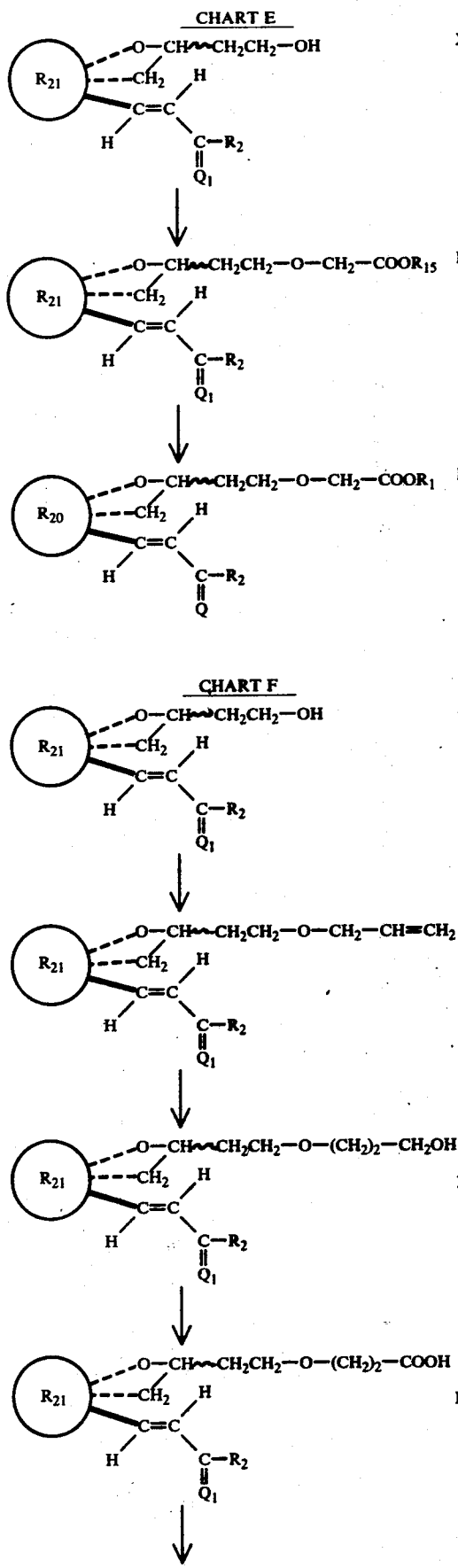
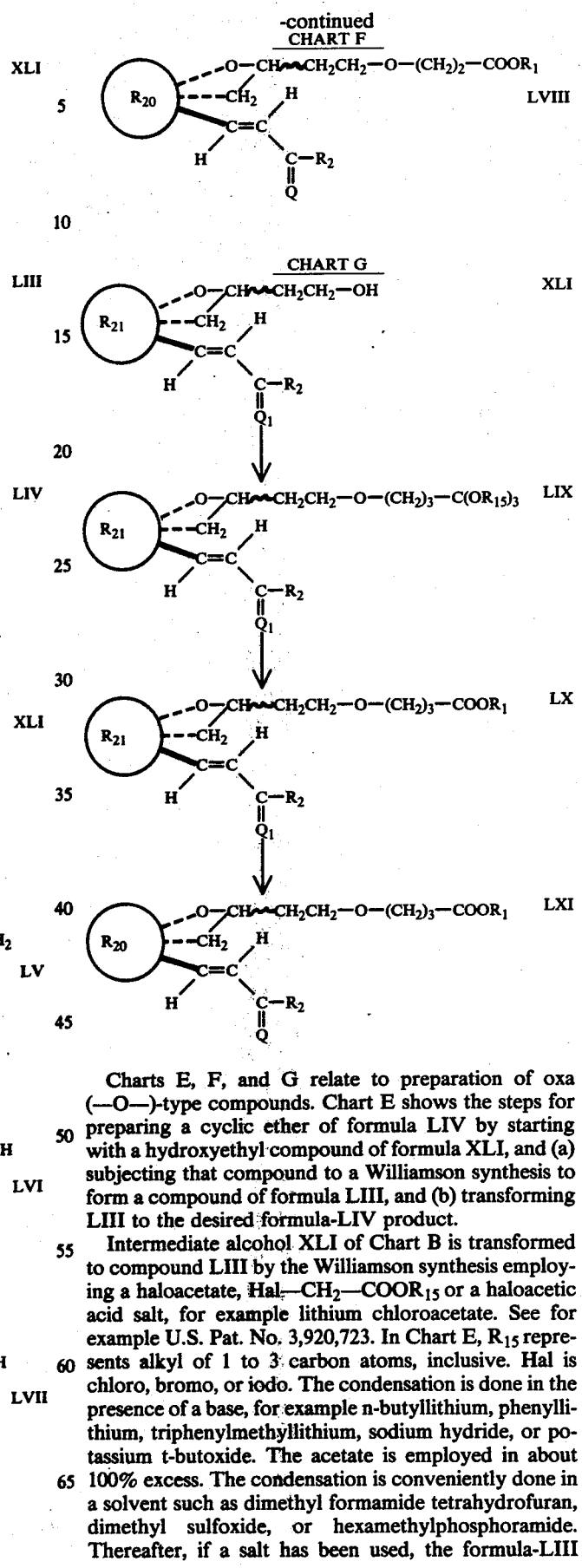

Charts E, F, and G relate to preparation of oxa (—O—)-type compounds. Chart E shows the steps for preparing a cyclic ether of formula LIV by starting with a hydroxyethyl compound of formula XLI, and (a) subjecting that compound to a Williamson synthesis to form a compound of formula LIII, and (b) transforming LIII to the desired formula-LIV product.

Intermediate alcohol XLI of Chart B is transformed to compound LIII by the Williamson synthesis employing a haloacetate, Hal—$CH_2$—$COOR_{15}$ or a haloacetic acid salt, for example lithium chloroacetate. See for example U.S. Pat. No. 3,920,723. In Chart E, $R_{15}$ represents alkyl of 1 to 3 carbon atoms, inclusive. Hal is chloro, bromo, or iodo. The condensation is done in the presence of a base, for example n-butyllithium, phenyllithium, triphenylmethyllithium, sodium hydride, or potassium t-butoxide. The acetate is employed in about 100% excess. The condensation is conveniently done in a solvent such as dimethyl formamide tetrahydrofuran, dimethyl sulfoxide, or hexamethylphosphoramide. Thereafter, if a salt has been used, the formula-LIII compound is obtained by methods known in the art. Product LIV, which includes products VII and XIII, is obtained by the usual steps of hydrolyzing off the blocking groups and converting $R_{15}$ to $R_1$ if required.

Chart F shows the steps in preparing a cyclic ether of formula LVIII by starting with a hydroxyethyl compound of formula XLI, and (a) subjecting that hydroxyethyl compound to a Williamson synthesis with an allyl halide to form a compound of formula LV, (b) forming an alcohol of formula LVI, (c) oxidizing the terminal hydroxyl group of that alcohol to yield a carboxylic acid of formula LVII, and (d) thereafter transforming that acid to the desired formula-LVIII product.

Intermediate alcohol XLI of Chart B is transformed to compound LV by a Williamson ether synthesis, employing allyl chloride. See for example U.S. Pat. No. 3,920,723. Thereafter, hydroboration yields alcohol LVI. See, for example, "Hydroboration", H. C. Brown, W. A. Benjamin, Inc., New York, 1962. The formula-LVII acid is obtained by oxidation, for example with the Jones reagent. Finally, blocking groups are removed by methods described above. The product is esterified if desired to yield the formula-LVIII product.

Chart G shows the steps in preparing a cyclic ether of formula LXI by starting with a hydroxyethyl compound of formula XLI, and (a) condensing that hydroxyethyl compound with an omega-halo ortho ester of the formula: $Hal-(CH_2)_3-C(OR_{15})_3$, wherein Hal and $R_{15}$ are as defined for Chart E, to form a compound of formula LIX, (b) transforming compound LIX to a compound of formula LX, and (c) thereafter transforming compound LX to the desired formula-LXI product.

Compound LIX is obtained from alcohol XLI by a Williamson synthesis preferably employing an ortho-4-bromobutyrate of the formula $Hal-(CH_2)_3-C(OR_{15})_3$ wherein Hal is chloro, bromo, or iodo and wherein $R_{15}$ is as defined above. See for example U.S. Pat. No. 3,921,279. The condensation is done in the presence of a base and a solvent, for example potassium t-butoxide and tetrahydrofuran, or n-butyllithium and hexamethylphosphoramide. The reaction proceeds smoothly at $-20°$ to $+50°$ C. but is preferably done at about $25°$ C. for convenience. Following the condensation, the formula-LX compound is obtained by methods known in the art, for example by hydrolysis in cold dilute mineral acid. Finally, product LXI, which is within the scope of formulas VIII and XIV, is obtained by hydrolysis of blocking groups and conversion of $R_{15}$ to $R_1$ as required.

Included among the compounds of formula XXX are 11-oxo compounds. For their preparation, the processes of Charts A-G are employed, but replacing starting materials XXXVII, XXXVIII, XXXIX, and XLI with corresponding compounds wherein $R_{21}$ is replaced by

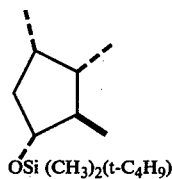

OSi(CH$_3$)$_2$(t-C$_4$H$_9$)

Such compounds are available by methods known in the art or described herein. For this purpose there are prepared lactones of the formula

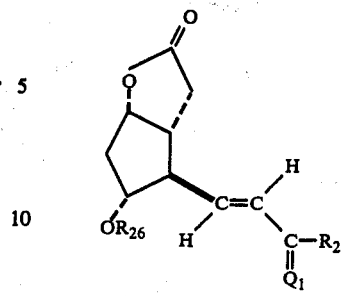

LXXIX wherein $Q_1$ and $R_2$ are as defined above and $R_{26}$ is a carboxyacyl blocking group:

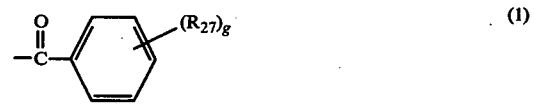

(1)

wherein $R_{27}$ is alkyl of 1 to 4 carbon atoms, inclusive, phenylalkyl of 7 to 10 carbon atoms, inclusive, phenyl or nitro, and g is 0 to 5, inclusive, provided that not more than two $R_{27}$'s are other than alkyl, and that the total number of carbon atoms in the $R_{27}$'s does not exceed 10 carbon atoms;

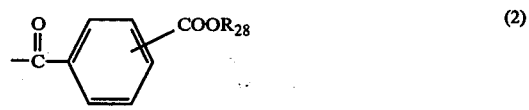

(2)

wherein $R_{28}$ is alkyl of one to 4 carbon atoms, inclusive; or

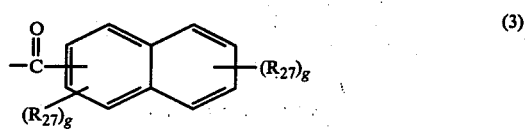

(3)

wherein $R_{27}$ and g are as defined above. Starting materials for these formula-LXXIX lactones are known or readily available. See for example U.S. Pat. No. 3,931,279.

The formula-LXXIX lactone is transformed to the silylated starting material by replacing $R_{26}$ with hydrogen, as with sodium methoxide in methanol, and blocking at the latent C-11 position with t-butyldimethylsilyl. See E. J. Corey et al., J. Am. Chem. Soc. 94, 6190 (1972).

Thereafter, the procedures of Charts A-G yield compounds bearing the t-butyldimethylsilyl group at C-11. This group is then replaced with hydrogen using tetrabutylammonium fluoride. See Corey et al. cited above. Next the 11-hydroxy group is oxidized to 11-oxo, for example by Jones oxidation, and finally the $R_{40}$ groups at C-15 are replaced, if desired, by acid hydrolysis.

Also included among the compounds of formula XXX are 11-methylene compounds. Alternate methods for their preparation, other than those included within Charts A-G above wherein $R_{21}$ is

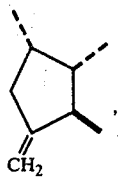

utilize those processes of Charts A–G by replacing starting materials XXXVII, XXXVIII, XXXIX, and XLI with corresponding compounds wherein $\widehat{R_{21}}$ is replaced by

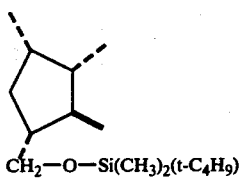

Such compounds are readily prepared from the hydroxymethyl lactones wherein $\widehat{R_{21}}$ is

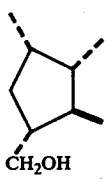

described herein for the starting materials of Chart A, using the procedures of Corey et al. cited above.

Thereafter the procedures of Charts A–G yield compounds bearing the t-butyldimethylsilyloxymethyl group at C-11. It is preferred that $R_1$ be alkyl. Next the silyl groups are replaced with hydrogen using tetrabutylammonium fluoride, and the resulting hydroxymethyl groups are converted to iodomethyl groups by way of tosylation and iodide exchange. Finally dehydroiodination, as with potassium tert-butoxide in tetrahydrofuran, yields the 11-methylene compounds.

Also included among the compounds of formula XXX are 15-deoxy compounds. For their preparation, the products of Charts A–G wherein Q is

in their free acid form, are used. They are (1) silylated, e.g. with t-butyldimethylsilyl chloride and imidazole, (2) hydrolyzed to remove silyl ester groups at C-1, e.g. with aqueous potassium hydroxide, (3) reduced with lithiumneopentyl alcohol-methyl amine at about −30° C., and (4) hydrolyzed to remove silyl ether groups, thereby yielding 15-deoxy products.

Alternatively, a lactone of the formula

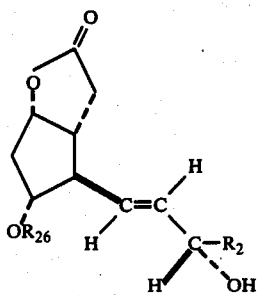

LXXX wherein $R_2$ and $R_{26}$ are as defined above is (1) transformed to the 3α-bromo compound, (2) reduced with sodium borohydride in dimethylsulfoxide, (3) treated with potassium carbonate to replace $-OR_{26}$ with hydroxyl and (4) blocked at the hydroxyl sites with $-OR_{40}$ wherein $R_{40}$ is as defined above. Thereby a lactone is obtained of the formula

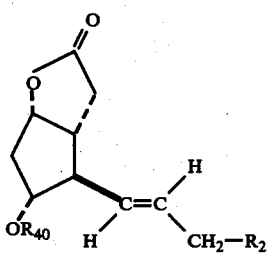

LXXXI which is used to replace lactone XXXVII in Chart A and the processes of Charts A–G for preparing 15-deoxy products.

An alternative method for preparing the formula IV, VII, VIII, X, XIII, XIV, XV, XVI, and XXX-XXXIV cyclic ethers is by reductive dehalogenation of a compound of the formula

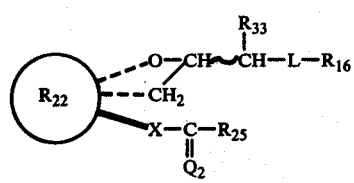

LXIII wherein $R_{33}$ is iodo or bromo.

Chart H shows the steps by which a PGF$_{2\alpha}$-type compound of formula LXII is (a) halogenated and cyclized to form a compound of formula LXIII, and the compound LXIII is subjected to reductive dehalogenation to form the formula-LXIV product. In Chart H the terms are defined as for compound LXIII above.

CHART H

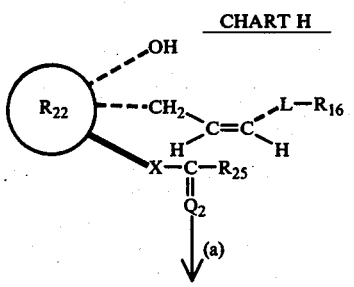

LXII

-continued
CHART H

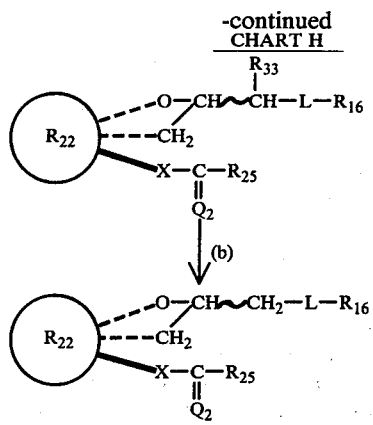

The starting materials of formula LXII are prostaglandins or prostaglandin-like materials known in the art or readily available by processes known in the art. Either the compounds in which $R_4$ of $R_{22}$ and $Q_2$ is hydrogen or those in which $R_4$ is a blocking group may be used. For example, as to $PGF_{2\alpha}$ see U.S. Pat. No. 3,706,789; as to 15-methyl- and 15-ethyl-$PGF_{2\alpha}$, see U.S. Pat. No. 3,728,382; as to 16,16-dimethyl-$PGF_{2\alpha}$, see U.S. Pat. No. 3,903,131; as to 16,16-difluoro-$PGF_{2\alpha}$, see U.S. Pat. No. 3,969,380; as to 2-decarboxy-2-hydroxymethyl compounds, see U.S. Pat. No. 3,636,120; as to 2-decarboxy-2-tetrazolyl derivatives, see U.S. Pat. Nos. 3,883,513 and 3,932,389; as to 2,3-didehydro-$PGF_{2\alpha}$ see Derwent Farmdoc No. 46,497W and Ger. Offen. 2,460,285; as to 11-deoxy-11-hydroxymethyl-$PGF_{2\alpha}$, see U.S. Pat. Nos. 3,931,282 and 3,950,363; as to 16-methylene-$PGF_{2\alpha}$, see Derwent Farmdoc No. 19,594W and U.S. Pat. No. 3,953,495; as to 17,18-didehydro-$PGF_{2\alpha}$ compounds, see U.S. Pat. No. 3,920,726; as to 3-(or 4-)oxa-17,18-didehydro-$PGF_{2\alpha}$ compounds, see U.S. Pat. No. 3,920,723; as to 15-oxo-$PGF_{2\alpha}$, see U.S. Pat. No. 3,728,382; as to 15-deoxy-$PGF_{2\alpha}$, see Derwent Farmdoc No. 09,239W; as to 11-deoxy-15-deoxy-$PGF_{2\alpha}$ Derwent Farmdoc No. 05,694U and U.S. Pat. No. 3,853,951; as to ω-homo-$PGF_{2\alpha}$ compounds, see Derwent Farmdoc No. 04,728W; as to 2-decarboxy-2-amino-$PGF_{2\alpha}$ compounds, see Preparation 1 herein or U.S. Pat. No. 4,028,350; as to 16-phenoxy-17,18,19,20-tetranor-$PGF_{2\alpha}$, see Derwent Farmdoc No. 73,279U; as to 17-phenyl-18,19,20-trinor-$PGF_{2\alpha}$, see U.S. Pat. No. 3,987,087; as to 13-cis-$PGF_{2\alpha}$, see U.S. Pat. No. 3,932,479; as to 13,14-didehydro-$PGF_{2\alpha}$, see Derwent Farmdoc No. 20,717X and 59,715X; as to 11-deoxy-$PGF_{2\alpha}$, see Derwent Farmdoc No. 10,695V; as to $PGD_2$, see U.S. Pat. No. 3,767,813; as to 2a,2b-dihomo-$PGF_{2\alpha}$, see Derwent Farmdoc No. 61,412S; as to 3-oxa-$PGF_{2\alpha}$, see U.S. Pat. No. 3,923,861; as to 3-oxa-17-phenyl-18,19,20-trinor-$PGF_{2\alpha}$, see U.S. Pat. No. 3,931,289; as to 2,2-difluoro-$PGF_{2\alpha}$, see U.S. Pat. No. 4,001,300; as to 11β-$PGF_{2\alpha}$, see U.S. Pat. No. 3,890,371; and as to 11β-17-phenyl-18,19,20-trinor-$PGF_{2\alpha}$, see Derwent Farmdoc No. 13,090X.

In step "a" of Chart H, the starting material LXII is subjected to halogenation and cyclization to yield the formula-LXIII halo compounds. For related cyclization procedures see Staninets and Shilov, Chem. Abs. 64, 12,625h (1966). For iodination there is used either an aqueous system containing iodine, potassium iodide, and an alkali carbonate or bicarbonate, or an organic solvent system such as dichloromethane containing iodine in the presence of an alkali metal carbonate. The reaction is carried out at temperatures below 25° C., preferably about 0°–5° C. for 10–20 hr. Thereafter the reaction is quenched with sodium sulfite and sodium carbonate and the formula-LXIII compound separated from the reaction mixture. For bromination N-bromosuccinimide or N-bromoacetamide are used. See Fieser et al., Reagents for Organic Synthesis, Vol. 1, pp. 74 and 78, Vol. IV p. 51, John Wiley and Sons, Inc., New York.

In step "b" of Chart H the halo compound LXIII is subjected to reductive dehalogenation. Useful reagents include tributyltin hydride, triphenyltin hydride, sodium borohydride in dimethyl sulfoxide, and zinc in acetic acid. Especially preferred is tributyltin hydride freshly prepared from tributyltin chloride and lithium aluminum hydride. The reaction is run in a solvent such as benzene at about 15°–35° C. and monitored by TLC.

Thereafter, any blocking groups are removed by methods known in the art and the product isolated by methods described herein or known in the art, for example by chromatography on silica gel.

A preferred method for preparing amides of formula LXII

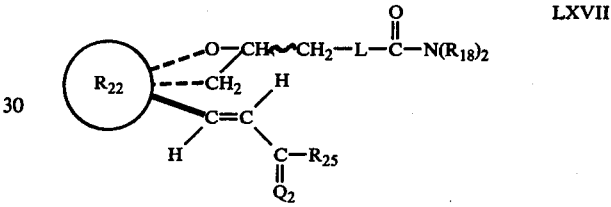

is by the steps shown in Chart I. The halo acid LXV is converted to amide LXVI and thence, by reductive dehalogenation to the formula-LXVII amide. In Chart I, $R_{18}$ is hydrogen, alkyl of 1 to 12 carbon atoms, inclusive, benzyl, or phenyl, being the same or different.

Another method for preparing the formula-IV, VII, VIII, X, XIII, XIV, XV, XVI, and XXX-XXXIV cyclic ethers is by reductive demercuration of a compound of the formula

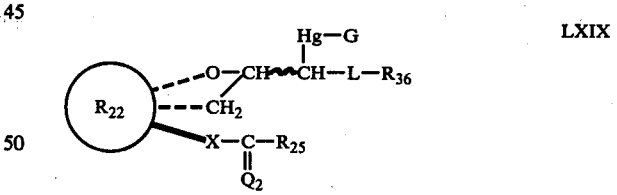

wherein L, $Q_2$, $R_{22}$, $R_{25}$, X and ~ are as defined for Chart H and wherein G is nitrato, iodo, chloro, bromo, acetato, trifluoroacetato or benzoato.

CHART I

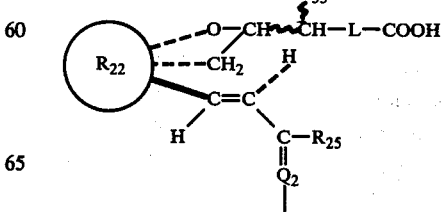

-continued
CHART I

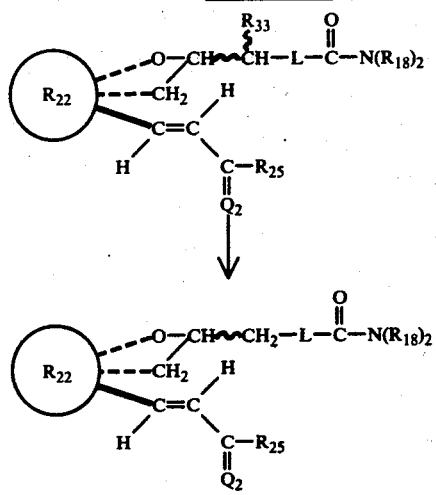

Chart J shows the steps by which a PGF$_{2\alpha}$-type compound of formula LXVIII is (a) converted to a mercury compound of formula LXIX and (b) compound LXIX is subjected to reductive demercuration to form the formula-LXX product. In Chart J the terms are defined as for compound LXIX above.

Reference to Chart J will make clear the steps of this process. For background on this mercuration-demercuration cyclization see, for example, H. C. Brown et al., Organometal. Chem. Syn. 1, 7 (1970) and Fieser and Fieser, Reagents for Organic Synthesis, Vol. 3, p. 194, Wiley, N.Y., 1972.

Many of the formula-LXVIII starting materials have been discussed above for Chart H. As to substituted phenyl esters, see U.S. Pat. No. 3,890,372; and as to substituted phenacyl esters, see Derwent Farmdoc No. 16,828X and German Offen. 2,535,693. In step "a" of Chart J, the starting material is reacted with an appropriate mercury (II) salt corresponding to Hg(G)$_2$, for example mercuric nitrate, chloride, or acetate. Preferred is either mercuric acetate or trifluoroacetate. The reagent is dissolved in either water or acid, e.g. acetic acid, and combined with a solution of the formula-LXVIII starting material in a convenient solvent such as chloroform or tetrahydrofuran. The reaction is conveniently done at about 15°–35° C.

In step "b" of Chart J the mercurio compound is subjected to reductive demercuration. Useful reagents for this step include sodium borohydride, sodium amalgam, and hydrazine. Especially preferred is sodium borohydride in alkaline solution, e.g. aqueous sodium hydroxide. The reaction is carried out in a solvent such as tetrahydrofuran at about 15°–35° C. Thereafter the mercury is separated, blocking groups removed if necessary, and the product isolated by methods described herein.

CHART J

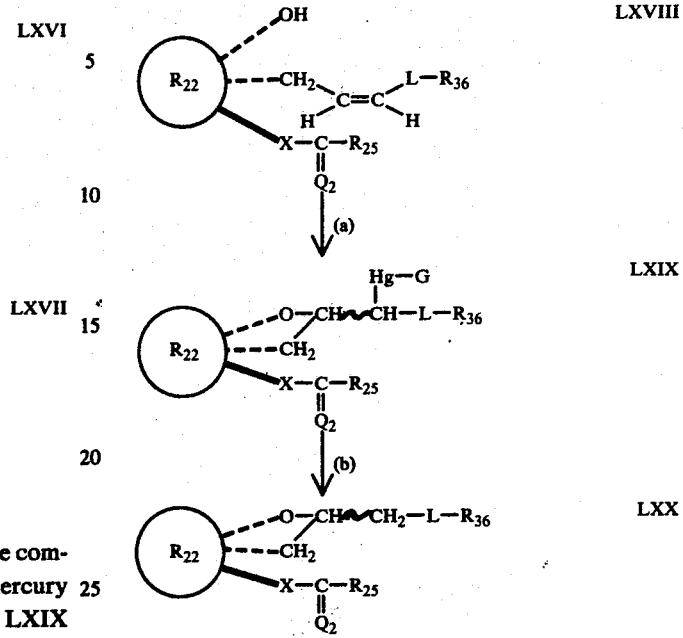

The formula-LXIX mercurio compounds are useful not only as intermediates for preparing the formula-LXX products but also for their pharmacological applications as set forth herein. G may be varied, for example, by suitable choice of reagent Hg(G)$_2$ or by replacement, for example of acetate by chloro by ion exchange.

Chart K shows the formation of formula-LXXXIV compounds, which are inner salts between hydroxymercurio groups and terminal carboxy. They are formed by replacing G with hydroxy, as in basic solution, followed by treatment with acid. They also have pharmacological utility. In Chart K the terms are as defined in Chart J.

The intermediates of Charts A-L, including those compounds represented by formulas XLI, XLII, XLIII, XLIV, XLVI, XLVIII, XLIX, L, LI, LIII, LV, LVI, LVII, LIX, LX, LXIII, LXVI, LXIX, LXXXVI, LXXXVII, and LXXXVIII are frequently not isolated but used directly for a subsequent process step. When they are isolated, they are purified by methods known in the art, for example partition extraction, fractional crystalization, and, preferably, silica gel column chromatography.

The compounds of Charts A–L wherein Q, Q$_1$, or Q$_2$ are in either alpha or beta configuration, for example

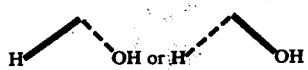

represent 15-α and 15-β isomers. The transformations shown herein generally have no effect on the stereochemistry at this position and therefore the final products have the same stero configuration at C-15 as in the starting materials at the corresponding carbon atoms. Should it be necessary to separate 15α and 15β isomers, this can be done by methods known in the art, for example by chromatography on neutral silica gel.

CHART K

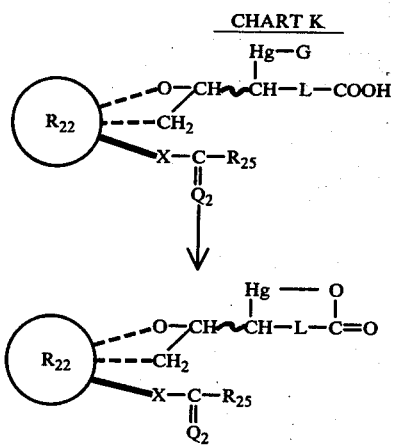

When an optically active intermediate or starting material is employed, subsequent steps yield optically active intermediates or products. That optical isomer of bicyclo lactone XXXVII is preferred which will yield product XL, for example, in the configuration corresponding to that of the naturally occurring prostaglandins. When the racemic form of the intermediate or starting material is employed, the subsequent intermediates or products are obtained in their racemic form. Optically active and racemic forms of the intermediates or starting materials are known or available by methods known in the art.

Compounds within the scope of formulas XXX-XXXIV, herein, occur in two isomeric forms wherein $\sim$ is in alpha or beta configuration, i.e. endo or exo relative to the heterocyclic ring. These two isomers differ in their mobility on TLC silica gel plates or on a silica gel column. The members of each pair of isomers are distinguished herein as "less polar" or "more polar" isomers, considering that mobility.

The lower alkanoates of the formula-XXX-to-XXXIV compounds disclosed herein are prepared from those compounds by replacing any blocking groups ($R_{40}$) with hydroxy, thereafter subjecting the hydroxy compound to a carboxyacylating agent, preferably the anhydride of a lower alkanoic acid, i.e., an alkanoic acid of 1 to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 2 to about 10 moles of anhydride per mole of the hydroxy compound reactant. The excess anhydride serves as a reaction diluent and solvent. An inert organic diluent, for example dioxane, can also be added. It is preferred to use at least enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride; with acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxylate is recovered from the diethyl ether extract by evaporation. The carboxylate is then purified by conventional methods, advantageously by chromatography.

Compounds within the scope of formulas XXX-XXXIV are transformed from one to another by methods known in the art. Accordingly, a compound wherein $R_{22}$ is

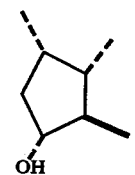

is transformed to another compound wherein $R_{22}$ is another ring within the scope of $R_{22}$, for example an 11-methylene compound, by methods known or described herein. A compound wherein the $C_{13}$-$C_{14}$ group is trans—CH=CH— is transformed to another compound wherein the $C_{13}$-$C_{14}$ group is cis—CH=CH—, —C≡C—, or —CH$_2$CH$_2$—. For example, —C≡C— is obtained by selective bromination and dehydrobromination. A compound wherein the $C_2$ substituent is —COOR, e.g. a methyl ester, is transformed by known methods to another compound having another $C_2$ substituent within the scope of $R_{30}$, as defined herein, for example —CH$_2$OH or

Chart N, herein, shows the steps of a process for preparing a 13,14-didehydro compound of formula XCVI, within the scope of the formula-XXXIV compounds above. The starting materials of formula XC are 15-oxo PGF type compounds known in the art or available by methods described herein or known in the art. For example see U.S. Pat. No. 3,728,382. It is immaterial whether 5,6-cis or 5,6-trans compounds are used as either one will ultimately yield the desired formula-XCVI compound.

CHART N

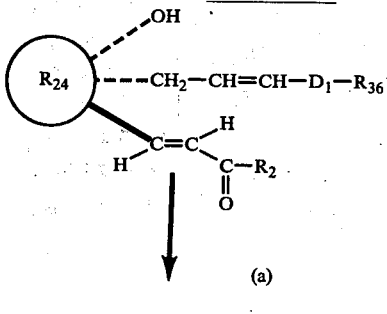

(a)

-continued
CHART N

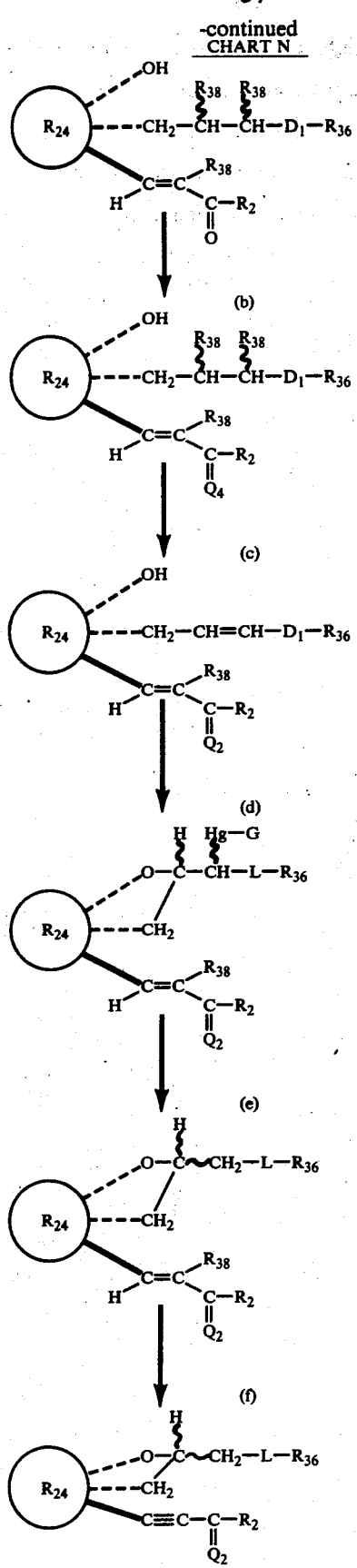

In the first step "a" of Chart N the formula-XCI trihalo compound is prepared, for example by reaction of the formula-XC compound with pyridinium hydrobromide perbromide in pyridine. Other halogenating agents are useful, e.g. N-bromo- or N-chloro-succinimide. Other tertiary amines are useful for the selective monodehydrohalogenation.

In step "b", the formula-XCII compound is obtained as a mixture of alpha and beta hydroxy isomers by reduction of XCI. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy) aluminum hydride, metal trialkoxy borohydrides, e.g., sodium trimethoxyborohydride, lithium borohydride, or diisobutyl aluminum hydride. For production of the preferred (15S) configuration prostacyclin derivatives, the alpha form of the formula-XCII compound is separated from the beta isomer by silica gel chromatography using methods known in the art.

In step "c" the C-5 and C-6 halogen atoms are removed by selective dehalogenation for example by contact with zinc in methanolic ammonium chloride, to yield the formula-XCIII monohalo compound. Other monohalo compounds within the scope of XCIII are known in the art. See for example U.S. Pat. No. 4,029,681. Such transformations as are optionally desired from $Q_4$ to $Q_2$ are readily made as known in the art or described herein.

In steps "d" and "e" the mercuration-demercuration cyclization described above is employed. See Chart J and accompanying description.

In step "f" the formula-XCV compounds are treated with a dehydrohalogenation reagent preferably potassium t-butoxide, to form the formula-XCVI compounds. The C-6 isomers are separated either after step "e" or "f".

Chart O, herein, shows the steps of a process for $\Delta^2$ analogs of formula C within the scope of the formula XXXIII and XXXIV compounds above.

$Q_5$, $Q_6$, $R_{41}$, and $R_{43}$ in Chart O, as defined in the TABLE herein, include silyl blocking groups as well as the tetrahydropyranyl blocking groups and others of $R_{40}$. The starting materials of formula XCVII are therefore available from compounds described above, optionally silylated by methods described herein or known in the art.

The formula-XCVIII compounds are obtained on selenenylation, and are then oxidized, with selenoxide elimination, to yield the formula-XCIX compounds. See H. J. Reich et al., J. Am. Chem. Soc. 97, 5434 (1975) as to reagents and conditions for these general reactions.

See also Fieser and Fieser, Reagents for Organic Synthesis, Vol. 6, pages 235 and 459, John Wiley, N.Y., 1977.

Substituted phenyl and naphthyl esters are prepared by methods known in the art. See for example U.S. Pat. No. 3,890,372. Phenacyl-type esters are likewise prepared by methods known in the art. See U.S. Pat. No. 3,979,440.

CHART O

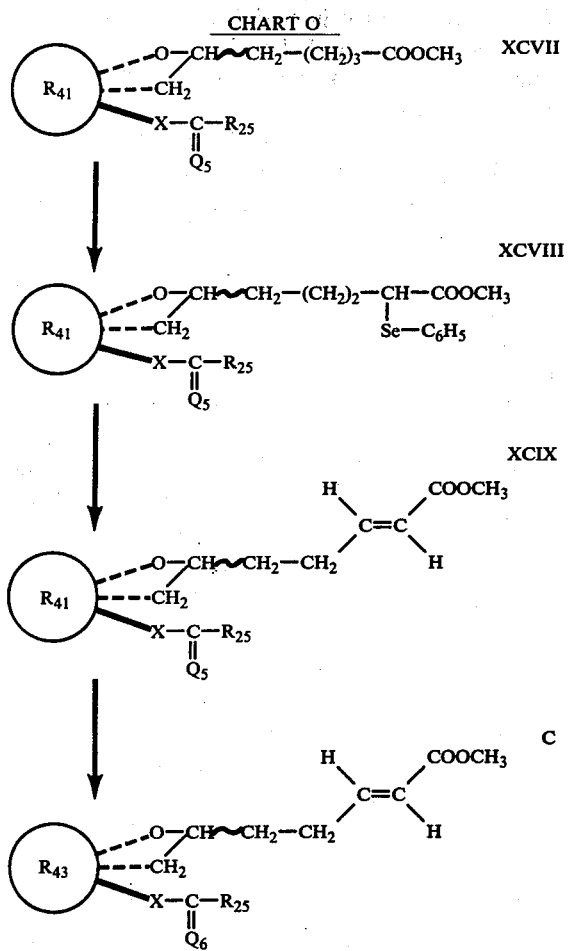

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60, or XL-100 spectrophotometer in deuterochloroform solutions with tetramethylsilane as an internal standard.

Mass spectra are recorded on a Varian Model MAT CH7 Mass Spectrometer a CEC Model 110B Double Focusing High Resolution Mass Spectrometer, or a LKB Model 9000 Gas. Chromatograph-Mass Spectrometer (ionization voltage 22 or 70 ev.), and are usually run as TMS (trimethylsilyl) derivatives.

"Brine", herein, refers to an aqueous saturated sodium chloride solution.

"Skellysolve B", herein, refers to mixed isomeric hexanes.

"TLC", herein, refers to thin layer chromatography.

Silica gel chromatography, as used herein, is understood to include elution, collection of fractions, and combination of those fractions shown by TLC to contain the desired product free of starting material and impurities.

"Concentrating", as used herein, refers to concentration under reduced pressure, preferably at less than 50 mm. and at temperatures below 35° C.

"Lower alkanoate", herein, refers to an ester of an alkanoic acid of 1 to 8 carbon atoms, inclusive.

"Drying", unless otherwise specified, is done by contacting the compound, in solution, with anhydrous sodium sulfate or magnesium sulfate, thereafter filtering off the solids.

"A-IX solvent system", used in thin layer chromatography, is made up from ethyl acetate-acetic acid-2,2,4-trimethylpentane-water (90:20:50:100) according to M. Hamberg and B. Samuelsson, J. Biol. Chem. 241, 247 (1966).

"E" and "Z", herein, follow J. E. Blackwood et al., J. Am. Chem. Soc. 90, 509 (1968).

"R" and "S", herein, follow R. S. Cahn, J. Chem. Ed. 41, 116 (1964).

The Jones reagent is sulfuric acid and chromic acid. See J. Chem. Soc. 39 (1946).

The Collins reagent is chromium trioxide in pyridine. See J. C. Collins et al., Tetrahedron Lett. 3363 (1968).

"Less polar" and "more polar", herein, refer to relative polarities of pairs of isomers as exhibited on thin layer chromatography or column chromatography.

PREPARATION 1

2-Decarboxy-2-amino-PGF Compounds

The following description is provided from a commonly-owned, prior-filed U.S. Patent Application which will be incorporated by reference when that application matures in an issued patent.

CHART M

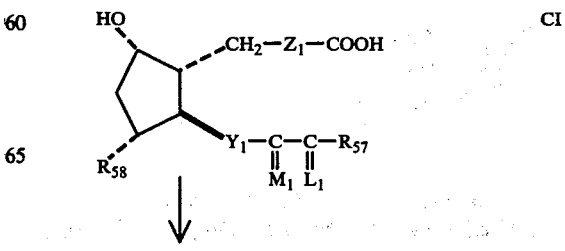

-continued
CHART M

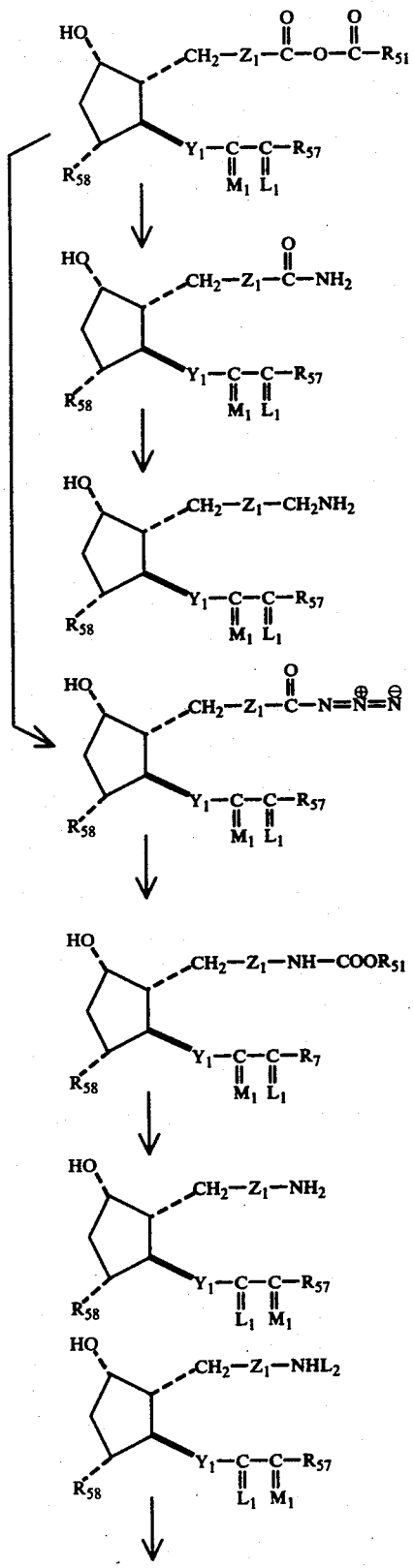

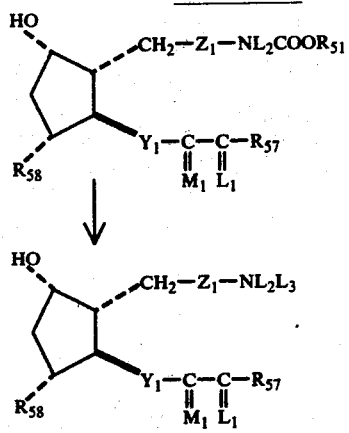

Chart M shows the steps by which the formula CI, $PGF_{2\alpha}$- or 11-deoxy-$PGF_{2\alpha}$-type free acid is transformed to the various 2-decarboxy-2-aminomethyl or 2-decarboxy-2-(substituted amino)methyl-$PGF_\alpha$- or 11-deoxy-$PGF_\alpha$-type compounds of formulas CIV, CVI, CVII, CVIII, CIX, or CX.

In Chart M,
$Y_1$ is trans—CH=CH—; —C≡C—, or —$CH_2CH_2$—;
$M_1$ is

wherein $R_{55}$ is hydrogen or methyl;
$L_1$ is

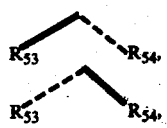

or a mixture of

wherein $R_{53}$ and $R_{54}$ are hydrogen, methyl, or fluoro, being the same or different, with the proviso that one of $R_{53}$ and $R_{54}$ is fluoro only when the other is hydrogen or fluoro;
$Z_1$ is (1) cis—CH=CH—$CH_2$—$(CH_2)_g$—$CH_2$—,
(2) cis—CH=CH—$CH_2$—$(CH_2)_g$—$CF_2$—,
wherein g is 1, 2, or 3;
$R_{57}$ is $$-(CH_2)_m-CH_3, \quad (1)$$

$$-O-\underset{}{\underset{}{\bigcirc}}-(T_1)_s \quad , \text{ or} \quad (2)$$

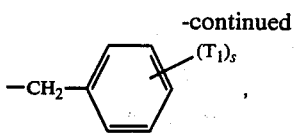

(3)

wherein *m* is 1 to 5, inclusive, $T_1$ is chloro, fluoro, trifluoromethyl, alkyl of 1 to 3 carbon atoms, inclusive, or alkoxy of 1 to 3 carbon atoms, inclusive, and *s* is 0, 1, 2, or 3, the various $T_1$'s being the same or different, with the proviso that not more than two $T_1$'s are other than alkyl, with the further proviso that $R_{57}$ is

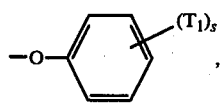

wherein $T_1$ and *s* are as defined above, only when $R_{53}$ and $R_{54}$ are hydrogen or methyl, being the same or different;

$R_{58}$ is hydrogen or hydroxy;

$L_2$ and $L_3$ are hydrogen, alkyl of 1 to 4 carbon atoms, inclusive, or —$COOR_{51}$, wherein $R_{51}$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted 1, 2, or 3 chloro or alkyl of 1 to 3 carbon atoms, inclusive; being the same or different, with the proviso that not more than one of $L_2$ and $L_3$ is —$COOR_{51}$.

By the procedure of Chart M the formula CI compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type, amide or formula CV PG-type, azide.

For preparation of the $PGF_{2\alpha}$-type, amide (formula CIII) the formula CII mixed acid anhydride is reacted with liquid ammonia or ammonium hydroxide.

Alternatively, the formula CIII compound is prepared from the formula CI free acid by methods known in the art for transformation of carboxy acids to corresponding carboxyamides. For example, the free acid is transformed to a corresponding methyl ester (employing methods known in the art; e.g., excess etheral diazomethane), and a methyl ester thus prepared is transformed to the formula CIII amide.

Thereafter the formula CIV 2-decarboxy-2-aminomethyl-$PGF_{2\alpha}$- or 11-deoxy-$PGF_{2\alpha}$-type compound is prepared from the formula CIII compound by carbonyl reduction. Methods known in the art are employed in this transformation. For example, lithium aluminum hydride is conveniently employed.

The formula CII compound is alternatively used to prepare the formula CV azide. This reaction is conveniently carried out employing sodium azide by methods known in the art. See for example, Fieser and Fieser, Reagents for Organic Synthesis vol. 1, pgs. 1041–1043, wherein reagents and reaction conditions for the azide formation are discussed.

Finally, the formula CVI urethane is prepared from the formula CV azide reaction with an alkanol, aralkanol, phenol, or substituted phenol. For example, when methanol is employed the formula CVI compound is prepared wherein $R_1$ is methyl. This formula CVI PG-type product is then employed in the preparation of either the formula CVII or CVIII product.

In the preparation of the formula CVII primary amine from the formula CVI urethane, methods known in the art are employed. Thus, for example, treatment of the formula CVII urethane with strong base at temperatures above 50° C. are employed. For example, sodium, potassium, or lithium hydroxide is employed.

Alternatively, the formula CVI compound is employed in the preparation of the formula CVIII compound. Thus, when $L_1$ is alkyl the formula CVIII compound is prepared by reduction of the formula CVI urethane wherein $R_1$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) with an alkyl chloroformate. The reaction thus proceeds by methods known in the art for the preparation of carbamates from corresponding secondary amines. Finally, the formula CX product wherein $L_2$ and $L_3$ are both alkyl is prepared by reduction of the formula CIX carbamide. Accordingly, methods hereinabove described for the preparation of the formula CVIII compound from the formula CVI compound are used.

PREPARATION 1A

2-Decarboxy-2-azidomethyl-$PGF_{2\alpha}$ (1) A solution of t-butyldimethylsilyl chloride (10 g.), imidazole (9.14 g.), and $PGF_{2\alpha}$(3 g.) in 12 ml. of dimethylformamide are magnetically stirred under nitrogen atmosphere for 24 hr. The resulting mixture is then cooled in an ice bath and the reaction quenched by addition of ice water. The resulting mixture is then diluted with 150 ml. of water and extracted with diethyl ether. The combined ethereal extracts are then washed with water, saturated ammonium chloride, a sodium chloride solution, and thereafter dried over sodium sulfate. Solvent is removed under vacuum yielding $PGF_{2\alpha}$, t-butyldimethylsilyl ester, 9,11,15-tris-(t-butyldimethylsilyl ether).

NMR absorptions are observed at 0.20, 0.30, 0.83, 0.87, 0.89, 1.07-2.50, 3.10-4.21, and 5.38 $\delta$.

Characteristic infrared absorptions are observed at 970, 1000, 1060, 1250, 1355, 1460, 1720, and 2950 cm.$^{-1}$.

(2) To a magnetically stirred suspension of lithium aluminum hydride (7.75 g.) in 18 ml. of diethyl ether is added dropwise at room temperature over a period of 12 min. 8.71 g. of the reaction product of part (1) above in 40 ml. of diethyl ether. After stirring at ambient temperature for 1 hr., the resulting product is cooled in an ice water bath and saturated sodium sulfate is added dropwise until the appearance of a milky suspension. The resulting product is coagulated with sodium sulfate, triturated with diethyl ether, and the solvent is removed by suction filtration. Concentration of the diethyl ether under vacuum yields 7.014 g. of 2-decarboxy-2-hydroxymethyl-$PGF_{2\alpha}$, 9,11,15-tris-(t-butyldimethylsilyl ether).

NMR absorptions are observed at 0.03, 0.82, 0.87, 1.10-2.60, 3.30-4.30, and 5.37 $\delta$.

Characteristic infrared absorptions are observed at 775, 840, 970, 1065, 1250, 1460, 2895, 2995, and 3350 cm.$^{-1}$.

(3) p-Toluenesulfonyl chloride (3.514 g.), pyridine (44 ml.), and the reaction product of subpart (2), 7.014 g., are placed in a freezer at −20° C. for 3 days. Thereafter, 7.200 g. of 2-decarboxy-2-p-toluene-sulfonyloxymethyl-PGF$_{2\alpha}$, 9,11,15-tris-(t-butyldimethylsilyl ether), is recovered.

NMR absorptions are observed at 0.10, 0.94, 0.97, 1.10, 2.50, 2.50, 4.03, 3.80-4.80, 5.45, 7.35, and 7.80 δ.

Infrared absorptions are observed at 775, 970, 1180, 1190, 1250, 1360, 1470, 2900, and 2995 cm.$^{-1}$.

(4) The reaction product of subpart (3) (2.13 g.) is placed in 42 ml. of acetic acid, tetrahydrofuran, and water (3:1:1) containing 0.25 ml. of 10 percent aqueous hydrochloric acid. The reaction mixture becomes homogeneous after vigorous stirring for 16 hr. at room temperature. The resulting solution is then diluted with 500 ml. of ethyl acetate; washed with saturated sodium chloride and ethyl acetate; dried over sodium sulfate; and evaporated under reduced pressure, yielding 1.301 g. of an oil. Crude product is chromatographed on 150 g. of silica gel packed with ethyl acetate. Eluting with ethyl acetate yields 0.953 g. of 2-decarboxy-2-p-toluenesulfonyloxymethyl-PGF$_{2\alpha}$.

(5) The reaction product of subpart (4), (0.500 g.) in 5.0 ml. of dimethylformamide was added to a stirred suspension of sodium azide (1.5 g.) in 20 ml. of dimethylformamide. Stirring is continued at ambient temperature for 3 hr. The reaction mixture is then diluted with water (75 ml.), extracted with diethyl ether (500 ml.), and the etheral extracts washed successively with water, saturated sodium chloride, and dried over sodium sulfate. Removal of the diethyl ether under reduced pressure yields 0.364 g. of 2-decarboxy-2-azidomethyl-PGF$_{2\alpha}$. A characteristic azido infrared absorption is observed at 2110 cm.$^{-1}$.

PREPARATION 1B

2-Decarboxy-2-aminomethyl-PGF$_{2\alpha}$ (Formula CXXV).

Crude decarboxy-2-azidomethyl-PGF$_{2\alpha}$ (Prep. 1A, 0.364 g.) in 12 ml. of diethyl ether is added to a magnetically stirred suspension of lithium aluminum hydride (0.380 g.) in 20 ml. of diethyl ether. Reaction temperature is maintained at about 0° C. and addition of lithium aluminum hydride proceeds dropwise over a 4 min. period. After addition is complete, the resulting mixture is stirred at ambient temperature for 1.5 hr. and thereafter placed in an ice both (0°-5° C.). Excess reducing agent is then destroyed by addition of saturated sodium sulfate. After cessation of gas evolution, the resulting product is coagulated with sodium sulfate, triturated with diethyl ether, and solid salts removed by filtration. The filtrate is then dried with sodium sulfate, and evaporated under reduced pressure to yield 0.304 g. of a slightly yellow oil. This oil (100 mg.) is then purified by preparative thin layer chromatography, yielding 42 g. of title product. NMR absorptions are observed at 0.90, 1.10-2.80, 3.28, 3.65-4.25, and 5.45 δ. Characteristic infrared absorptions are observed at 970, 1060, 1460, 2995, and 3400 cm.$^{-1}$. The mass spectrum shows parent peak at 699.4786 and other peaks at 628, 684, 595, 217, and 274.

PREPARATION 2

14-Bromo-PGF$_{2\alpha}$, Methyl Ester (Formula XCIII) and 14-Bromo-(15R)-PGF$_{2\alpha}$, Methyl Ester I. Refer to chart N. The formula-XCI 5ξ,6ξ,14-bromo-15-keto-PGF$_{1\alpha}$, methyl ester (U.S. Pat. No. 3,728,382, 3.38 g.) in about 25 ml. of pyridine is treated dropwise with a solution of pyridinium hydrobromide perbromide (7.08 g.) in 35 ml. of pyridine over 2.25 hr. Thereafter the mixture is stirred for 27 hr., diluted with ether and filtered. The filtrate is washed with water, cold hydrobromic acid (5%) aqueous sodium bicarbonate (5%), then dried and concentrated to yield 3.72 g. product. Similarly an additional 1.06 g. is prepared and combined. The product is subjected to silica gel chromatography eluting with hexane-ethyl acetate (65:35) to yield XCI, 2.83 g., having NMR peaks at 0.90, 1.1-2.58, 2.58-3.4, 3.4-3.88, 3.67, 3.88-4.61, 6.96, and 7.03δ; infrared peaks at 3400, 1730, 1685, 1610, 1245, 1200, 1170, 1085, and 1050 .cm$^{-1}$; and mass spectral peaks (TMS) at 746.0562, 636, 634, 632, 630, 555, 553, and 551.

There is also obtained, as a separate fraction from the chromatography of the reaction product, 5ξ-bromo-9-deoxy-6ξ,9-epoxy-14-bromo-15-keto-PGF$_{1\alpha}$, methyl ester, 0.93 g., having NMR peaks at 0.90, 1.10-3.30, 3.03-3.46, 3.65, 3.78-5.0, 6.91 and 7.00 δ; infrared peaks at 3480, 2880, 2810, 1735, 1690, 1615, 1245, 1200, 1175, 1150, and 1080 cm$^{-1}$; and mass spectral peaks (TMS) at 594.099, 515, and 478.

II. 5ξ,6ξ,14-Tribromo-PGF$_{1\alpha}$, methyl ester (XCII). A solution of XCI (2.38 g.) in 20 ml. of methanol is added to a solution of sodium borohydride (1.28 g.) in 40 ml. of methanol at −35° C. The temperature is held at −25° C. for 1 hr. The mixture is diluted with diethyl ether and quenched with acetic acid. The solution is washed with saline solution (5%) and aqueous bicarbonate (5%) solutions, dried, and concentrated to a mixture of C-15 epimers (XCII). Separation is achieved by silica gel chromatography eluting with hexane-ethyl acetate (3:2 followed by 1:1) to yield, first, the 15R epimer, 1.57 g. having NMR peaks at 0.9, 1.1-3.35, 3.35-4.65, 3.66, and 5.57-6.21 δ; infrared peaks at 3380, 1735, 1725, 1250, 1200, 1175, 1075, and 1050 cm$^{-1}$; high resolution mass spectral peak (TMS derivative) at 749.0362, and [α]$_D$-11° in ethanol; and second, the 15S epimer 0.605 g. having NMR peaks at 0.9, 1.10-3.35, 3.35-4.6, 3.66, and 5.65-6.15 δ; infrared peaks at 3380, 1740, 1650, 1435, 1250, 1200, 1175, 1120, 1080, and 1045 cm$^{-1}$; high resolution mass spectral peak (TMS derivative) at 749.0384; and [α]$_D$-4° in ethanol.

III. 14-Bromo-PGF$_{2\alpha}$, methyl ester. A solution of the 15S isomer (0.60 g.) in 20 ml. of methanol is treated with ammonium chloride (0.11 g.) and zinc dust (0.28 g.). The mixture is stirred for 1.5 hr., diluted with benzene and filtered. The filtrate is washed with 0.2 M. potassium acid sulfate, dried, and concentrated to yield 0.37 g., having R$_f$ 0.26 (TLC on silver nitrate-treated silica gel in ethyl acetate); NMR peaks at 0.88, 1.1-2.71, 2.71-3.55, 3.66, 3.80-4.35, 5.23-5.56 and 5.84 δ; and infrared peaks at 3320, 2900, 2820, 1940, 1650, 1430, 1310, 1240, 1215, 1170, 1115, and 1030 cm$^{-1}$.

Following the procedures of III but employing the 15R epimer of II, there is likewise obtained 14-bromo-(15R)-PGF$_{2\alpha}$, methyl ester.

EXAMPLE 1

9-Deoxy-6ξ,9α-epoxy-2,3,4-trinor-PGF$_1$, Ethyl Ester, Mixed Isomers (Formula III).

1. Refer to Chart A. There are first prepared the formula-XXXIX 9-deoxy-6ξ,9α-epoxy-2,3,4-trinor-PGF$_1$ethyl ester, bis tetrahydropyranyl ether, mixed isomers. A solution of triethyl phosphonoacetate (3.58 g.) in 40 ml. of tetrahydrofuran is treated at 0° C. with a solution of potassium t-butoxide (1.79 g.) in 40 ml. of tetrahydrofuran, followed by a solution of the formula-XXXVIII 2α,4α-dihydroxy-5β-(3'α-hydroxy-1'-trans-octenyl)-α-cyclopentylacetaldehyde-γ-lactol, 3'4-bis-tetrahydropyran-2-yl ether (E. J. Corey et al., J. Am. Chem. Soc. 92, 397 (1970), (5.6 g.)) in 20 ml. of benzene added over a 1-minute period. Thereafter the mixture is stirred at 0–25° C. for 25 min. and diluted with 500 ml. of ether-methylene chloride (3:1). The resulting mixture is washed with water, dilute potassium hydroxide solution, water, and brine, dried, and concentrated to the formula-XXXIX compound in a crude product, 8.1 g.

The above product is subjected to silica gel chromatography, eluting with 40–75% ethyl acetate in Skellysolve B, to obtain the formula-XXXIX bis tetrahydropyranyl ether 4.7 g., having NMR peaks at 5.4-5.7, 3.2-4.8, 2.42 and 2.56 δ.

II. The above mixed isomers of the formula-XXXIX compound (1.0 g.) are hydrolyzed in 15 ml. of acetic acid and 7.5 ml. of water at 37°–39° C. for 3 hr. The mixture is cooled, mixed with diethyl ether-methylene chloride (3:1), and shaken with ice-cold dilute potassium hydroxide solution. The organic phase is washed with brine, dried, and concentrated. The residue is subjected to silica gel chromatography, eluting with 0-5% ethanol in ethyl acetate, to obtain the formula-III title compound as mixed less polar and more polar isomers, 0.55 g., having NMR peaks at 5.27-5.47, 3.3-4.5, 2.4, and 2.52 δ; and mass spectral peaks at 322, 304, 278, 251, and 235.

EXAMPLE 2

9-Deoxy-6 86,9α-epoxy-2,3,4-trinor-PGF$_1$, Ethyl Ester, Bis(tetrahydropyran-2-yl ether), mixed isomers (Formula XXXIX wherein R$_{40}$ of Q$_1$ and R$_{21}$ is THP (tetrahydropyran-2-yl); and
9-Deoxy-6,9α-epoxy-2,3,4-trinor-PGF$_1$, Ethyl Ester, less polar isomer and more polar isomer (Formula III wherein R$_4$ of Q and W is hydrogen).

1. Refer to Chart A. There is first prepared the formula-XXXIX bis(tetrahydropyranyl ether). A mixture of the formula-XXXVIII 2α,4α-dihydroxy-5β-[(3S)-3-hydroxy-trans-1-ocentyl]-1α-cyclopentane acetaldehyde, γ-lactor, bis-(tetrahydropyran-2-yl ether) (10 g.), ethyl (triphenylphosphoranylidine)acetate (10 g.) and 150 ml. of ethanol is stirred for 3 days under nitrogen. The mixture is then concentrated and the residue is chromatographed on silica gel, eluting with ethyl acetate-Skellysolve B (1:1) to yield the formula-III mixed isomer title compound, 9.0 g. The product has R$_f$ 0.34 and 0.39 for the mixture (TLC on silica gel in ethyl acetate-hexane (1:3)), and NMR peaks at 5.35-5.69, 4.69, 3.98-4.34, and 2.48-2.62 δ.

II. To remove the THP blocking groups, a mixture of the above formula-XXXIX compound (6.95 g.), 100 ml. of acetic acid, 50 ml. of water, and 10 ml. of tetrahydrofuran is stirred at 40° C. for 4 hr. The mixture is cooled, diluted with 500 ml. of ethyl acetate and washed with a mixture of 72 g. of sodium hydroxide in 500 ml. of ice and water, then with brine, dried, and concentrated. The residue is chromatographed on a column of 500 g. of fine silica gel (40-63 μ, Merck) previously deactivated with acetone-methylene chloride (60:40). The column is eluted with acetone-methylene chloride mixtures as follows: 3 liters of 30:70, 0.5 liter of 35:65, and 1.5 liter of 40:60. The first 500 ml. of eluant is discarded, and thereafter 40 ml. fractions are collected. Fractions 40–46 yield the formula-III less polar isomer of the title compound, 0.21 g., having R$_f$ 0.39 (TLC on silica gel in acetone-methylene chloride (40:60)), and NMR peaks at 5.43-5.54, 3.98-4.33, and 2.57-2.71 δ. See FIG. 1 for the $^1$H NMR spectrum. Fractions 47-62 yield a mixture of the isomers. Fractions 63-100 yield the formula-III more polar isomer of the title compound, 2.03 g., having R$_f$ 0.32 (TLC on silica gel in acetone-methylene chloride (40:60)), and NMR peaks at 5.47-5.58, 4.34-4.64, 3.98-4.34, and 2.48-2.63. See FIG. 2 for the $^1$H NMR spectrum, noting peaks at 4.4-4.6 δ for this more polar isomer.

The formula-III less polar isomer is named (6S)-2,3,4-trinor-PGI$_1$, ethyl ester. The more polar isomer is named (6R)-2,3,4-trinor-PGI$_1$, ethyl ester.

EXAMPLE 3

9-Deoxy-6,9α-epoxy-2,3,4-trinor-PGF$_1$, Methyl Ester, Bis(tetrahydropyran-2-yl Ether), mixed isomers (Formula XXXIX); and
9-Deoxy-6,9α-epoxy-2,3,4-trinor-PGF$_1$, Methyl Ester, less polar isomer and more polar isomer (Formula III).

1. Refer to Chart A. A solution of trimethylphosphonoacetate (7.11 g.) in 75 ml. of tetrahydrofuran is treated at 0° C. with a solution of potassium t-butoxide (4.05 g.) in 75 ml. of tetrahydrofuran. The mixture is stirred at 0°-5° for 10 min. and then a solution of 2α,4α-dihydroxy-5β-[(3S)-3-hydroxy-trans-1-ocetenyl]-1α-cyclopentane acetaldehyde, γ-lactol, bis(tetrahydropyran-2-yl ether) (13.2 g.) in 60 ml. of tetrahydrofuran is added within 1 min. Thereafter the mixture is stirred at about 25° C. for 2 hr., then diluted with 600 ml. of diethyl ether-methylene chloride (3:1). The organic phase is washed with brine, dried, and concentrated. The residue is chromatographed on silica gel, eluting with ethyl acetate-Skellysolve B (1:1), to yield the formula-XXXIX product as mixed C-6 isomers, 12.15 g., having R$_f$ 0.62 (TLC on silica gel in ethyl acetate-hexane (1:1)), and NMR peaks at 5.33-5.71, 4.71, 3.67, and 2.5-2.61 δ.

II. To prepare the formula-III product, a mixture of the above formula-XXXIX bis (tetrahydropyran-2-yl ether) (12.15 g.) in 200 mL. of acetic acid, 100 mL. of water, and 10 mL. of tetrahydrofuran is stirred at 40° C. for 4 hr. The mixture is cooled and diluted with 800 mL. of cold (−10° C.) ehtyl acetate. The organic phase is washed with a mixture of sodium hydroxide (150 g.) in 800 mL. of ice and water, then with brine, dried, and concentrated. The residue, 11.8 g.) is chromatographed on a column of about 500 g. o fine silica gel (40–63 μ, Merck). The column is eluted with acetone-methylene chloride mixtures as follows: 8 liters of 40:60, and 4 liters of 60:40. The first 2 liters of eluant is discarded, thereafter 17 200 ml. fractions and 18 300 ml. fractions are collected. Fractions 6–22 yield a mixture of the formula-III les polar isomer and more polar isomer, 3.9 g., later separated below. Fractions 23–32 yield the formula-III more polar isomer of the title compound, 3.55 g.

Rechromatography of the mixed-isomer fraction, again on fine (40-63 μ) silica gel, followed by further rechromatography of a mixed-isomer fraction so-obtained, yields the less polar isomer and more polar isomer which, with the amounts above, total: for the less polar isomer, 1.25 g., and for the more polar isomer 5.44 g.

The formula-III less polar isomer of the title compound has m.p. 47°-48° C. (from diethyl either-hexane), $R_f$ 0.41 (TLC on silica gel in acetone-methylene chloride (40:60)); NMR peaks at 5.50-5.61, 3.86-4.46, 3.72, and 2.61-2.75 δ; and mass spectral peaks at 470.2898, 455, 439, 399, 380, 265, 219, 199, and 173 (TMS derivative).

The formula-III more polar isomer has $R_f$ 0.35 (TLC on silica gel in acetone-methylene chloride (40:60)); NMR peaks at 5.50-5.61, 3.88-4.67, 3.72, and 2.52-2.63 δ; and mas spectral peaks at 470.2903, 455, 399, 380, 309, 199, and 173 (TMS derivative).

The formula-III less polar isomer is named (6S)-2,3,4-trinor-PGI$_1$, methyl ester. The more polar isomer is named (6R)-2,3,4-trinor-PGI$_1$, methyl ester.

EXAMPLE 4

9-Deoxy-6ξ,9α-epoxy-2,3,2-trinor-PFG$_1$, Methyl Ester, Bis(tetrahydropyran-2-yl ester), Mixed Isomers, by Michael Addition.

I. There is first prepared 2,3,4-trinor-5,6-trans-didehydro-PFG$_{1\alpha}$, methyl ester, 11,15-bis(tetrahydropyran-2-yl ester). A mixture of 2α, 4α-dihydroxy-5β-[(3S)-3-hydroxy-trans-1-octenyl]-1α-cyclopentaneacetaldehyde, γ-lactol, bis(tetrahydropyran-2-yl ether) (8.8 g.) methyl-(triphenylphosphoranylidene)acetate (10.0 g.) and 100 ml. of tetrahydrofuran is stirred until homogenous and then left at about 25° C. for 7 days. The mixture is concentrated. The residue is chromatographed on silica gel deactivated with ethyl acetate, eluting with ethyl acetate-Skellysolve B (1:1) to yield the above 5,6-trans compound, 9.6 g., having $R_f$ 0.59 (TLC on silica gel in ethyl acetate-hexane (1:1)); NMR peaks at 6.80-7.20, 5.77-6.01, 5.38-5.67, 4.71, and 3.70 δ; and infrared absorption at 3600, 1730, and 1670 cm$^{-1}$.

II. To prepare the title compound, a solution of the above 5,6-trans compound (0.300 g.) in 3 ml. of methanol and approximately 0.15 ml. of a methanol solution of sodium methoxide is stirred for 25 min., whereupon the reaction is complete as shown by TLC. The mixture is diluted with 35 ml. of diethyl ether, washed with brine, dried over magnesium sulfate, and concentrated. The oily residue, 0.290 g., consists of the mixed isomers of the formula-XXXIX title compound, having identical properties to those reported above in Example 3.

EXAMPLE 5

3,3aβ,4,5,6,6aβ-Hexahydro-5α-hydroxy-2ξ-(2'-hydroxyethyl)-4β-(3'α-hydroxy-trans-1-octenyl)2H-cyclopenta[b]furan, 3',5'-bistetrahydropyranyl Ether Mixed Isomers (Formula-XLI: Q$_1$ is

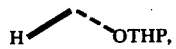

R$_2$ is n-pentyl, (R$_{21}$) is

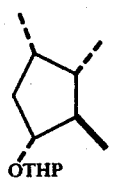

where THP id tetrahydropyranyl, and ~ is alpha and beta).

Refer to Chart B. A solution of formula-XXXIX, 9-deoxy-6ξ,9α-epoxy-2,3,4-trinor-PGF$_1$, ethyl ester, bistetrahydropyran-2-yl ether (Example 1-I, 4.0 g.) in 40 ml. of diethyl ether is added to a slurry of lithium aluminum hydride (0.05 g.) in 100 ml. of anhydrous diethyl ether. The mixture is heated at reflux with stirring, for 2 hr. After cooling it is treated succesively with 0.70 ml. of water, 0.70 ml. of 15% aqueous sodium hydroxide solution and 0.8 ml. of water. The mixture is filtered and the filtrate is concentrated to yield the formula XLI title compounds, 3.7 g., having NMR peaks at 5.2-5.6, 4.6, and 3.0-4.0 δ. An alternate name for these compounds is {3aR-[3α,4α(1E,3S*), 5β,6aα]{-hexahydro-5-[(tetrahydro-2H-pyran-2-yl)oxy]-4-{3-[(tetrahydro-2H-pyran-2-yl)oxy]-1-octenyl}-2H-cyclopenta[a]furan-2ξ-ethanol, where ξ indicates unknown configuration.

EXAMPLE 6

3,3aβ,4,5,6,6aβ-Hexanhydro-5α-hydroxy-2ξ-(formylmethyl)4β-(3'α-hydroxy-trans-1-octenyl)-2H-cyclopenta[b]furan, 3',5-bistetrahydropyran-2-yl Ether Mixed Isomers, (Formula-XLII: Q$_1$ is

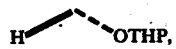

R$_2$ is n-pentyl, (R$_{22}$) is

where THP is tetrahydropyranyl, and ~ is alpha and beta); and

9-Deoxy-3,4,-trans-didehydro-6ξ,9α-epoxy-2-nor-PGF$_1$, Ehtyl Ester, Bistetrahydropyranyl Ether Mixed Isomers (Formula-XLIII: A is a valence bond, Q$_1$ is

$R_1$ is ethyl ($R_2$) is

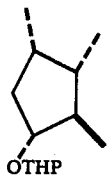

where THp is tetrahydropyranyl, and ~ is alpha and beta).

I. Refer to Chart B. A solution of the formula-XLI 3,3aβ,4,5,6,6aβ-hexahydro-5α-hydroxy-2ξ-(2'-hydroxyethyl)-4β-(3'α-hydroxy-trans-1-octenyl)-2H-cyclopenta[b]furan, 3',5-bistetrahydropyran-2-yl ether (Example 5, 2.3 g.) in 15 ml. of dichloromethane is added (in 15 sec.) to a solution of chromium trioxide (3.8 g.) in 100 ml. of dichloromethane and 6 ml. of pyridine. The mixture is stirred at 15° C. for 10 min., then 25 ml. of benzene is added and the mixture filtered. The filrate and washings are concentrated to about 15 ml. and taken up in 50 ml. of dichloromethane. The mixture is contacted with CC-4 silica gel (Mallinckrodt SilicAR ®) and diatomaceous earth and filtered. The filtrate is concentrated to yield the formula-XLII title aldehyde, as mixed isomers.

II. A solution of the above formula-XLII aldehyde in 10 ml. of benzene is cooled to 10° C. and added to a previously prepared mixture of 1.1 ml. of triethyl phosphonoacetate and 0.60 g. of potassium t-butoxide in 30 ml. of tetrahydrofuran which has been stirred at 0° C. for 10 min. Thereupon the ice-bath is removed and the mixture stirred for 30 min. as it gradually warms to about 25° C. Finally the mixture is diluted with diethyl ether-methylene chloride (3:1) and shaken with water. The organic phase is washed with dilute aqueous potassium hydroxide, water, and brine, dried, and concentrated to a residue, 3.8 g. The residue is subjected to silica gel chromatography, eluting with ethyl acetate-Skellysolve B (1:1), to yield the formula-XLIII title compound mixed less polar and more polar isomers, 2.3 g., having NMR peaks at 5.4–7.2, 4.7, and 3.2–4.5 δ.

EXAMPLE 7

9-Deoxy-3,4-trans-didehydro-6ξ,9α-epoxy-2-nor PGF₁, Ethyl Ester Mixed Isomers (Formula V: $C_gH_{2g}$ is trimethylene, Q is

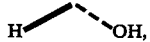

$R_1$ is ethyl, $R_5$ and $R_6$ are hydrogen, W is

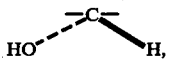

and ~ is alpha and beta.

The formula-XLIII bis(tetrahydropyranyl ether) (Example 6–11, 0.5 g.) is hydrolyzed in a mixture of 12 ml. of acetic acid and 6 ml. of water at 37°–39° C. for 2.5 hr. The mixture is cooled and shaken with diethyl ether-di-chloromethane (3:1) and a mixture of cold brine and aqueous potassium hydroxide. The organic phase is washed with brine, dried and concentrated. The residue is subjected to silica gel chromatography, eluting with 0–5% ethanol in ethyl acetate to yield the formula-V title compounds 0.29 g., having NMR peaks at 5.7, 5.97, 6.68–7.28, 5.32–5.57, and 3.4–4.5 δ; and mass spectral peaks (for the TMS derivatives) at 510, 495, 481, 465, 429, 420, 411, 397, and 349.

The principle product is the more polar isomer and is named (3E,6S)-2-nor-Δ³-PGI₁, ethyl ester. The less polar isomer is named (E,6R)-2-nor-Δ³-PGI₁, ethyl ester.

EXAMPLE 8

9-Deoxy-6ξ,9α-epoxy-2-nor PGF₁, Methyl Ester, Mixed Isomers (Formula IV: $C_gH_{2g}$ is trimethylene, d is 2, Q is

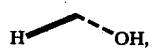

$R_1$ is methyl, $R_5$ and $R_6$ are hydrogen, W is

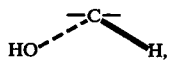

and ~ is alpha and beta.

Refer to Chart B. The acid form of the formula-XLIII compound is first prepared. A mixture of the formula-XLIII 9-deoxy-3,4,-trans-didehydro-6ξ,9α-epoxy-2-nor-PGF₁, ethyl ester, bistetrahydropyran-2-yl ether (Example 8, 1.7 g.) and 15 ml. of methanol is treated with a solution of 0.25 g. of sodium hydroxide in 6 ml. of water. The mixture is stirred at about 25° C. for 5 hr. Chipped ice is added and the mixture shaken with diethyl ether-dichloromethane (3:1) and cold dilute hydrochloric acid to acidify. The organic phase is washed with brine, dried, and concentrated to yield the formula-XLIII acid, as mixed isomers.

The acid above is dissolved in aqueous sodium hydroxide (0.2 g. in 25 ml. of water) and the resulting solution adjusted to pH 9 with dilute hydrochloric acid. Following the procedure of Dennis et al., Tetrahedron Lett. 1821 (1968), this solution is treated with a freshly prepared mixture of nickle chloride hexahydrate (0.30 g.) and potassium cyanide (0.41 g.) in 25 ml. of water followed by a fresh solution of sodium borohydride (1.0 g.) in 5.0 ml. of water. The mixture is stirred at about 25° C. for 16 hr. and then cooled in an ice bath while acidifying with cold dilute hydrochloric acid to pH 1.–2. (Danger: evolution of hydrogen and hydrogen cyanide). The resulting mixture is immediately extracted with diethyl ether-dichloromethane (3:1) and the organic phase is washed with dilute acid, water, and brine, dried, and concentrated to the acid form of the formula-XLIV bistetrahydropyran-2-yl ether, as mixed isomers.

The above formula-XLIV acid is converted to the methyl ester by treatment in diethyl ether solution with diazomethane, thereafter separating the formula-XLIV methyl ester, bistetrahydropyran-2-yl ether, having NMR peaks at 5.3–5.6, 4.63, 3.61, and 3.2–4.5 δ.

The above formula-XLIV methyl ester, bistetrahydropyran-2-yl ether is hydrolyzed to the title compound in 25 ml. of acetic acid and 12.5 ml. of water at 37°–40° C. for 2.5 hr. Thereafter the product is worked up as for Example 7 and subjected to silica gel chromatography, eluting with 4–5% ethanol in ethyl acetate. There is finally obtained the formula-IV title product, as mixed less polar and more polar isomers, 0.200 g., having NMR peaks at 5.32–5.7, 3.61 and 3.3–4.5 δ; and mass spectral peaks at 336,322, 292, and 264.

The principle product is the more polar isomer and is named (6S)-2-nor-PGI$_1$, methyl ester.

EXAMPLE 9

9-Deoxy-3,4,-cis-didehydro-6ξ,9α-epoxy-PGF$_1$, Bistetrahydropyran-2-yl Ether, Mixed Isomers (Formula XLIII: A is methylene, Q$_1$ is

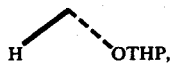

R$_2$ is n-pentyl, R$_1$ is hydrogen, (R$_2$) is

and ~ is alpha and beta; 9-Deoxy-6ξ,9α-epoxy-PGF$_1$, Mixed Isomers (Formula IV: C$_g$H$_{2g}$ is trimethylene, d is 3, Q is

R$_1$ is hydrogen, R$_5$ and R$_6$ are hydrogen, W is

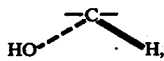

and ~ is alpha and beta); and
9-Deoxy-6ξ,9α-epoxy-PGF$_1$, Ethyl Ester, Mixed Isomer (Formula IV as above except that R$_1$ is ethyl).

I. Refer to Chart B. A mixture of the formula-XLII aldehyde, namely 3,3aα,4,5,6,6aα-hexahydro-5α-hydroxy-2ε-(formylmethyl)-4β-(3'α-hydroxy-trans-1-octenyl)2H-cyclopenta-[b]furan, 3'5-bistetrahydropyran-2yl ether (Example 6-1, equivalent of 4.64 g.) and (2-carboxyethyl)triphenylphosphonium chloride (see Howard S. Corey, Jr. et al., J. Am. Chem. Soc, 86, 1884 (1964), 3.71 g.) in dimethylsulfoxide-tetrahydrofuran (1:1) is added under nitrogen, with stirring, to a slurry of sodium hydride (0.84 g. of 57%) in the same solvent system. The reaction is monitored by TLC and after about 6 hr. water is added and the mixture extracted with diethyl ether. The aqueous layer is mixed with a suspension of ammonium chloride (5 g.) in 25 ml. of brine and the mixture is extracted with ethyl acetate. The organic phase is washed with brine, dried with magnesium sulfate, and concentrated. The residue is subjected to silica gel chromatography, eluting with ethyl acetate (25–50%)-hexane to yield the formula-XLIII title compound, as mixed isomers.

II. The formula-XLIII compound above is reduced in ethyl acetate solution with hydrogen at slightly above atmospheric pressure in the presence of 5%-palladium-on-carbon catalyst. The reaction is terminated when one equivalent of hydrogen has been taken up. The catalyst is filtered off and the formula-XLIV compound recovered, as mixed isomers.

III. Following the procedure of Example 7, the tetrahydropyranyl groups are next removed by hydrolysis in dilute acetic acid at about 40° C. and the formula-IV title compound recovered, as mixed isomers.

IV. The formula-IV title ester is obtained by treating the above acid in ethanol-diethyl ether solution with diazoethane at about 25° C. for 15 min. and thereafter separating the product, as mixed isomers.

EXAMPLE 10

9-Deoxy-3,4-trans-didehydro-6ξ,9α-epoxy-17-phenyl-2,18,19,20-tetranor-PGF$_1$, Methyl Ester, Mixed Isomers (Formula XI: Q is

R$_1$ is methyl, R$_5$ and R$_6$ are hydrogen, s is 0, W is

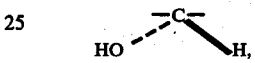

and Z is methylene).

1. Refer to Chart C. A mixture of the formula-XXXVIII 2α,4α-dihydroxy-5β-(3'α-hydroxy-5'-phenyl-1'-trans-heptenyl)-α-cyclopentylacetaldehyde-γ-lactol, 3',4-bistetrahydropyran-2-yl-ether (2.28 g.) and methyl 4-(triphenylphosphoranylidene) crotonate (Buchta et al., Chem. Ber. 92, 3111 (1959), 3.46 g.) in 100 ml. of benzene is heated at reflux for 16 hr. The mixture is concentrated to a dark orange semi-solid. The residue is subjected to silica gel chromatography, eluting with acetone (5%)-dichloromethane to yield the bistetrahydropyran-2-yl ether of the title compound, a yellow oil, 1.55 g.

The above material is hydrolyzed in acetic acid-water-tetrahydrofuran (20:10:10) at about 42° C. for 4.5 hr. Thereupon 50 ml. of water is added, the mixture is frozen, and then freeze-dried. The resulting residual oil is subjected to silica gel chromatography, eluting with acetone (30%)-dichlormethane, to yield the formula-XI title compound, mixed less polar and more polar isomers, an oil, 0.444 g., having mass spectral peaks at 386, 368, 350, 324, 287, 277, 269, 233, 133, 105, and 91; infrared absorption peaks at 3390, 1720, 1655, 1600, 1445, 1455, 1440, 1325, 1275, 1215, 1195, 1175, 1060, 975, 750 cm$^{-1}$; and NMR peaks at 1.2–3.2, 3.7, 3.8–4.6, 5.4–5.65, 5.7–6.1, 6.7–7.1, and 7.2 δ.

The product is principally the less polar isomer, named (3E,6R)-2,18,19,20-tetranor-Δ$^3$-17-phenyl-PGI$_1$, methyl ester. The more polar isomer is named (3E,6S)-2,18,19,20-tetranor-Δ$^3$-17-phenyl-PGI$_1$, methyl ester.

EXAMPLE 11

9-Deoxy-6ξ,9α-epoxy-3-oxa-PGF$_1$, Methyl Ester, Mixed Isomers (Formula VII: C$_g$H$_{2g}$ is trimethylene, Q is

$R_1$ is methyl, $R_5$ and $R_6$ are hydrogen, W is

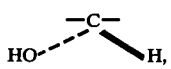

and ~ is alpha and beta).

1. Refer to Chart E. There is first prepared the bis-tetrahydropyran-2-yl ether of the title compound. A solution of the formula-XLI 3,3a$\beta$,4,5,6,6a$\beta$-hexahydro-5$\alpha$-hydroxy-2$\xi$-(2'-hydroxyethyl-4$\beta$-(3'$\alpha$-hydroxy-trans-1-octenyl)-2H-cyclopenta[b]furan, 3',5-bistetrahydropyran-2-yl ether (Example 5, 0.80 g.) in 10 ml. of dimethyl sulfoxide and 5 ml. of tetrahydrofuran is treated at about 0°–5° C. with 1.1 ml. of 1.6 M n-butyllithium in hexane added dropwise over a one-minute period. Thereafter the mixture is stirred at about 10° C. for 5 min., followed by additions of 8 ml. of dimethylformamide and 0.35 g. of lithium chloroacetate. The mixture is stirred at about 25° C. for 22 hr., then diluted with 125 ml. of ice and water containing 3 ml. of concentrated hydrochloric acid. The resulting mixture is extracted with dichloromethane and the organic phase is washed with cold water and brine, and concentrated. The residue containing the acid form of the formula-LIII bistetrahydropyran-2-yl ether, is converted to the methyl ester in diethyl ether by reaction with diazomethane. After 3 min., the excess diazomethane is destroyed with acetic acid and the mixture is washed with dilute potassium hydroxide solution and brine, dried, and concentrated to yield the formula-LIII bistetrahydropyran-2-yl ether of the title compound, as mixed isomers.

II. The above ether is hydrolyzed in 15 ml. of acetic acid and 7.5 ml. of water at 37°–39° C. for 2.5 hr. The mixture is diluted with ice and water and extracted with diethyl ether-dichloromethane (3:1). The organic phase is washed with dilute aqueous potassium hydroxide and brine, dried, and concentrated. The residue is subjected to silica gel chromatography, eluting with 2–5% methanol in ethyl acetate, to yield the formula-VII title compound, as mixed less polar and more polar isomers, 0.400 g., having NMR peaks at 5.3–5.55, 4.01, 3.69, and 3.4–4.5; and mass spectral peaks (for the TMS derivative) at 514, 499, 455, 443, 424, and 355.

The principal product is the more polar isomer and is named (6R)-3-oxa-PGI$_1$, methyl ester. The less polar isomer is named (6S)-3-oxa-PGI$_1$, methyl ester.

EXAMPLE 12

9-Deoxy-6$\xi$,9$\alpha$-epoxy-PGF$_1$ Methyl Ester, Mixed Isomers, (Formula IV: $C_gH_{2g}$ is trimethylene, $d$ is 3, Q is

$R_1$ is methyl, $R_5$ and $R_6$ are hydrogen, W is

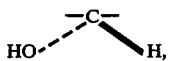

and ~ is alpha or beta); and
9-Deoxy-6$\xi$,9$\alpha$-epoxy-PGF$_1$, Mixed Isomers (Formula IV: $C_gH_{2g}$, d, Q, $R_5$, $R_6$, W, and ~ are as above, and $R_1$ is hydrogen).

1. Refer to Chart H. There are first prepared the formula LXIII halo compounds. A solution of PGF$_{2\alpha}$, 11,15-bistetrahydropyran-2-yl ether (2.1 g.) in 10 ml. of methanol is converted to the methyl ester with 20 ml. of a diethyl ether solution of diazomethane at about 25° C. for 15 min. Thereafter the mixture is concentrated to an oil. The resulting 11,15-bistetrahydropyran -2-yl-PGF$_{2\alpha}$, methyl ester (2.0 g.), suspended in 23 ml. of water, is treated with sodium bicarbonate (0.7 g.) and cooled in an ice bath. To the resulting solution is led potassium iodide (1.93 g.) and iodine (2.28 g.) and stirring continued for 16 hr. at about 0° C. Thereafter a solution of sodium sulfite (1.66 g.) and sodium carbonate (0.76 g.) in 10 ml. of water is added. After a few minutes the mixture is extracted with chloroform. The organic phase is washed with brine, dried over sodium sulfate, and concentrated to yield mainly the formula-LXIII iodo compound as the bis(tetrahydropyran-2-yl ether), mixed isomers, 2.2 g., an oil, having R$_f$ 0.75 (TLC on silica gel in A-IX system).

II. The above formula-LXIII 9-deoxy-6$\xi$,9$\alpha$-epoxy-5-iodo-PGF$_1$, methyl ester, bistetrahydropyranyl ether (2.2 g.) is dissolved in 15 ml. of benzene and treated with 15 ml. of an ether solution of tributyltin hydride (freshly prepared from tributyltin chloride and lithium aluminum hydride and containing about 0.145 g. per ml.) added dropwise over 20 min. after about 30 min. an additional 20 ml. of tributyltin hydride in ether is added and stirred continued for 1 hr. The reaction mixture is concentrated.

The residue above, largely the bistetrahydropyranyl ether of the formula-LXIV methyl ester, is converted to the title compound as follows. The oily residue is treated with 40 ml. of acetic acid-water-tetrahydrofuran (20:10:3) for about 16 hr. at 25° C. Then 250 ml. of toluene is added and the mixture is concentrated, repeating this procedure again. The residue is again treated in 40 ml. of acetic acid-water-tetrahydrofuran (20:10:3) at 40°–45° C. for 2 hr., taken up in 250 ml. of toluene, and concentrated. The residue is dissolved in 25 ml. of dichloromethane and subjected to silica gel chromatography, eluting with ethyl acetate (50–80%)-Skellysolve B. One fraction, 0.77 g., is again subjected to silica gel chromatography, eluting with acetone (20–40%)-dichloromethane, to yield the formula-IV 9-deoxy-6$\xi$,9$\alpha$-epoxy-PGF$_1$ methyl ester, mixed isomers, 0.19 g., having R$_f$ 0.26 (TLC on silica gel in ethyl acetate); [$\alpha$]$_D$+27° (chloroform); NMR peaks at 0.9, 1.15–2.8, 3.3–4.4, 3.8, 4.63, and 5.65–5.85 $\delta$; and mass spectral peaks (TMS derivative) at 512, 497, 481, 441, 391, 351, 325, and 323; and high-resolution mass spectral peak at 512.3333.

III. The formula-IV methtyl ester above is converted to the formula-IV acid as follows. A solution of the methyl ester (1.0 g.) in 30 ml. of methanol is treated with 20 ml. of 3N. potassium hydroxide at about 25° C. for 1.5 hr. Thereafter the mixture is acidified to pH 1 with 45 ml. of 2N. potassium hydrogen sulfate and diluted with 50 ml. of water. The mixture is saturated with sodium chloride and extracted with ethyl acetate. The organic phase is washed with brine, dried over sodium sulfate, and concentrated to yield an oil containing the formula-IV free acid, which gradually crystallizes. The product is subjected to silica gel chromatography, eluting with acetone (30–50%)-dichloromethane, to yield the title compound, 9-deoxy-6ξ,9α-epoxy-PGF$_{1\alpha}$, mixed less polar and more polar isomers, 0.84 g. melting 79.2°–84.5° C., having infrared absorptions at 3340, 3220, 2620, 1715, 1695, 1360, 1320, 1235, 1210, 1080, 990, 975, and 950 cm$^{-1}$; $[\alpha]_D$+28° (Chloroform); and mass spectral peaks (TMS derivative) at 555, 499, 480, 465, 409, and 173; with high resolution mass spectral peak at 570.3569.

Following the procedures of Example 12, but replacing the PGF$_{2\alpha}$, 11,15-bistetrahydropyran-2-yl ether starting material with the following formula-LXII compounds or their C-11 and C-15 ethers, there are obtained the corresponding formula-LXIII iodo compounds:

15-Methyl-PGF$_{2\alpha}$
15-Ethyl-PGF$_{2\alpha}$
16,16-Dimethyl-PGF$_{2\alpha}$
16,16-Difluoro-PGF$_{2\alpha}$
16-Phenoxy-17,18,19,20-tetranor-PGF$_{2\alpha}$
17-Phenyl-18,19,20-trinor-PGF$_{2\alpha}$
11-Deoxy-PGF$_{2\alpha}$
2a,2b-Dihomo-PGF$_{2\alpha}$
3-Oxa-PGF$_{2\alpha}$
3-Oxa-17-phenyl-18,19,20-trinor-PGF$_{2\alpha}$.
PGF$_{2\alpha}$, 15-methyl ether
PGF$_{2\alpha}$, amide
PGF$_{2\alpha}$, methylamide
PGF$_{2\alpha}$, anilide
2-Decarboxy-2-hydroxymethyl-PGF$_{2\alpha}$
2-Decarboxy-2-hydroxymethyl-16,16-dimethyl-PGF$_{2\alpha}$
2-Decarboxy-2-hydroxymethyl-16,16-difluoro-PGF$_{2\alpha}$
2-Decarboxy-2-hydroxymethyl-16-phenoxy-17,18,19,20-tetranor-PGF$_{2\alpha}$
2-Decarboxy-2-hydroxymethyl-17-phenyl-18,19,20-trinor-PGF$_{2\alpha}$ Thereafter, following the reductive dehalogenation procedures of Example 12 and subsequent work-up of the product, there are obtained the corresponding formula-LXIV products, as mixtures of less polar and more polar isomers, which are separated into the corresponding (6S) and (6R) isomers:

9-Deoxy-6ξ,9α-epoxy-15-methyl-PGF$_1$
9-Deoxy-6ξ,9α-epoxy-15-ethyl-PGF$_1$
9-Deoxy-6ξ,9α-epoxy-16,16-dimethyl-PGF$_1$ 9-Deoxy-6ξ,9α-epoxy-16,16-difluoro-PGF$_1$
9-Deoxy-6ξ,9α-epoxy-16-phenoxy-17,18,19,20-tetranor-PGF$_1$
9-Deoxy-6ξ,9α-epoxy-17-phenyl-18,19,20-trinor-PGF$_1$
9-Deoxy-6ξ,9α-epoxy-11-deoxy-PGF$_1$
9-Deoxy-6ξ,9α-eopxy-2a,2b-dihomo-PGF$_1$
9-Deoxy-6ξ,9α-epoxy-3-oxa-PGF$_1$
9-Deoxy-6ξ,9α-epoxy-3-oxa-17-phenyl-18,19,20-trinor-PGF$_1$.
9-Deoxy-6ξ,9α-epoxy-PGF$_1$, 15-methyl ether
9-Deoxy-6ξ,9α-epoxy-PGF$_1$, amide
9-Deoxy-6ξ,9α-epoxy-PGF$_1$, methylamide
9-Deoxy-6ξ,9α-epoxy-PGF$_1$, anilide
9-Deoxy-6ξ,9α-epoxy-2-decarboxy-2-hydroxymethyl-PGF$_1$
9-Deoxy-6ξ,9α-epoxy-2-decarboxy-2-hydroxymethyl-16,16-dimethyl-PGF$_1$
9-Deoxy-6ξ,9α-epoxy-2-decarboxy-2-hydroxymethyl-16,16-difluoro-PGF$_1$
9-Deoxy-6ξ,9α-epoxy-2-decarboxy-2-hydroxymethyl-16,-phenoxy-17,18,19,20-tetranor-PGF$_1$
9-Deoxy-6ξ,9α-epoxy-2-decarboxy-2-hydroxymethyl-17-phenyl-18,19,20-trinor-PGF$_1$.

Among the starting materials are 2-decarboxy-2-hydroxymethyl-PGF$_{2\alpha}$ analogs, for which see also U.S. Pat. No. 4,032,576 and references cited therein.

EXAMPLE 13

9-Deoxy-6ξ,9α-epoxy-PGF$_1$, Methyl Ester, Mixed Isomers (Formula IV: as in Example 12).

I. Refer to Chart H, and consider R$_4$ on R$_{22}$ and Q$_2$ to be hydrogen. There is first prepared the formula-LXIII halo compound. A solution of PGF$_{2\alpha}$, methyl ester (9.0 g.) in 125 ml. of dichloromethane, cooled in an ice bath, is treated with anhydrous sodium carbonate (5.3 g.) and iodine (6.35 g.) and stirred for 1 hr. Then it is allowed to warm up to 25° C. while stirring for 16 hr. The reaction mixture is diluted with 250 ml. of dichloromethane and then 100 ml. of 10% aqueous sodium sulfite is added. When the iodine color disappears the organic phase is separated, and the aqueous phase is extracted with dichloromethane. The organic phases are combined, washed with brine, dried over sodium sulfate, and concentrated. The resulting oil, 13.5 g., is subjected to silica gel chromatography, eluting with acetone (20–50%)-dichloromethane, to yield the formula-LXIII 9-deoxy-6ξ,9α-epoxy-5-iodo-PGF$_1$, methyl ester, mixed isomers, 4.76 g., having $R_f$ 0.40 (TLC on silica gel in acetone-dichloromethane (3:7)); $[\alpha]_D$+22° (chloroform); mass spectral peaks (TMS derivative) at 623, 567, 548, 517, 511, 477, 451, 521, 199, and 173; high resolution mass peak at 638.2314; and infrared absorption peaks at 3380, 2960, 2940, 2860, 1740, 1440, 1365, 1230, 1195, 1175, 1075, 1055, and 1020 cm$^{-1}$.

II. Next, the formula-IV title compound is prepared. A solution of the above formula-LXIII 5-iodo compound (0.98 g.) in 10 ml. of benzene is treated at about 15° C. with 5 mg. of 2,2-azobis-(2-methylpropionitrile) and a solution of 0.58 g. of tributyltin hydride in 4 ml. of diethyl ether added dropwise over about 2 min. The mixture is allowed to warm to about 25° C. while stirring for 1.25 hr. Another portion of tributyltin hydride (0.58 g.) is added and stirring continued for 0.75 hr. The reaction mixture is concentrated, then diluted with 25 ml. of Skellysolve B and 25 ml. of water, stirred for 0.5 hr. and filtered through diatomaceous earth. The aqueous phase together with aqueous washed of the organic phase, is mixed with 50 ml. of ethyl acetate, saturated with sodium chloride, and stirred for 0.5 hr. The organic phase, together with ethyl acetate washes of the aqueous phase and including the solution in skellysolve B, is dried over sodium sulfate and concentrated. The resulting oil is subjected to silica gel chromatography, eluting with acetone (25–50%)-dichloromethane, to yield the formula-IV title compound, mixed isomers, 0.48 g., having the same properties as the product of Example 12.

EXAMPLE 14

9-Deoxy-6ξ,9α-epoxy-17-phenyl-18,19,20-trinor-PGF$_1$, Methyl Ester, Mixed Isomers (Formula X: $d$ is 3, Q is

R$_1$ is methyl, R$_5$ and R$_6$ are hydrogen, $s$ is 0, W is

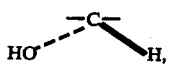

Z is methylene, and ~ is alpha or beta).

I. Refer to Chart H. There is first prepared the formula-LXIII 5-iodo compound. A solution of 17-phenyl-18,19,20-trinor-PGF$_{2\alpha}$, methyl ester (2.3 g.) in 25 ml. of dichloromethane, cooled in an ice bath, is treated with anhydrous sodium carbonate (1.06 g.) and iodine (1.27 g.) and stirred for one hr. Thereafter the mixture is allowed to warm to 25° C., with stirring for 16 hr. The reaction mixture is diluted with 50 ml. of dichloromethane and treated with 20 ml. of 10% aqueous sodium sulfite. After the iodine color has disappeared, the organic phase, together with organic extractions of the aqueous phase with dichloromethane, is dried and concentrated to a pale yellow oil, 2.64 g. The oil is subjected to silica gel chromatography to yield the formula-LXIII 9-deoxy-6ξ,9α-epoxy-5-iodo-17-phenyl-18,19,20-trinor-PGF$_1$, methyl ester, mixed isomers, 1.57 g., having R$_f$ 0.24 (TLC on silica gel in acetone-dichloromethane (3:7)); NMR peaks at 1.5–2.1, 2.1–2.8, 3.5, 3.66, 3.7–4.2, 4.3–4.6, 5.4–5.7, and 7.2 δ; mass spectral peaks (TMS derivative) at 657, 582, 567, 545, 477, 455, 389, 377, and 259; and infrared absorption at 3390, 1735, 1600, 1495, 1455, 1435, 1360, 1305, and 975.

II. Next, the formula-X title compound is prepared. A solution of the above formula-LXIII 5-iodo compound (1.0 g.) in 9 ml. of benzene is treated with 3 mg. of 2,2-azobis-(2-methyl propionitrile) and to the cold mixture is added 10 ml. of an ether solution of tributyltin hydride (freshly prepared and containing about 0.145 g. per ml.) dropwise over about 5 min. The mixture is allowed to warm to 22°-25° C. and stirred for about 45 min. until the reaction is shown complete by TLC. The mixture is concentrated and the residue stirred with 25 ml. of Skellysolve B and 25 ml. of water for 0.5 hr. The aqueous phase, together with aqueous washes of the Skellysolve B layer, is saturated with sodium chloride and extracted with ethyl acetate. The organic phase, together with ethyl acetate extractions of the aqueous phase, is dried and concentrated to an oil, 0.87 g. The oil is subjected to silica gel chromatography, eluting with acetone (20–50%)-dichloromethane to yield the formula-X title compound, mixed less polar and more polar isomers, 0.568 g., having R$_f$ 0.17 (TLC on silica gel in acetone-dichloromethane (3:7); NMR peaks at 1.2–2.9, 3.69, 3.7–4.6, 5.4–5.65, and 7.2 δ; mass spectral peaks at 546, 531, 515, 456, 441, 432, 425, and others; and infrared absorption at 3400, 1735, 1495, 1450, 1435, 750, and others cm$^{-1}$.

The principal product is the more polar isomer and is named (6S)-17-phenyl-18,19,20-trinor-PGI$_1$, methyl ester. The less polar isomer is named (6R)-17-phenyl-18,19,20-trinor-PGI$_1$, methyl ester.

EXAMPLE 15

5-ξ-Iodo-9-deoxy-6ξ,9α-epoxy-PGF$_1$, Mixed Isomers, (Formula LXIII: R$_{16}$ is —COOH).

A solution of the formula-LXIII 5ξ-iodo-9-deoxy-6ξ,9α-epoxy-PGF$_1$, methyl ester, mixed isomers (Example 13, 1.00 g.) in 25 ml. of methanol is treated at about 0° C. with 20 ml. of 3 N aqueous sodium hydroxide. After 15 min. the cooling bath is removed and stirring continued for 2 hr. Crushed ice is added, together with aqueous potassium hydrogen sulfate to acidify. The mixture is extracted with ethyl acetate and the organic phase is washed with brine, dried over magnesium sulfate, and concentrated. The residue is subjected to silica gel chromatography using acidwashed silica gel, eluting with acetone (40–100%)-methylene chloride. There is obtained the title compound, consisting of mixed isomers, having $[\alpha]_D = +20°$ (C = 0.992 in chloroform); infrared absorption at 3360, 2920, 2860, 2640, 1730, 1710, 1455, 1410, 1380, 1235, 1185, 1075, 1050, and 970 cm$^{-1}$; and mass spectral peaks at 696.2554, 681, 625, 606, 569, 535, 479, and 173.

EXAMPLE 16

(5S,6S)-5-Iodo-9-deoxy-6,9α-epoxy-PGF$_1$, Methyl Ester, Less Polar Isomer, and
(5R,6R)-5-Iodo-9-deoxy-6,9α-epoxy-PGF$_1$, Methyl Ester, More Polar Isomer (Formula LXIII).

A suspension of PGF$_{2\alpha}$, methyl ester (3.0 g.) in 60 ml. of water is treated with sodium carbonate )1.7 g.) and cooled in an ice bath. To the resulting solution is added potassium iodide (2.7 g.) and iodine (4.14 g.) and stirring continued for 3 hr. at about 0° C. Thereafter sodium sulfite (2.5 g.) and sodium carbonate (0.8 g.) are added to decolorize the mixture. After a few minutes the mixture is extracted with chloroform. The organic phase is washed with brine, dried over sodium sulfate, and concentrated to yield the mixed isomers of the title compounds, an oil, which is further purified by silica gel chromatography, eluting with methylene chloride (15–50%)-acetone to yield to less polar (5S,6S) title compound, 0.29 g., having R$_f$ 0.44 (TLC on silica gel in ethyl acetate); and the more-polar (5R,6R) title compound, 3.36 g., having R$_f$ 0.41 (TLC on silica gel in ethyl acetate).

EXAMPLE 17

9-Deoxy-6,9α-epoxy-PGF$_1$, Methyl Ester, less-polar isomer and more-polar isomer. (Formula-IV).

Refer to Chart H. A solution of the less-polar isomer of the formula-LXIII iodo ether (Example 16, 0.247 g.) in 3 ml. of absolute ethanol is treated with tributyl tin chloride (0.12 g.) and then with a freshly prepared solution of sodium borohydride (0.050 g.) in 3 ml. of absolute ethanol. After 45 min. the reaction mixture is diluted with ethyl acetate and water. The organic phase is separated, washed, dried, and concentrated to an oil, 0.14 g., having properties identical to those of the title compound, less-polar isomer, of Example 38, hereinafter.

Likewise following the above procedure but starting with the more-polar formula-LXIII iodo ether, there is obtained an oil, 0.14 g., having properties identical to those of the title compound, more-polar isomer, of Example 38.

EXAMPLE 18

9-Deoxy-6,9α-epoxy-PGF$_1$, Amide, less polar and more polar isomers (Formula XXVIII).

I. Refer to Chart I. There are first prepared the formula-LXVI 5-iodo-9-deoxy-6,9α-epoxy-PGF$_1$, amide, less polar and more polar isomers. A solution of the formula-LXV iodo-ether acid, mixed isomers (Example 15, 5.0 g.) in 50 ml. of acetone is cooled to about −10° C. and treated with 3.0 ml. of triethylamine and 3.0 ml. of isobutyl chloroformate. After 5 min. there is added 100 ml. of acetonitrile saturated with ammonia, and the reaction mixture allowed to warm to about 25° C. The mixture is filtered, and the filtrate concentrated. The residue is taken up in ethyl acetate and water. The organic phase is washed with water, dried over magnesium suflate and concentrated. The residue is subjected to silica gel chromatography, eluting with acetone (25–100%)-methylene chloride. There are obtained the formula-LXVI iodo-ether, amide, less polar isomer, 0.02 g., having R$_f$ 0.40 (TLC on silica gel in acetone); a fraction of mixed less and more polar isomers, 2.2 g.; and the more polar isomer, 1.5 g., having R$_f$ 0.37 (TLC on silica gel in acetone), infrared absorption at 3250, 3150, 1660, 1610, 1085, 1065, 1050, and 965 cm$^{-1}$, and NMR peaks at 6.4, 5.5, 3.5–4.7 and 0.9 δ.

II. A mixture of the formula-LXVI 5-iodo-9-deoxy-6,9α-epoxy-PGF$_1$, amide, mixed isomers (Example 18-1 above, 0.48 g.) in 15 ml. of ethanol is treated at about 25° C. with about 0.5 ml. of tributyltin chloride and a mixture of sodium borohydride (0.10 g.) in 5 ml. of ethanol. The reaction is followed by TLC (silica gel in acetone). After about 30 min. additional 0.75 ml. of tributyltin chloride is added, and, after further stirring for 45 min., 0.15 g. of sodium borohydride is added. After an additional hour the reaction is complete as shown by R$_f$ = 0.49. The reaction mixture is diluted with ice and water and extracted with ethyl acetate. The organic phase is washed with brine, dried, and concentrated. The residue is subjected to silica gel chromatography, eluting with acetone (50–100%)-methylene chloride. There is obtained a fraction consisting of a mixture of the less and more polar isomers, 0.17 g., and another fraction consisting of the more polar isomer, 0.18 g. The less polar isomer has R$_f$ 0.46 (TLC on silica gel run twice in acetone). This less polar isomer is named (6R)-PGI$_1$, amide. The more polar isomer has R$_f$ 0.43 (TLC on silica gel run twice in acetone), and infrared absorption at 3275, 3060, 1680, 1640, 1610, 1300, 1275, 1225, 1160, 1130, 1080, 1045, 970, 910, and 775 cm$^{-1}$. This more polar isomer is named (6S)-PGI$_1$, amide.

EXAMPLE 19

9-Deoxy-6ξ,9α-epoxy-PGF$_1$, Methylamide, mixed isomers (Formula LXVII: one R$_{18}$ is hydrogen and the other R$_{18}$ is methyl).

I. Refer to Chart I. There are first prepared the formula LXVI 5ξ-iodo-9-deoxy-6ξ,9α-epoxy-PGF$_1$, methylamide, mixed isomers. A solution of the formula-LXV 5ξ-iodo-9-deoxy- 6ξ,9α-epoxy-PGF$_1$, mixed isomers (Example 15, 4.66 g.) in 50 ml. of acetone is treated with 1.42 ml. of triethylamine and cooled to −5° C. Thereupon 1.3 ml. of isobutyl chloroformate is added, with stirring at 0° C. for 5 min., followed by 25 ml. of 3M methylamine in acetonitrile. The solution is stirred for 20 min. more as it warmed to about 25° C. The mixture is filtered and concentrated. The oily residue is triturated with methylene chloride, and filtered to remove a precipitate. The filtrate is subjected to silica gel chromatography, eluting with acetone (50–90%)-methylene chloride, to yield the 5ξ-iodo-9-deoxy-6ξ,9α-epoxy-PGF$_1$, methylamide mixed isomers, 3.45 g., having NMR peaks at 6.3, 5.4-5.7, 3.2-4.7, 2.78, and 0.7- 2.65 δ.

II. A solution of the above formula-5ξ-iodo-9-deoxy-6ξ,9α-epoxy-PGF$_1$, methylamide mixed isomers (0.67 g.) in 15 ml. of methanol is treated at about 25° C. with 1.5 ml. of tributyltin chloride and thereafter with sodium borohydride (0.35 g.) added portionwise within 15 min. After 1 hr. an additional 0.75 ml. of tributyltin chloride is added and stirring continued 16 hr. Then another 0.15 g. of sodium borohydride is added and stirring continued for 15 min. The reaction mixture is diluted with 75 ml. of brine and extracted with ethyl acetate. The organic phase is separated, washed with brine, dried over sodium sulfate, and concentrated. The residue is chromatographed on silica gel, eluting with acetone (25–75%)-methylene chloride, to yield the title compound as mixed C-6 isomers, 0.46 g., having mass spectral peaks at 511.3520, and NMR peaks at 6.7, 5.3-5.7, 3.3-4.6, 2.76, and 0.7-2.6 δ. The product is principally the more polar isomer, named (6S)-PGI$_1$, methylamide. The less polar isomer is named (6R)-PGI$_1$, methylamide.

EXAMPLE 20

9-Deoxy-6ξ,9α-epoxy-PGF$_1$, Benzylamide, mixed isomers (Formula LXVII: one R$_{18}$ is hydrogen and the other R$_{18}$ is benzyl).

I. Refer to Chart I. Following the procedures of Example 19 there are first prepared the formula-LXVI 5ξ-iodo-9-deoxy-6ξ,9α-epoxy-PGF$_1$, benzylamide, mixed isomers. There is used 4.66 g. of the formula-LXV 5ξ-iodo-9-deoxy-6ξ,9α-epoxy-PGF$_1$, mixed isomers, and 1.08 g. of benzylamine instead of methylamine. The crude product is chromatographed on silica gel, eluting with acetone (50–70%)-methylene chloride, to yield the 5ξ-iodo-9-deoxy-6ξ,9α-epoxy-PGF$_1$, benzylamide mixed isomers, 4.1g, having NMR peaks at 7.3, 6.6, 5.3-5.7, and 3.5/4.6 ξ.

II. Following the procedures of Example 19-II, the above formula-LXVI compound is treated with tributyltin chloride and sodium borohydride until the reaction is complete as shown by TLC. Silica gel chromatography yields the title compound as mixed C-6 isomers, 0.22 g., having mass spectral peaks at 659.4204, 644, 588, 569, 221, and 173. The product is principally the more polar isomer, named (6S)-PGI$_1$, benzylamide. The less polar isomer is named (6R)-PGI$_1$, benzylamide.

EXAMPLE 21

9-Deoxy-6ξ,9α-epoxy-PGF$_1$, Anilide, mixed isomers (Formula LXVII: one R$_{18}$ is hydrogen and the other R$_{18}$ is phenyl).

I. Refer to Chart I. Following the procedures of Example 19 there are first prepared the formula-LXVI 5ξ-iodo9-deoxy-6ξ, 9α-epoxy-PGF$_1$, anilide, mixed isomers. There is used 4.66 g. of the formula-LXV 5ξ-iodo-9-deoxy-6ξ,9α-epoxy-PGF$_1$, mixed isomers, and 0.94 g. of aniline. The crude product is chromatographed on silica gel, eluting with acetone (10 -50%)-methylene chloride, to yield the 5ξ-iodo-9-deoxy-6ξ,9α-epoxy-PGF$_1$, anilide mixed isomers, 4.0 g., having NMR peaks at 8.4, 6.9-7.7 5.3-5.7, and 3.4-4.7 δ.

II. Following the procedures of Example 19-II, the above formula-LXVI compound is treated with tributyltin chloride and sodium borohydride until the reaction is complete as shown by TLC. Silica gel chromatography yields the title compound as mixed C-6 isomers, 0.29 g., having mass spectral peaks at 645.4033, 630, 574, 555, 540, and 514. The product is principally the more polar isomer named (6S)-PGI$_1$, anilide. The less polar isomer is named (6R)-PGI$_1$, anilide.

EXAMPLE 22

5ξ-Bromo-9-deoxy-6ξ,9α-epoxy-PGF$_1$, Methyl Ester, mixed isomers (Formula LXIII) and 9-Deoxy-6ξ,9α-epoxy-PGF$_1$, Methyl Ester, mixed isomers (Formula IV).

I. Refer to Chart H. A solution of PGF$_{2\alpha}$, methyl ester (1.00 g.) in 25 ml. of methylene chloride is treated at about 0° C. with N-bromosuccinimide (0.50 g.) added in portions within 3min. After additional stirring for 10 min. the reaction is complete as shown by TLC (on silica gel in ehtyl acetate). The solution is washed with aqueous sodium sulfite and water, dried over magnesium sulfate, and concentrated. The colorless oily residue is chromatographed on silica gel, eluting with acetone (20–40%) -methylene chloride to yield the mixed isomers of the formula-LXIII 5-bromo title compound, 1.18 g., a colorless oil, having mass spectral peaks at 575.2203, 559, 519, 511, 510, 500, 469, 429, 403, 199, and 173; and having an NMR spectrum essentially identical to that of the corresponding 5ξ-iodo compound prepared by the method of Example 10, viz.: 5.5, 4.55, 3.4-4.2, 3.65, and 0.9 δ.

II. Thereafter, following the procedures of Example 13-II but replacing the formula-LXIII 5-iodo compound of that example with the formula-LXIII 5-bromo compound above, there is obtained the formula-IV title compound.

EXAMPLE 23

9-Deoxy-6ξ,9α-epoxy-13,14-dihydro-15-deoxy-PGF$_1$, Methyl Ester (Formula XXXIV: Q$_2$ is

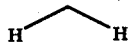

and X' is —CH$_2$CH$_2$—) and 9Deoxy-6ξ,9α-epoxy-13,14-dihydro-PGF$_1$, Methyl Ester (Formula XXXIV: Q$_2$ is

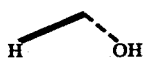

and X' is —CH$_2$CH$_2$—).

A solution of 9-deoxy-6ξ,9α-epoxy-PGF$_1$, methyl ester (Example 13, estimated 10 mg.) in 3 ml. of methanol is hydrogenated at atmospheric pressure in the presence of platinum oxide until the starting material is no longer evident by TLC. There are obtained the title compounds: the formula-XXXIV 15-deoxy compound having R$_f$ 0.60 (TLC on silica gel in acetone-methylene chloride (3:7) and mass spectral peaks at 426, 336, 311, and 221; and the formula XXXIV 9-deoxy-6ξ,9α-epoxy-13,14-dihydro-PGF$_1$, methyl ester having R$_f$ 0.24 (TLC on silica gel in acetone-methylene chloride (3:7) and mass spectral peaks at 443, 425, 424, 414, 409, 399, 393, 353, 334, 309, 267, 219, 199, 177, and 173. The 15-deoxy compound is principally the more polar isomer and is named (6S)-15-deoxy-13,14-dihydro-PGI$_1$, methyl ester. The less polar isomer is the (6R) compound. The second title compound above is named (6S)-13,14 -dihydro-PGI$_1$, methyl ester and its less polar isomer is (6R)-13, 14-dihydro-PGI$_1$, methyl ester.

EXAMPLE 24

9-Deoxy-6,9α-epoxy-15(S)-15-methyl-PGF$_1$, Amide, more polar isomer (Formula XXXI: R$_{31}$

wherein R$_{18}$ is hydrogen).

A solution of the formula-IV 9-deoxy-6,9α-epoxy-15(S)-15-methyl-PGF$_1$, more polar isomer (Example 40, 0.50 g.) in 10 ml. of acetone is cooled to about −10° C. and treated with 0.3 ml. of triethylamine and 0.3 ml. of isobutyl chloroformate. After 5 min. there is added 10 ml. of acetonitrile saturated with ammonia, and the reaction mixture allowed to warm to about 25° C. within 10 min. The mixture is filtered, and the filtrate concentrated. The residue is taken up in ethyl acetate, washed with water, dried over magnesium sulfate, and concentrated. The residue is subjected to silica gel chromatography, eluting with acetone (40–100%)-methylene chloride, to yield the title compound, a colorless oil, 0.43 g., having R$_f$ 0.14 (TLC on silica gel in methanol-acetic acidchloroform (5:5:90)), having 4.2, and 0.9 δ, and infrared absorption at 3360, 3220, 1670, 1620, 1460, 1410, 1380, 1225, 1125, 1075, 1060, and 975cm$^{-1}$. This more polar isomer is named (6R,15S)-15-methyl-PGI$_1$, amide, Following the procedure of Example 24, but starting with the less polar isomer of 9-deoxy-6,9α-epoxy-15(S)-15-methyl-PGF$_1$ (Example 40), there is obtained the less polar isomer of 9-deoxy-6,9α-epoxy-15(S)-15-methyl-PGF$_1$, amide. This less polar isomer is named (6S,15S)-15-methyl-PGI$_1$, amide.

EXAMPLE 25

5-(Chloromercurio)-9-deoxy-6ξ, 9α-epoxy-16,16-dimethyl-PGF$_1$, Mixed Isomers (Formula LXIX: G is chloro, L is —(CH$_2$)$_3$—, Q$_2$ is

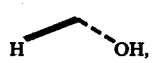

R$_1$ is hydrogen, R$_2$ is

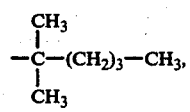

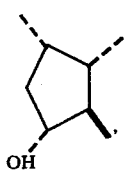 is

and ~ is alpha or beta): and 9-Deoxy-6ξ,9α-epoxy-16,16-dimethyl- PGF₁, Mixed Isomers (Formula IV: $C_gH_{2g}$ is trimethylene, d is 3, Q is

$R_1$, $R_5$ and $R_6$ are hydrogen; W is $$-\overset{-C-}{\underset{H\quad H}{\diagup\diagdown}};$$

and ~ is alpha or beta).

I. Refer to Chart J. A solution of 16,16-dimethyl-PGF$_{2\alpha}$, 11,15-bistetrahydropyran-2-yl ether (U.S. Pat. No. 3,903,131, Example 17, 1.02 g.) in 20 ml. of chloroform is treated with a solution of mercuric acetate (1.15 g.) in 40 ml. of acetic acid and left standing with light excluded for 5 hr. Thereupon 70 ml. of toluene is added and the mixture concentrated. The residue is taken up in 75 ml. of diethyl ether contacted with water and brine, dried, and concentrated. The residue, an oil, which is largely the bistetrahydropyranyl ether of the formula-LXIX chloromercurio title compound, is treated with 50 ml. of a mixture of acetic acid-water-tetrahydrofuran (20:10:3) at 43°–47° C. for 2.5 hr. Thereupon 40 ml. of toluene is added and the mixture concentrated to yield the formula-LXIX chloromercurio compound, an oily residue containing the mixed isomers.

II. The residue from I above is dissolved in 10 ml. of tetrahydrofuran and diluted with 10 ml. of water. To the mixture, while stirring, is added 10 ml. of aqueous 3M. sodium hydroxide and 10 ml. of aqueous 0.5 M sodium borohydride in 3M. sodium hydroxide. After additional stirring for 1 min., the mixture is cooled in an ice bath and diluted with 100 ml. of ethyl acetate and 10 ml. of water. There is then added 12 g. of potassium hydrogen sulfate and solid sodium chloride to saturation. The aqueous phase is extracted with ethyl acetate. The ethyl acetate solution is combined with the organic phase, dried over sodium sulfate, and concentrated. The residue, an oil, is subjected to silica gel chromatography, eluting with methanol (1–11%)-dichloromethane, to yield the formula-IV title compound, mixed isomers, 0.180 g., having $R_f$ 0.24 (TLC on silica gel in A-IX system); NMR peaks at 0.8-1.1, 1.15-1.85, 2.0-2.5, 3.5-3.9, 4.35-4.6, and 5.5-5.7 δ; and mass spectral peaks (TMS derivative) at 441, 423, 383, 351, 325, 323, 307, 233, and 201.

EXAMPLE 26

5-(Acetatomercurio)-9-deoxy-6ξ,9α-epoxy-PGF₁ Mixed Isomers (Formula LXIX: G is CH₃C(O)O—, L is —(CH₂)₃—, Q₂ is

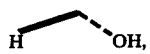

$R_{25}$ is n-pentyl,  is $R_{30}$ is —COOH, and ~ is alpha or beta); 5-(Chloromercurio)-9-deoxy-6ξ,9α-epoxy-PGF₁, Mixed Isomers (Formula LXIX: as above except G is chloro); and 5(Hydroxymercurio-9-deoxy-6ξ,9α-epoxy-PGF₁, inner salt, (formula-LXXIV wherein L, Q₂, $R_{22}$, $R_{25}$ and ~ are as above).

I. Refer to Chart J. A solution of PGF$_{2\alpha}$, 11,15-bistetrahydropyran-2-yl ether (1.3 g.) in 30 ml. of chloroform is treated with a solution of mercuric acetate (1.59 g.) in 60 ml. of acetic acid and stirred with light excluded for 5 hr. To the resulting clear solution is added 75 ml. of toluene and the mixture is concentrated to yield the bistetrahydropyranyl ether of the formula-LXIX acetatomercurio title compound. The residue is treated with 50 ml. of a mixture of acetic acid-water-tetrahydrofuran (20:10:3) at about 40° C. for 4 hr. Thereafter 40 ml. of toluene is added and the mixture is concentrated to yield the formula-LXIX acetatomercurio title compound, mixed isomers.

II. The above bistetrahydropyran-2-yl ether of the formula-LXIX acetatomercurio compound is taken up in a mixture of diethyl ether-water and contacted with 20 ml. of brine. The organic phase is dried over anhydrous sodium sulfate and concentrated to yield mainly the bistetrahydropyranyl ether of the formula-LXIX chloromercurio compound. The residue is treated with 6.6 ml. of a mixture of acetic acid-water-tetrahydrofuran (20:10:3) at about 40° C. for 4 hr. Thereupon 20 ml. of toluene is added and the mixture is concentrated to yield the formula-LXIX chloromercurio title compound: 2.0 g., an oil, soluble in ethyl acetate or dichloromethane. An analytical sample is obtained on subjecting the material to silica gel chromatography, eluting with ethyl acetate (50–100%)-hexane. The product, mixed isomers, 0.256 g., an oil, has Cl:Hg atomic ratio 1:1, and infrared absorption spectral peaks at 3360, 2660, 1720, 1705, 1305, 1225, 1185, and 1060 cm⁻¹. An alternate name for this chloromercurio compound is {4-Carboxy-1-3,3aβ,4,5,6,6aβ-hexahydro-5α-hydroxy-4β-[(1E,3S)-3-hydroxy-1-octenyl]-2H-cyclopenta[a]furan-2ξ-yl butyl}chloromercury.

III. Refer to Chart K. The above formula-LXIX chloromercurio product is converted to the formula-LXXXIV hydroxymercurio inner salt by dissolving it in 1 N. potassium hydroxide and precipitating with acetic acid. The product, a waxy solid, is insoluble in water, very slightly soluble in chloroform or dichloromethane, and soluble in hot methanol. It is readily soluble in dilute potassium hydroxide thereby forming the potassium salt of the hydroxymercurio compound.

Following the procedures of Examples 25 and 26, but replacing those starting materials with the appropriate tetrahydropyran-2-yl ether of $PGF_{2\alpha}$ or a $PGF_{2\alpha}$ analog, there are obtained the formula-LXIX mercurio products identified in the table below as Examples 27-34.

TABLE

Mercurio products of formula LXIX
(all having L equal to trimethylene and $Q_2$ equal to 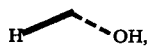 $OR_4$ wherein
$R_4$ is hydrogen ; Ex. 27-32 having
$(R_{22})$ equal to,

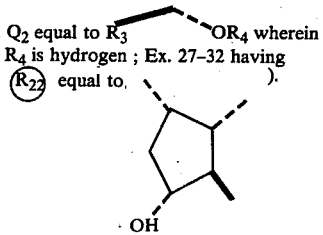

| Example | G | $R_1$ | $R_2$ | $R_3$ |
|---|---|---|---|---|
| 27 | chloro | hydrogen | phenethyl | hydrogen |
| 28 | chloro | methyl | n-pentyl | hydrogen |
| 29 | chloro | n-octyl | n-pentyl | hydrogen |
| 30 | chloro | methyl | 1,1-dimethyl-pentyl | hydrogen |
| 31 | chloro | hydrogen | phenoxy-methyl | hydrogen |
| 32 | chloro | hydrogen | n-pentyl | methyl |

(Examples 33-34 having $(R_{22})$ equal to

.)

| | | | | |
|---|---|---|---|---|
| 33 | chloro | hydrogen | n-pentyl | hydrogen |
| 34 | acetato | hydrogen | n-pentyl | methyl |

EXAMPLE 35

5-(Acetatomercurio)-9-dioxy-6ξ,9-epoxy-$PGF_1$, Methyl Ester, Mixed Isomers (Formula LXIX: G, L, $Q_2$, $(R_{22})$, $R_{25}$, and ~ are as defined in Example 26, and $R_{36}$ is —COOCH$_3$).

A solution of the formula-LXIX acetatomercurio compound of Example 26 in methanol-diethyl ether (1:1) is treated with a solution of diazomethane in diethyl ether at about 25° C. for 5 min. The reaction mixture is concentrated to yield the methyl ester title compound.

Following the procedure of Example 35 but using in place of the diazomethane, diazoethane, diazobutane, and 1-diazo-2-ethylhexane, there are obtained the corresponding ethyl, butyl, and 2-ethylhexyl esters of 5-(acetatomercurio)-9-deoxy-6ξ,9α-epoxy-$PGF_1$. In the same manner, the methyl, ethyl, butyl, and 2-ethylhexyl esters of 5-(chloromercurio)-9-deoxy-6ξ,9α-epoxy-$PGF_1$ are prepared. Likewise using each of the acids identified in Examples 39 and 40, hereafter, there are obtained the corresponding methyl, ethyl, butyl, and 2-ethylhexyl esters.

EXAMPLE 36

5-(Acetatomercurio)-9-deoxy-6ξ,9α-epoxy-$PGF_1$, Methyl Ester Mixed Isomers (Formula-LXIX: G, L, $Q_2$, $R_{22}$, $R_{25}$, $R_{36}$ and ~ are as defined in Example 35).

Refer to Chart J. A solution of $PGF_{2\alpha}$, methyl ester (1.75 g.) in 25 ml. of tetrahydrofuran is treated with a solution of mercuric acetate (3.5 g.) in 25 ml. of water and 25 ml. of tetrahydrofuran and stirred at about 25° C. for 2 hr. The reaction mixture is concentrated and extracted with ethyl acetate. The organic phase is washed with water, dried over magnesium sulfate, and concentrated to the product, mixed isomers, an oil, about 4.0 g., having NMR peaks at 5.5, 4.7, 3.8-4.6, 3.67, 2.0 and 0.9 δ.

EXAMPLE 37

5-(Chloromercurio)-9-deoxy-6ξ,9α-epoxy-$PGF_1$, Methyl Ester, Less Polar Isomer and More Polar Isomer (Formula LXIX of Chart J: G is chloro, L is —(CH$_2$)$_3$—, $Q_2$ is

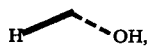

$(R_{22})$ is

$R_{25}$ is n-pentyl, $R_{36}$ is —COOCH$_3$, and ~ is alpha or beta).

The product is obtained from the acetato compound by exchange of acetato with chloro. A solution of the acetatomercurio compound of Example 36 (2.8 g.) in 50 ml. methanol is contacted with 25 ml. of brine at about 25° C. for 2 hr. The mixture is concentrated to half volume and extracted with ethyl acetate. The extract is washed with brine, dried over magnesium sulfate and concentrated to a residue, 2.2 g. The residue is subjected to silica gel chromatography, eluting with ethyl acetate (50-100%)-Skellysolve B to yield two fractions, one less polar and the other more polar. The less polar consists of the less-polar isomer of the title compound, waxy crystals, 0.33 g., recrystallized from ethyl acetate-hexane as colorless needles m. 60°-1° C. (softening at 56° C.), having $R_f$ 0.47 (TLC on silica gel in A-IX system); Cl:Hg atomic ratio 1:1; and infrared absorption bands at 3400, 1735, 1470, 1370, 1245, 1065, 970 and 890 cm$^{-1}$. The more-polar isomer is an oil, 1.00 g., having $R_f$ 0.41 (TLC on silica gel in A-IX system); Cl:Hg atomic ratio 1:1; NMR peaks at 5.5, 3.8-4.7, 3.65, 3.2, 2.75, and 0.9 δ; [α]$_D$ + 14° (C=0.9015 in CHCl$_3$); mass spectral peaks (TMS derivative) at 746, 675.1727, 656, 585, 511, 421, 199, and 173; and infrared absorption bands at 3450, 1740, 1435, 1370, 1240, 1045, 970 and 875 cm$^{-1}$.

EXAMPLE 38

9-Deoxy-6,9α-epoxy-$PGF_1$, Methyl Ester, less-polar isomer and more-polar isomer (Formula IV).

Refer to Chart J. A solution of $PGF_{2\alpha}$, methyl ester (0.73 g.) in 10 ml. of tetrahydrofuran is treated with a suspension prepared by mixing mercuric acetate (0.95 g.) in 10 ml. of water with 10 ml. of tetrahydrofuran. The mixture is stirred at about 25° C. for 2 hr. to yield the formula-LXIX 5-(acetatomercurio)-9-deoxy-6ξ,9α-epoxy-$PGF_1$, methyl ester. Thereafter a solution of sodium borohydride (0.200 g.) in 10 ml. of 1 N potassium hydroxide is added in portions within 3 min. Stirring is continued for 20 min. and diethyl ether and brine are added. The organic phase is separated, washed with brine, dried over magnesium sulfate and concentrated. The oily residue (0.66 g.) is subjected to silica gel chromatography, eluting with ethyl acetate (40-100%)-Skellysolve B. There is first obtained the formula-IV less-polar isomer, 0.070 g., then a fraction of mixed isomers, 0.112 g., and finally the formula-IV more-polar isomer, 0.250 g. The mixed-isomer fraction is again chromatographed to yield approximately one part of the less-polar isomer for every 2 parts of the more polar isomer. The combined title compound less-polar isomer is crystallized from ethyl acetate as needles, m.p. 77°-7° C., having $[\alpha]_D = +13°$ (C = 0.8245 in chloroform); NMR peaks at 5.55, 3.7-4.5, 3.7, 4.5, 3.1, 2.1-2.5, and 0.9 δ; and $R_f$ 0.40 (TLC on silica gel in acetone-methylene chloride 1:1).

This less polar isomer of the methyl ester is named (6R)-PGI$_1$, methyl ester.

The combined fractions containing the more-polar isomer yield the title compound more-polar isomer which is crystallized from diethyl ether-hexane, m.p. approximately 26° C., having $[\alpha]_D = +23°$ (C = 0.9815 in chloroform); NMR peaks essentially as for the less-polar isomer above; $R_f$ 0.37 (TLC on silica gel in acetone-methylene chloride 1:1); and mass spectral peaks at 512.3356, 497, 481, 441, 391, and 173.

This more polar isomer of the methyl ester is named (6S)-PGI$_1$, methyl ester.

EXAMPLE 39

9-Deoxy-6,9α-epoxy-PGF$_1$, less-polar isomer and more-polar isomer (Formula IV).

Refer to Chart J. A solution of PGF$_{2\alpha}$ (2.0 g.) in 40 ml. of tetrahydrofuran is treated with a mixture of mercuricacetate (3.7 g.), 30 ml. water, and 20 ml. of tetrahydrofuran for 2 hr., with stirring. Thereafter a solution of sodium borohydride (0.75 g.) in 30 ml. of 1 N sodium hydroxide is added in portions within 3 min. After 15 min. the mixture is cooled and cautiously acidified with dilute hydrochloric acid. Diethyl ether and salt (sodium chloride) are added. The organic phase is separated, washed with brine, dried, and concentrated to an oil, 2.5 g. The oil is subjected to high pressure liquid chromatography on acetic acid-washed silica gel, eluting with acetone (20-65%)-methylene chloride at approximately 50 pounds per square inch (350 g./cm$^2$). There are obtained four main fractions: (1) the less-polar isomer of the title compound, 0.26 g., (2) mixed isomers, 0.41 g., (3) the more-polar isomer, 1.01 g. and (4) recovered unreacted PGF$_{2\alpha}$, 0.2 g. The pure isomers are crystallized from ethyl acetate-hexane. The less-polar isomer has $R_f$ 0.50 (TLC on silica gel in A-IX system), m.p. 97°-9° C., and $[\alpha]_D = +13°$ (C = 1.061 in ethanol). The more-polar isomer has $R_f$ 0.45 (TLC on silica gel in A-IX system), m.p. 78°-80° C, and $[\alpha]_D = +31°$ (C = 1.031 in ethanol).

The less polar isomer of the acid is named (6R)-PGI$_1$. The more polar isomer is named (6S)-PGI$_1$.

From each of the above isomers, by esterification with diazomethane, there is obtained the corresponding methyl ester having the same properties as that of the corresponding less-polar or more-polar methyl ester of Example 38.

EXAMPLE 40

9-Deoxy-6,9α-epoxy-15(S)-15-methyl-PGF$_1$, less polar isomer and more polar isomer (Formula IV).

Refer to Chart J. A solution of 15(S)-15-methyl-PGF$_{2\alpha}$ (U.S. Pat. No. 3,728,382) (2.94 g.) in 60 ml. of tetrahydrofuran is added in portions within 3 min. to a stirred mixture of mercuric acetate (52 g.) in 45 ml. of water and 30 ml. of tetrahydrofuran. After 3 hr. stirring, a solution of sodium borohydride (1.1 g.) in 45 ml. of 1 N sodium hydroxide is added in portions. After 15 min. the mixture is cooled and treated with an aqueous solution of potassium hydrogen sulfate to pH 6. Sodium chloride and diethyl ether are added, with stirring for 5 min. The organic phase is separated. The aqueous phase is further acidified to pH 3 and again extracted. The ether extracts are combined, washed with brine, dried, and concentrated to an oil, 3.5 g. The oil is subjected to high pressure liquid chromatography on acid-washed silica gel, eluting with acetone (40-60%)-methylene chloride. There are obtained three main fractions: (1) the less-polar isomer of the title compound, 0.29 g., (2) mixed isomers, 1.10 g., and (3) the more-polar isomer, 1.71 g. Further chromatography of the mixed-isomer fraction yields more of the less- and more-polar title compound. There is obtained the less-polar isomer of the title compound, 0.43 g., having $R_f$ 0.43 (TLC on silica gel using the A-IX system 2 times); $[\alpha]_D = +9°$ (C = 1.036 in chloroform); NMR peaks at 5.77, 5.53, 4.42, 3.5-4.1, and 0.9 δ; infrared absorption at 3380, 2670, 1710, 1455, 1375, 1235, 1080 and 974 cm$^{-1}$; and mass spectral peaks at 584.3748, 569, 513, 494, 479, 423, 378, 213, 203, and 187 (TMS derivative).

This less polar isomer is named (6R, 15S)-15-methyl-PGI$_1$.

Likewise, there is obtained the more-polar isomer of the title compound, 2.35 g., having $R_f$ 0.40 (TLC as above); $[\alpha]_D = +20°$ (C = 0.8130 in chloroform); infrared absorption at 3400, 2650, 1710, 1365, 1220, 1085, 1055, and 975 cm$^{-1}$; with NMR and mass spectral data similar to those of the less-polar isomer above.

This more polar isomer is named (6S,15S)-15-methyl-PGI$_1$.

EXAMPLE 41

9-Deoxy-6ξ,9α-epoxy-2,2-difluoro-PGF$_1$, Methyl Ester, less polar isomer and more polar isomer (Formula XV).

Following the procedures of Example 38 but replacing the PGF$_{2\alpha}$, methyl ester starting material with 2,2-difluoro-PGF$_{2\alpha}$, methyl ester, there are obtained the title compounds.

EXAMPLE 42

9-Deoxy-6ξ,9α-epoxy-2,2-difluoro-16,16-dimethyl-PGF$_1$, Methyl Ester, less-polar isomer and more-polar isomer (Formula XV).

Following the procedures of Example 38 but replacing the PGF$_{2\alpha}$, methyl ester starting material with 2,2-difluoro-16,16-dimethyl-PGF$_{2\alpha}$, methylester (U.S. Pat. No. 4,001,300, Example 21) there are obtained the title compounds.

EXAMPLE 43

9-Deoxy-6ξ,9α-epoxy-2,2-difluoro-17-phenyl-18,19,20-trinor-PGF₁, Methyl Ester, less polar isomer and more polar isomer (Formula XV).

Following the procedures of Example 38 but replacing the PGF$_{2\alpha}$, methyl ester starting material with 2,2-difluoro-17-phenyl-18,19,20-trinor-PGF$_{2\alpha}$, methylester (U.S. Pat. No. 3,987,087) there are obtained the title compounds.

EXAMPLE 44

9-Deoxy-6,9α-epoxy-PGF₁, THAM Salt.

A solution of the more-polar isomer of the formula-IV 9-deoxy-6ξ,9α-epoxy-PGF₁ (Example 39, 0.088 g.) in 10 ml. of warm acetonitrile is treated while stirring, with a solution of tris(hydroxymethyl)aminomethane (THAM) (0.027 g.) in 1 ml. of dimethyl sulfoxide. The mixture is chilled until a thick gum separates. The supernatant solution is decanted to yield the title compound, a gummy solid, 0.10 g., having the same R$_f$ in the A-IX system as the starting material.

This THAM salt of the more polar isomer is named (6S)-PGI₁, THAM salt. The corresponding less polar isomer of 9-deoxy-6,9α-epoxy-PGF₁ (Example 39) yields a compound named (6R)-PGI₁, THAM salt.

EXAMPLE 45

9-Deoxy-6ξ,9α-epoxy-2,3,4-trinor-PGF₁, Bis-tetrahydropyranyl Ether, Mixed Isomers (Formula IV: Q is

and W is

A solution of the formula - XXXIX 9-deoxy-6ξ,9α-epoxy-2,3,4-trinor-PGF₁, ethyl ester, bistetrahydropyran-2-yl ether (Example 1, 3.7 g.) in 30 ml. of methanol is treated with potassium carbonate (1.0 g.) in 12 ml. of water for 16 hr. at about 25° C., with stirring. An additional 0.2 g. of potassium carbonate is added and stirring continued for 4 hr. Ice chips are added and the mixture shaken with diethyl ether-methylene chloride (3:1) and excess cold dilute hydrochloric acid. The organic phase is separated, washed with brine, dried, and concentrated to the formula-IV title compound, 3.5 g.

EXAMPLE 46

9-Deoxy-6,9α-epoxy-PGF₁, Methyl Ester, 11,15-Diacetate, More Polar Isomer.

Acetic anhydride (5 ml.) and pyridine (5 ml.) are mixed with 9-deoxy-6,9α-epoxy-PGF₁, methyl ester, more polar isomer (Example 38, 20 mg.) and the mixture is allowed to stand at 25° C. for 5–18 hr. The mixture is then cooled to 0° C., diluted with 50 ml. of water, and acidified with 5% hydrochloric acid to pH 1. That mixture is extracted with ethyl acetate and the extract is washed successively with 5% hydrochloric acid, 5% aqueous sodium bicarbonate solution, water, and brine, dried and concentrated to give the title compound.

Following the procedure of Example 46 but replacing the acetic anhydride with propionic anhydride, isobutyric anhydride, and hexanoic acid anhydride, there are obtained the corresponding dipropionate, diisobutyrate and dihexanoate derivatives of 9-deoxy-6,9α-epoxy-PGF₁, methyl ester.

EXAMPLE 47

9-Deoxy-6,9α-epoxy-2,3-dinor-PGF₁, Methyl Ester, less polar isomer (Formula IV).

I. Refer to Charts B and L. There is first prepared the formula-XLI hydroxyethyl compound. The less polar isomer of 9-deoxy-6,9α-epoxy-2,3,4-trinor-PGF₁, methyl ester, formula XXXIX (Example 3, 0.50 g.) is treated with 1.5 ml. of dihydropyran in 5 ml. of methylene chloride together with 0.5 ml. of a saturated pyridine hydrochloride solution in methylene chloride at about 25° C. for 16 hr. There is added 30 ml. of ethyl acetate and the mixture is washed with water and brine. The organic phase is dried over magnesium sulfate and concentrated to yield 9-deoxy-6,9α-epoxy-2,3,4-trinor-PGF₁, methyl ester, bis(tetrahydropyran-2-yl)ether, 0.75 g., having R$_f$ 0.67 (TLC on silica gel in ethylacetate-hexane (1:1)).

The above compound, in 8 ml. of diethyl ether, is added to a slurry of lithium aluminum hydride (0.20 g.) in 25 ml. of diethyl ether and the mixture is stirred and heated at reflux for 2 hr. It is cooled, treated with 0.3 ml. of water added cautiously, followed by 0.6 ml. of 30% aqueous sodium hydroxide, stirred until gassing stops, then filtered. The filtrate is concentrated to yield the formula-XLI compound, namely 3,3aβ,4,5,6,6aβ-hexahydro-5α-(tetrahydropyran-2-yloxy)-2α-(2-hydroxyethyl)-4β-[(3S)-3-(tetrahydropyran-2-yloxy)-trans-1-octenyl]2H-cyclopenta[b]furan, 0.70 g., having R$_f$ 0.34 (TLC on silica gel in methanol-methylene chloride (5:95)).

II. Step (a) of Chart L, to prepare compound LXXXVI. A mixture of the product of part I (0.70 g.), 5.0 ml. of pyridine, and p-toluenesulfonyl chloride (0.40 g.) is stirred at about 25° C. for 5 hr. The mixture is diluted with 50 ml. of diethyl ether, washed with cold dilute hydrochloric acid, water, cold dilute potassium carbonate solution, and brine, dried over magnesium sulfate, and concentrated. The residue is chromatographed on silica gel (Merck 40–63 μ), eluting with ethyl acetate-hexane (4:6) to yield the formula-LXXXVI tosylate, 0.84 g. having R$_f$ 0.58 and 0.62 corresponding to tetrahydropyranyl epimers (TLC on silica gel in ethyl acetate-hexane (4:6)).

III. Step (b) of Chart L, to prepare the tosylate free of THP blocking groups. A mixture of the product of part II (0.84 g.) in 18 ml. of acetic acid, 9 ml. of water, and 2 ml. of tetrahydrofuran is stirred at 40° C. for 3.5 hr. The mixture is cooled, diluted with 125 ml. of cold (−10° C.) ethyl acetate and washed with about 10% sodium hydroxide in an ice-water mixture, and brine, dried over magnesium sulfate, and concentrated. The residue is chromatographed on silica gel (Merck 40–63 μ), eluting with ethyl acetate, to yield the formula-LXXXVII compound, namely 3,3aβ,4,5,6,6aβ-hexahydro-4β-[(3S)-3-hydroxy-trans-1-octenyl]-5α-hydroxy-2α-(2-tosyloxyethyl)2H-cyclopenta[b]furan, 0.43 g., having R$_f$ 0.37 (TLC on silica gel in ethyl acetate); NMR peaks at 7.71-7.85, 7.22-7.36, 5.38-5.52, 3.63-4.23, and 2.38 δ; and mass spectral peaks at 525.2138, 596, 581, 506, 435, 409, 390, 173, 155, and 91 (TMS derivative).

IV. Step (c) of Chart L, to prepare the formula-LXXXVIII nitrile. A mixture of the product of part III (0.43 g.) and sodium cyanide (0.100 g.) in 4.3 ml. of hexamethylphosphoramide is stirred at about 25° C. for 20 hr. The mixture is then diluted with 30 ml. of ethyl acetate, washed with water and brine, dried, and concentrated. Further washing of the residue redissolved in ether, with brine, removes traces of hexamethylphosphoramide. The ether solution is dried and concentrated to yield the formula-LXXXVIII nitrile, 0.30 g., having $R_f$ 0.51 (TLC on silica gel in acetone-methylene chloride (1:1)); NMR peaks at 5.41-5.53 and 3.72-4.35 δ; and mass spectral peaks at 451.2962, 436, 380, 361, 324, 290, 264, 199, and 173 (TMS derivative).

V. Step (d) of Chart L, to prepare the formula-LXXXIX acid. A mixture of the product of part IV (0.30 g.), 3 ml. of 30% aqueous potassium hydroxide, and 3 ml. of methanol is stirred while heating up to 100° C. in 4 hr., allowing the methanol to escape, then at 100° C. for additional 3 hr. The mixture is cooled, acidified with cold dilute hydrochloric acid, and extracted with 30 ml. of ethyl acetate. The organic phase is washed with brine, dried, and concentrated to yield the formula-LXXXIX acid, namely 9-deoxy-6,9α-epoxy-2,3-dinor-PGF$_1$, 0.24 g., having $R_f$ 0.39 (TLC on silica gel in acetone-methylene chloride (1:1) containing 1% acetic acid); NMR peaks at 6.48, 5.42-5.55, and 3.63-4.35 δ; and mass spectral peaks at 542.3244, 527, 524, 471, 452, 381, 362, 355, 337, 291, 175, and 173 (TMS derivative. This formula-LXXXIX acid, the less polar isomer, is named (6R)-2,3-dinor-PGI$_1$.

VI. Step (e) of Chart L, to prepare the formula-LII (or -IV) methyl ester. The product of part V (2.5 mg.) is treated in ether solution with excess diazomethane for 5 min., thereupon removing the ether and excess diazomethane with a stream of nitrogen. The residue is chromatographed on silica gel (Merck 63-200 μ), eluting with acetone-methylene chloride (1:1), to yield the title compound, 1.5 mg., having $R_f$ 0.54 (TLC on silica gel in acetone-methylene chloride (1:1)).

This formula-LII methyl ester, the less polar isomer, is named (6R)-2,3-dinor-PGI$_1$, methyl ester.

EXAMPLE 48

9-Deoxy-6,9α-epoxy-2,3-dinor-PGF$_1$, Methyl Ester, more polar isomer (Formula IV).

I. Refer to Charts B and L. Following the procedures of Example 47 but replacing the less polar isomer of the formula-XXXIX starting material with the more polar isomer of 9-deoxy-6,9α-epoxy-2,3,4-trinor-PGF$_1$, methyl ester (Example 3, 0.25 g.) and reducing other quantities proportionally, there is obtained first the corresponding more polar bis-THP ether, 0.37 g., having $R_f$ 0.59 (TLC on silica gel in ethyl acetate-hexane (1:1)), and then the more polar formula-XLI hydroxyethyl compound, 0.34 g., having $R_f$ 0.38 (TLC on silica gel in ethyl acetate-hexane (3:1)).

II. Tosylate LXXXVI is obtained, 0.43 g., having $R_f$ 0.57 and 0.61 corresponding to tetrahydropyranyl epimers (TLC on silica gel in ethyl acetate-hexane (4:6)).

III. Tosylate LXXXVII, free of THP blocking groups, is obtained, as the more polar isomer, 0.29 g., having $R_f$ 0.33 (TLC on silica gel in ethyl acetate), NMR peaks at 7.73-7.87, 7.26-7.40, 5.44-6.57, 3.63-4.54, and 2.42 δ; and mass spectral data similar to that for the less polar isomer of Example 47-III.

IV. Nitrile LXXXVIII is obtained, as the more polar isomer, 0.21 g., having $R_f$ 0.50 (TLC on silica gel in acetone-methylene chloride 1:1)); NMR peaks at 5.44-5.57 and 3.42-4.67 δ; and mass spectral peak at 451.2953, otherwise similar to data for the less polar isomer of Example 47-IV.

V. Acid LXXXIX, as the more polar isomer, is obtained, 0.18 g., having $R_f$ 0.32 (TLC on silica gel in acetone-methylene chloride (1:1) containing 1% acetic acid; NMR peaks at 6.50, 5.45-5.58, and 3.49-4.56 δ; and mass spectral peak at 542.3292, otherwise similar to data for the less polar isomer of Example 47-V.

This formula-LXXXIX acid, the more polar isomer, is named (6S)-2,3-dinor-PGI$_1$.

VI. Methyl ester LII (or IV) is obtained, namely the title compound, more polar isomer, 1.5 mg. from 2.0 mg. of the acid, having $R_f$ 0.49 (TLC on silica gel in acetone-methylene chloride (1:1)).

This formula-LII methyl ester, the more polar isomer, is named (6S)-2,3-dinor-PGI$_1$, methyl ester.

EXAMPLE 49

9-Deoxy-6,9α-epoxy-16,16-dimethyl-PGF$_1$, less polar and more polar isomer

Formula IV: $d$ is 3, $C_gH_{2g}$ is trimethylene, Q is

$R_1$ is hydrogen, $R_5$ and $R_6$ are methyl, and W is

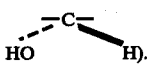

I. Refer to Chart J. The formula-LXIX 5-(acetatomercurio)-9-deoxy-6,9α-epoxy-PGF$_1$ compounds are first prepared. A solution of the formula-LXVIII 16,16-dimethyl-PGF$_2$α, 11,15-bis(tetrahydrorpyran-2-yl ether) (U.S. Pat. No. 3,954,833, 1.02 g.) in 20 ml. of chloroform is treated with a solution of mercuric acetate (1.15 g.) in 40 ml. of acetic acid. The mixture is left standing in the dark for 5 hr. Then there is added 70 ml. of toluene and the mixture concentrated. The residue is dissolved in 75 ml. of diethyl ether, washed with water and brine, dried, and concentrated. The residue is deblocked in acetic acid-water-tetrahydrofuran (20:10:3) at about 45° C. for 2.5 hr. There is added 40 ml. of toluene and the mixture is concentrated. The mixed isomers have $R_f$ 0.30 and 0.33 (TLC on silica gel in A-IX system).

II. The product of I above is dissolved in 10 ml. of tetrahydrofuran and 10 ml. of water and treated with 10 ml. of aqueous 3M sodium hydroxide and 10 ml. of aqueous 0.5M sodium borohydride in 3M sodium hydroxide. The mixture is stirred at about 25° C. for one minute, then cooled in an ice bath and treated with 100 ml. of ethyl acetate, 10 ml. of water, 12 g. of solid potassium hydrogen sulfate, and finally sodium chloride to saturation. The organic phase is separated, dried, and concentrated to an oil. The oil is chromatographed on silica gel to yield the title compounds: less polar isomer, 0.025 g. having $R_f$ 0.28 (TLC on silica gel in A-IX solvent system), and more polar isomer, 0.18 g. having $R_f$ 0.24 (TLC on silica gel in A-IX), high resolution mass spectral peak (TMS derivative 583.3656, and infrared absorption at 3440, 1740, 1560, 1435, and 1365 cm$^{-1}$. The more polar isomer is named (6S)-16,16-dimethyl-PGI.

EXAMPLE 50

9-Deoxy-6,9α-epoxy-16,16-dimethyl-PGF$_1$, less polar isomer (Formula IV).

I. Refer to Chart J and to Example 49. There are first prepared the formula-LXIX 5-(acetatomercurio)-9-deoxy-6,9α-epoxy-PGF$_1$ compounds. A solution of 2.0 g. of 16,16-dimethyl-PGF$_{2\alpha}$ in 40 ml. of tetrahydrofuran is added to a solution of 3.6 g. of mercuric acetate in 30 ml. of water and 20 ml. of tetrahydrofuran and the mixture is stirred at about 25° C. for 2 hr.

II. The product of I above is treated with a solution of 0.75 g. of sodium borohydride in 30 ml. of 1N sodium hydroxide and stirred at about 25° C. for 20 min. The mixture is acidified with 10% hydrochloric acid, diluted with 100 ml. of diethyl ether, and saturated with solid sodium chloride. The organic phase is separated, washed with brine, dried, and concentrated. The residue is chromatographed on silica gel, eluting with acetone (20–66%)-methylene chloride to yield the title compound, purified by repeated chromatography, the less polar isomer, 0.24 g., having R$_f$ 0.55 (TLC on silica gel in ethyl acetate-cyclohexane-acetic acid (20:30:1)), high resolution mass spectral peak (TMS derivative) 583.3673, and infrared absorption at 3400, 2680, 1710, 1465, 1405, 1385, 1365, 1215, 1085, 1020, 1000, and 970 cm$^{-1}$. The less polar isomer is named (6R)-16,16-dimethyl-PGI$_1$. There is also obtained the more polar isomer, 0.58 g., having R$_f$ 0.47 in the same system.

EXAMPLE 51

9-Deoxy-6,9α-epoxy-16,16-dimethyl-PGF$_1$, Methyl Ester, less polar isomer (Formula IV).

The corresponding acid (Example 50) is converted to the title compound by reaction with excess ethereal diazomethane. The product is named (6R)-16,16-dimethyl- PGI$_1$, methyl ester.

EXAMPLE 52

9-Deoxy-6,9α-epoxy-16,16-dimethyl-PGF$_1$, Methyl Ester, more polar isomer (Formula IV: R$_1$ is methyl).

I. Refer to Chart H. There are first prepared the formula-LXIII 5-iodo compounds. A mixture of 16,16-dimethyl-PGF$_{2\alpha}$, methyl ester (U.S. Pat. No. 3,954,833, 1.85 g.) in 35 ml. of methylene dichloride and 35 ml. of saturated sodium bicarbonate, cooled in an ice bath, is treated with 1.42 g. of iodine in 89 ml. of methylene dichloride, added over 15 min. The mixture is stirred for one hr. The organic phase is separated, washed with sodium sulfite and brine (backwashed with chloroform), dried, and concentrated to an oil, 2.94 g. The product is chromatographed on silica gel, eluting with ethyl acetate (50–100%)-Skellysolve B to yield the mixed C-5 isomers of the 5-iodo compound, 2.40 g. having R$_f$ 0.37 (TLC on silica gel in ethyl acetate (60%)-hexane), infrared absorption at 3420, 1735, 1260, 1230, 1195, 1170, 1090, 1075, 1050, 1020, and 1000 cm$^{-1}$, and NMR peaks at 3.65, 5.5, 4.5, and 0.9δ.

II. A solution of the product of I above (2.40 g.) in 40 ml. of absolute ethanol is treated with 2.5 ml. of tributyltin chloride and a solution of 0.5 g. of sodium borohydride in 20 ml. of absolute ethanol. The mixture is stirred at about 25° C. for 2.5 hr. There is then added, cautiously, dilute aqueous hydrochloric acid until the mixture is acidic (pH about 3) and the mixture is concentrated to about one-third volume. Water is added and the mixture is extracted with ethyl acetate. The organic phase is washed with brine, dried, and concentrated. The residue is chromatographed on silica gel, eluting with ethyl acetate (33–100%)-Skellysolve B, to yield the title compound, 1.01 g., having R$_f$ 0.65 (TLC on silica gel in ethyl acetate), mass spectral peaks (TMS derivative) at 525.3411, 509, 450, 441, 419, 351, and 201, infrared absorption at 3400, 1740, 1665, 1460, 1435, 1380, 1360, 1240, 1200, 1175, 1055, 1020, and 970 cm$^{-1}$ and NMR peaks at 5.5, 4.44, 3.65, and 0.9 δ. This more polar isomer is named (6S)-16,16-dimethyl-PGI$_1$, methyl ester.

EXAMPLE 53

9-Deoxy-6ξ,9α-epoxy-16-phenoxy-17,18,19,20-tetranor-PGF$_1$, Methyl Ester, less polar isomer and more polar isomer (Formula X: d is 3, Q is

R$_1$ is methyl, R$_5$ and R$_6$ are hydrogen, s is 0, W is

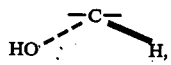

and Z is oxa (0).

The mixed isomers obtained following the paragraphs following Example 12 are separated on silica gel chromatography. The less polar isomer is named (6R)-17,18,19,20-tetranor-16-phenoxy-PGI$_1$, methyl ester. The more poplar isomer is named (6S)-17,18,19,20-tetranor-16-phenoxy-PGI$_1$, methyl ester.

EXAMPLE 54

9-Deoxy-6ξ,9α-epoxy-PGF$_1$, n-Butylamide mixed isomers (Formula LXVII: Q$_2$ is

one R$_{18}$ is hydrogen and the other is n-butyl, R$_{22}$ is

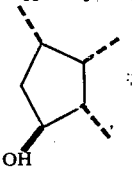

R$_{25}$ is n-pentyl).

I. Refer to Chart I. There are first prepared the formula-LXVI 5ξ-iodo-9-deoxy-6ξ,9α-epoxy-PGF$_1$, n-butyl-amide, mixed isomers. A solution of the formula-LXV 5ξ-iodo-9-deoxy-6ξ,9α-epoxy-PGF$_1$, mixed isomers (Example 15, 5.0 g.) in 50 ml. of acetone is treated with 2.0 ml. of triethylamine and cooled in a methanol-ice bath. There is then added 1.9 ml. of isobutyl chloroformate, with stirring continued for 6 min., followed by 15 ml. of n-butylamine in 20 ml. of acetone. The mixture is warmed to about 25° C. and stirred for 3 hr. The mixture is concentrated. The residue is dissolved in ethyl acetate, washed with water and brine, dried, and concentrated. The residue is chromatographed on silica gel, eluting with acetone (5-100%)-methylene chloride to yield 5.3 g., a dark oil. The product is separated from colored impurity by chromatography, to yield 4.8 g. of the 5-iodo compounds.

II. A solution of the above formula-LXVI 5ξ-iodo-9-deoxy-6ξ,9α-epoxy-PGF₁, n-butylamide mixed isomers (0.70 g.) in 25 ml. of ethanol is treated at about 25° C. with about 1.0 ml. of tributyltin chloride and 0.15 g. of sodium borohydride in 5 ml. of ethanol. The reaction is followed by TLC (silica gel in acetone-methylene chloride (1:1)). After about 1.5 hr. the reaction mixture is diluted with ice and water and extracted with ethyl acetate. The organic phase is washed with brine, dried, and concentrated. The residue is chromatographed on silica gel, eluting with acetone (25-65%)-methylene chloride, to yield the title compounds, 0.60 g. having $R_f$ 0.62 (TLC on silica gel in acetone), high resolution mass spectral peak at 553.3993, and infrared absorption peaks at 3300, 3100, 1740, 1715, 1645, 1555, 1460, 1375, 1330, 1070, 1055, and 965 cm⁻¹.

EXAMPLE 55

(6S)-13,14-Didehydro-PGI₁ (Formula XXXIV: L is trimethylene, Q₂ is

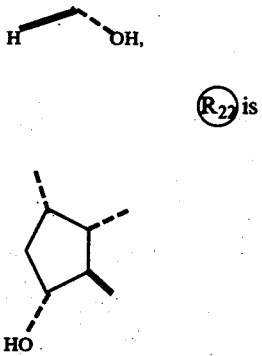

$R_{25}$ is n-pentyl, $R_{30}$ is —COOH, and X' is —C≡C—) and its Methyl Ester.

I. Refer to Chart N. There are first prepared the formula-XCV 9-deoxy-6(R and S), 9α-epoxy-14-bromo-PGF₁α, methyl esters. Starting with a solution of the formula-XCIII 14-bromo-PGF₂α, methyl ester (Preparation 2, 1.02 g.) in 10 ml. of tetrahydrofuran, that solution is treated with a suspension of mercuric acetate (1.8 g.) in water (14 ml.) and tetrahydrofuran (8.5 ml.) at about 25° C. for 15 min. The suspension is cooled in an ice-bath and treated dropwise with a solution of sodium borohydride (0.65 g.) in 1N sodium hydroxide (6.5 ml.). The mixture is diluted with diethyl ether, decanted from mercury, washed with water, dried, and concentrated to give the mixed C-6 isomers. The isomers are separated by silica gel chromatography, eluting with methylene chloride-acetone (85:15) to yield first the 6R compounds, 0.183 g. having $R_f$ 0.38 (TLC on silica gel in methylene chloride-acetone (3:1), infrared absorption at 1040, 1075, 1080, 1170, 1195, 1710, 1740, and 3300 cm⁻¹, NMR peaks at 0.90, 1.05-3.1, 3.65, 3.5-4.25, and 5.79 δ, and mass spectral peaks (TMS derivative) at 590.2450, 575, 551, 519, 511, 500, 421, 403, 384, 305, and 173.

An intermediate fraction, 0.20 g., is obtained, followed by the 6S compound, 0.452 g. having $R_f$ 0.31, infrared absorption at 1040, 1095, 1160, 1710, 1740, and 3300 cm⁻¹, NMR peaks at 0.89, 1.05-3.1, 3.65, 3.5-4.25, 4.43, and 5.585 δ, and mass spectral peaks at 590.2440 and as found for the 6R compound.

II. The formula-XCVI (6S)-13,14-didehydro-PGI₁ is obtained by treating the formula-XCV 6S isomer of I above (0.275 g.) in 10 ml. of methanol with 5 ml. of 1N aqueous sodium hydroxide at 25° C. for 20 hr. The solution is cooled and acidified with cold, dilute phosphoric acid. The mixture is extracted with diethyl ether-ethyl acetate (2:1). The organic phase is washed with 5% sodium chloride, dried, and concentrated to give the acid of the formula-XCV 14-bromo compound, 0.24 g., having $R_f$ 0.36 (TLC on silica gel in Solvent A, i.e. the organic phase from ethyl acetate-acetic acid-cyclohexane-water (9:2:5:10)), and infrared absorption 950, 1045, 1100, 1240, 1280, 1710, 2650-3100, and 3400 cm⁻¹. That acid is treated in solution (in 10 ml. of dimethylsulfoxide and 1.0 ml. of methanol) with potassium tert-butoxide (0.31 g.) at about 25° C. for 26 hr. The solution is diluted with cold water, acidified with 0.2 M potassium hydrogen sulfate and extracted with diethyl ether-ethyl acetate (2:1). The organic phase is washed with 5% sodium chloride, dried, and concentrated to yield the formula-XXXIV title compound, 0.225 g., having $R_f$ 0.43 (TLC on silica gel in solvent A), infrared absorption at 1)55, 1080, 1095, 1710, 2220, 2550-3100, and 3350 cm⁻¹, NMR peaks at 0.90, 1.05-2.9, 3.96, 4.21, and 6.38 δ, and mass spectral peaks (TMS derivative) at 568.3420, 533, 497, 478, 463, 407, 395, 388, 362, 173, and 117.

The above acid is converted to the methyl ester by reaction with excess ethereal diazomethane. The product, (6S)-13,14-didehydro-PGI₁, methyl ester, has $R_f$ 0.59 in ethyl acetate, infrared absorption at 1015, 1045, 1065, 1090, 1170, 1725, 1740, 2220, and 3400 cm⁻¹, NMR peaks at 0.90, 1.1-2.9, 3.45, 3.65, 3.65-4.2, and 4.2-4.65 δ, and mass spectral peaks at 510.3209, 495, 479, 439, 420, 395, 337, 330, 323, 313, 304, 225, and 173.

EXAMPLE 56

(6R)-13,14-Didehydro-PGI₁ (Formula XXXIV) and its Methyl Ester.

Following the procedures of Example 55 but starting with the corresponding formula-XCV 6R isomer, namely 9-deoxy-(6R), 9α-epoxy-14-bromo-PGF₁α, methyl ester (Example 55, 0.16 g.) there is obtained the corresponding acid of the 14-bromo compound, 0.14 g. having $R_f$ 0.40 in solvent A, and subsequently the title compound, 0.11 g., having $R_f$ 0.53 in solvent A, infrared absorption at 1020, 1050, 1075, 1225, 1710, 1725, 2220, 2600-2800, and 3350 cm⁻¹, and NMR peaks at 0.90, 1.1-2.9, 3.66, and 4.33 δ.

The above acid is converted to the methyl ester by reaction with excess ethereal diazomethane. The product, (6R)-13,14-didehydro-PGI₁, methyl ester, has $R_f$ 0.67 in ethyl acetate, infrared absorption at 1010, 1050, 1070, 1080, 1095, 1155, 1170, 1725, 1740, 2220, and 3400 cm⁻¹, NMR peaks at 0.90, 1.1-2.9, 3.5-4.0, 3.65, and 4.0-4.55 δ, and mass spectral peaks at 510.3193, 495, 479, and others found for the 6S compound of Example 55.

EXAMPLE 57

(6S,15R)-13,14-Didehydro-PGI₁ (Formula XXXIV: Q₂ is

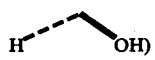

and its Methyl Ester.

Following the procedures of Example 55 but employing the corresponding 14-bromo(15R)-PGF₂α, methyl ester (Preparation 2) there are obtained the title compounds. The formula-XCV 9-deoxy-6(R and S), 9α-epoxy-14-bromo-(15R)-PGF₁α, methyl esters are first prepared and separated by chromatography. The 6R isomer is less polar and has $R_f$ 0.63 in methylene chloride-acetone (7:3) compared with 6S isomer with $R_f$ 0.55. The 6R isomer has NMR peaks at 0.89, 1.05-3.2, 3.66, 3.4-4.2, and 5.80 δ and mass spectral peaks at 590.2452, 575, 559, 519, and others. The 6S isomer has NMR peaks at 0.89, 1.1-3.5, 3.65, 3.6-4.35, 4.46, and 5.90 δ. The corresponding acids are prepared as in Example 55, using a methanolic solution containing sodium hydroxide.

The acid (6S) title compound is obtained by dehydrohalogenation with potassium tert-butoxide. The formula-XXXIV acid has $R_f$ 0.32 in methylene chloride-acetone (7:3) containing 0.2% acetic acid, infrared absorption at 1710, 2220, 2550, and 3400 cm⁻¹, NMR peaks at 0.90, 1.08-290, 3.60-4.20, 4.20-4.71, and 4.90-5.85 δ, and mass spectral peaks at 568.3414, 553, 497, 478, 463, 395, 388, 381, and 173.

The methyl ester title compound is obtained by reaction of the acid with excess ethereal diazomethane. The product has $R_f$ 0.60 in methylene chloride-acetone (7:3) containing 0.2% acetic acid, infrared absorption at 1735, 2220, 2850, 2930, and 3400 cm⁻¹, NMR peaks at 0.90, 1.08-2.75, 3.30-3.62, 3.67, 3.68-4.22, and 4.22-4.73 δ, and mass spectral peaks at 510.3193, 495, 479, 439, 420, 395, 324, 305, and 173.

EXAMPLE 58

(6R,15R)-13,14-Didehydro-PGI₁ (Formula XXXIV: Q₂ is

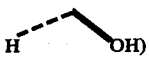

and its Methyl Ester.

Following the procedures of Example 55 but employing (6R,15R)-14-bromo-PGI₁ (Example 57) and dehalogenating that compound with potassium tert-butoxide, the acid (6R) title compound is obtained, having $R_f$ 0.40 in methylene chloride-acetone (7:3) containing 0.2% acetic acid, infrared absorption at 1710 2220, 2650, 2850, 2930, and 3400 cm⁻¹, NMR peaks at 0.90, 1.05-3.0, 3.45-3.95, 3.95-453, and 5.08 δ, and mass spectral peaks at 568.3419, 553, 497, 478, 463, 395, 388, 371, 362, and 173.

The corresponding methyl ester is obtained by reaction of the acid above with excess ethereal diazomethane and conventional recovery.

EXAMPLE 59

Trans-Δ²-PGI₁, Methyl Ester, less polar isomer and more polar isomer (Formula XXXIII: D' is

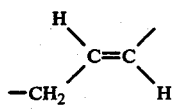

Q₂ is

R₂₂ is

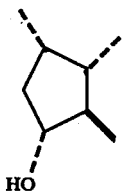

R₂₅ is n-pentyl, and R₃₀ is —COOCH₃).

I. Refer to Chart O. The formula-XCVIII phenylselenidyl ethers are prepared by starting with the formula-XCVII compounds as their 11,15-bis(t-butyldimethylsilyl)ethers. There are prepared from the mixed PGI₁ isomers (Example 17) by reaction with hexamethyldisilazane and trimethylchlorosilane.

A solution of these PGI₁, methyl esters, bis(silyl ethers) (1.425 g.) in 20 ml. of tetrahydrofuran is added to a mixture of isopropylcyclohexylamine (1.17 g.), 30 ml. of tetrahydrofuran and n-butyllithium (4.7 ml. of 1.6 M in hexane) prepared at −78° C. and stirred after the addition at −78° C. for 0.5 hr. after which a solution of diphenyl diselenide (1.76 g.) in 15 ml. of tetrahydrofuran is added. The mixture is stirred further at −78° C. for 1 hr., warmed to 0° C. and poured into 150 ml. of saturated aqueous ammonium chloride and 150 ml. of diethyl ether. The organic phase is separated, washed with ice water and brine, dried, and concentrated. The residue is separated by high pressure liquid column chromatography, using 3 Merck "B" columns in series and eluting with benzene-ethyl acetate (40:1) to yield the formula-XCVIII phenylselenidyl ethers as mixed C-6 isomers, having $R_f$ 0.52 and 0.48 (TLC on silica gel in benzene-ethyl acetate (20;1)), and NMR peaks at 7.55, 7.30, 5.45, 4.50-3.40, 3.60, 2.50-1.10, 0.90, and 0.03 δ.

II. The formula-XCIX bis(silyl ethers) of the title compounds are next obtained by oxidative elimination of phenylselenide from the above compounds. Following the procedures of Example 60, the product of I above (0.964 g.) yields 0.707 g. of trans-Δ²-PGI₁, methyl ester, 11,15-bis(t-butyldimethylsilyl ether), mixed isomers having $R_f$ 0.41 and 0.39 (TLC on silica gel in benzene-ethyl acetate (20;1)), and NMR peaks at 6.90, 5.90, 5.63, 5.42, 4.50-350, 3.64, 2.50-1.10, 0.90, and 0.02 δ.

III. The formula-XXXIII title compounds are obtained on deblocking the above compounds and separating the C-6 isomers by chromatography. The product of II above (0.707 g.) in 6 ml. of tetrahydrofuran is treated with tetra-n-butylammonium fluoride (3.5 ml. of 1.2 M solution in tetrahydrofuran) at about 25° C. for 19 hr. the mixture is diluted with 250 ml. of ethyl acetate, washed with brine, dried, and concentrated to an oil. The oil is separated by high pressure liquid column chromatography using 3 Merck "B" columns in series, eluting with methylene chloride-acetone (1:2). There are obtained the less polar isomer, 0.125 g., having m.p. 69°–71.5° C., and NMR peaks at 7.00, 5.97-5.70, 5.50, 4.35-2.90, 3.68, 2.50-1.10, and 0.90 δ, and the more polar isomer, 0.09 g., having NMR peaks at 7.00, 5.97-570, 5.50, 4.43, 4.17-2.90, 3.68, 2.60-1.10, and 0.90 δ.

EXAMPLE 60

Trans-Δ²-16,16-dimethyl-PGI$_1$, Methyl Ester, less polar isomer and more polar isomer (Formula XXXIII: D' is

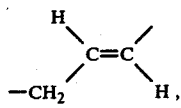

Q$_2$ is

R$_{25}$ is

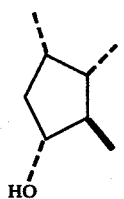

R$_{25}$ is —C(CH$_3$)$_2$—(CH$_2$)$_3$—CH$_3$, and R$_{30}$ is —COOCH$_3$.

I. Refer to Chart J. There is first prepared the formula-LXVIII 16,16-dimethyl-PGF$_2$α, methyl ester, 11,15-bis(tetrahydropyran-2-yl ether). A solution of 16,16-dimethyl-PGF$_2$α, 11,15-bis(tetrahydropyran-2-yl ether) (7.63 g.) in 180 ml. of acetonitrile is mixed with diisopropylethylamine (4.47 g.) and treated with methyl iodide (29.54 g.) at about 25° C. in the dark for 25 hr. The reaction mixture is then poured into 500 ml. of brine and extracted with diethyl ether. The organic phase is washed with ice water, dilute sodium thiosulfate, and brine, dried, and concentrated to yield the formula-LXVIII methyl ester, 7.61 g. having infrared absorption at 3400, 2900, 1730, 1430, 1350, 1190, 1120, 1070, 1010, 975, 900, 865, 810, and 725 cm$^{-1}$ and NMR peaks at 5.80-5.02, 4.85-447, 4.26-3.17, 3.63, 2.78-1.05, and 0.88 δ.

II. The formula-LXIX acetatomercurio compounds are prepared from a solution of the product of I above (7.0 g.) in 30 ml. of tetrahydrofuran added dropwise to an ice-cooled yellow suspension of mercuric acetate (5.92 g.) in 24 ml. of water and 24 ml. of tetrahydrofuran, followed by stirring at about 25° C. for 2 hr. The mixture is then poured into an ice-cold solution of sodium borohydride (2.83 g.) in 74.4 ml. of 1 N hydroxide and stirred for 10 min. The mixture is diluted with 750 ml. of brine and extracted with diethyl ether. The organic phase is dried, filtered, and concentrated to an oil. The oil is chromatographed on silica gel eluting with ethyl acetate-Skellysolve B (1:3) to yield the formula-LXX 16,16-dimethyl-PGI$_1$, methyl ester, 11,15-bis(tetrahydropyran-2-yl ether) mixed isomers, 5.65 g., a colorless oil having R$_f$ 0.44 (TLC on silica gel in ethyl acetate-toluene (1:3)), infrared absorption at 2950, 1730, 1430, 1370, 1340, 1310, 1250, 1190, 1125, 1070, 1020, 975, 910, 905, 865, 815, 730, and 705 cm$^{-1}$ and NMR peaks at 5.71-5.32, 4.85-4.53, 4.53-3.04, 3.64, 2.72-1.05, and 0.87 δ.

III. Refer to Chart O. The formula-XCVIII phenylselenidyl ether is prepared by adding a solution of the formula-XCVII compound of II above (5.03 g.) in 50 ml. of tetrahydrofuran to a mixture of diisopropylamine (1.08 g.) in 125 ml. of tetrahydrofuran and n-butyllithium (6.54 ml. of 1.5 M solution of hexane) prepared at −78° C. and stirred after the addition at −78° C. for 1.2 hr. after which a solution of phenylselenyl chloride (1.79 g.) in 30 ml. of tetrahydrofuran is added dropwise over a 7 min. period. The resulting mixture is stirred further at −78° C. for 1.25 hr., then poured into a mixture of 300 ml. of saturated aqueous ammonium chloride and 400 ml. of ice-water and extracted with diethyl ether. The organic phase is dried and concentrated. The residue is chromatographed on silica gel, eluting with ethyl acetate-toluene (1:8) to yield the formula-XCVIII compounds, mixed C-6 isomers, as an oil, 3.01 g., having R$_f$0.53 (TLC on silica gel in ethyl acetate-toluene (1:3)), infrared absorption at 2950, 1730, 1570, 1530, 1360, 1310, 1230, 1200, 1130, 1070, 1020, 975, 910, 905, 870, 815, 740, and 690 cm$^{-1}$, and NMR peaks at 7.78-7.48, 7.45-7.[6, 5.74-5.27, 4.84-4.53, 4.53-3.17, 3.62, 2.66-1.06, and 0.85 δ.

IV. The formula-XCIX bis(tetrahydropyran-2-yl ethers) of the title compounds are next obtained by oxidative elimination of phenylselenide from the formula-XCVIII compounds. The product of III above (3.01 g.) in 65 ml. of methylene chloride is treated with hydrogen peroxide (0.99 g. as 10% aqueous solution) at about 25° C. for 1 hr. The layers are separated and the organic phase is washed with 5% sodium bicarbonate, saturated aqueous sodium bicarbonate, and brine, dried, and concentrated to an oil, 2.40 g. The oil is chromatographed on silica gel, eluting with ethyl acetate-Skellysolve B (1:3), to yield the formula-XCIX compounds, mixed C-6 isomers, 1.86 g., having infrared absorption at 2950, 1730, 1660, 1440, 1380, 1310, 1260, 1200, 1120, 1070, 1020, 975, 905, 870, and 830 cm$^{-1}$, and NMR peaks at 7.38-6.73, 6.06-5.29, 4.85-3.14, 3.72, 2.75-1.06, and 0.88 δ.

V. The formula-XXXIII title compounds are obtained on deblocking the above compounds and separating the C-6 isomers by chromatograpy. The product of IV above (1.86 g.) is hydrolyzed in acetic acid-water-tetrahydrofuran (20:10:3) at about 40° C. The reaction mixture is then poured into brine and extracted with ethyl acetate. The organic phase is washed with ice water, dried, and concentrated to the mixed isomers of formula-C and oil, 1.54 g. The oil is separated by high presure liquid column chromatography using the Merck "B" columns in series and eluting with acetone-methylene chloride of gradually increasing polarity (from 1:9 to 1:5). There are obtained the less polar isomer, 0.352 g., and the more polar isomer, 0.536 g. The less polar compound showed infrared absorption at 3450, 2950, 1730, 1660, 1430, 1310, 1270, 1210, 1170, 1060, 970, 850, and 720 cm$^{-1}$, NMR peaks at 7.42–6.72, 6.06–5.35, 4.38–2.84, 3.70, 2.66–1.06, 0.86, and 0.82 δ, and a high resolution mass spectral peak at 523.3263 (TMS derivative). The more polar compound showed infrared absorption at 3450, 2950, 1730, 1660, 1430, 1310, 1270, 1240, 1210, 1180, 1040, 970, 850 and 725 cm$^{-1}$, NMR peaks at 7.47–6.72, 6.11–5.35, 4.66–3.0, 3.70, 2.70–1.08, 0.88, and 0.83 δ, and a high resolution mass spectral peak at 523.3243.

EXAMPLE 61

Trans-Δ$^2$-16,16-dimethyl-PGI$_1$, less polar isomer and more polar isomer (Formula XXXIII).

The methyl esters of Example 60 are separately hydrolyzed in t-butanol with 3N potassium hydroxide sulfate and extracted with ethyl acetate. The organic phase is washed with brine, dried, and concentrated to the title compound. From the less polar methyl ester there is obtained the less polar acid, having infrared absorption at 3400, 2900, 1700, 1650, 1420, 1250, 1060, and 970 cm$^{-1}$, and NMR peaks at 7.38–6.68, 6.13, 6.01–5.33, 4.41–3.52, 2.65–1.05, 0.88, and 0.83 δ. This less polar acid is named (2E,6R)-16,16-dimethyl-Δ$^2$-PGI$_1$.

Similarly, the more polar methyl ester yields the more polar acid, having infrared absorption at 3400, 2900, 1700, 1650, 1420, 1250, 1060, and 970 cm$^{-1}$, and NMR peaks at 7.39–6.76, 6.25, 6.03–5.39, 4.72–3.35, 2.77–1.06, 0.88, and 0.83 δ. This more polar acid is named (2E,6S)-16,16-dimethyl-Δ$^2$-PGI$_1$.

EXAMPLE 62

9-Deoxy-6ξ,9α-epoxy-13,14-dihydro-PGF$_1$, more polar isomer (Formula XXXIV: L is trimethylene, Q$_2$ is

(R$_{27}$) is

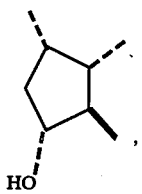

R$_{25}$ is n-pentyl, R$_{30}$ is —COOH, and X' is —CH$_2$CH$_2$—).

A solution of the formula-IV 9-deoxy-6ξ,9α-epoxy-PGF$_1$, more polar isomer (Example 38, 1.00 g.) in 100 ml. of ethyl acetate is mixed with 50 mg. of palladium (5%)-on-charcoal and hydrogenated for 7 hr. The mixture is filtered and the filtrate is concentrated to the title compound, an oil having R$_f$0.37 (TLC on silica gel in A-IX system), and NMR peaks at 6.12, 3.3–4.6, and 0.9 δ. This more polar acid is named (6S)-13,14-dihydro-PGI$_1$.

EXAMPLE 63

9-Deoxy-6ξ,9α-epoxy-2,2-difluoro-16-phenoxy-17,18,19,20-tetranor-PGF$_1$, Methyl Ester, less-polar isomer and more-polar isomer (Formula XVI).

Following the procedures of Example 38 but replacing the PGF$_{2α}$, methyl ester starting material with 2,2-difluoro-16-phenoxy-17,18,19,20-tetranor-PGF$_{2α}$, methyl ester (U.S. Pat. No. 4,001,300) there are obtained the title compounds.

EXAMPLE 64

9-Deoxy-6ξ,9α-epoxy-16-phenoxy-17,18,19,20-tetranor-PGF$_1$, Methyl Ester, less polar and more polar isomers (Formula X: d is 3, Q is

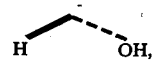

R$_1$ is methyl, R$_5$ and R$_6$ are hydrogen, s is 0, W is

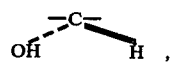

and Z is oxa (—O—)).

I. Refer to Chart H. There are first prepared the formula-LXIII 5-iodo compounds. A solution of 16-phenoxy-17,18,19,20-tetranor-PGF$_{2α}$, methyl ester (1.0 g.) in 25 ml. of methylene chloride, cooled in an ice bath, is treated with 25 ml. of saturated sodium bicarbonate and a solution of 1.0 g. of iodine in 50 ml. of methylene chloride added dropwise over 20 min. The mixture is stirred for an additional 1.5 hr., then diluted with 50 ml. of methylene chloride, washed with 5% aqueous sodium sulfite and brine, dried and concentrated. The residue, the mixed formula-LXIII 5-iodo isomers, is chromatographed on silica gel, eluting with acetone (20–30%)-methylene chloride to yield the separated isomers. The less polar isomer, 0.04 g., has R$_f$0.31 (TLC on silica gel in acetone (30%)-methylene chloride), and is identified as the 6R isomer. It has mass spectral lines (TMS derivative) at 567.1462, 580, 547, 546, 477, and 243. The more polar isomer, 0.74 g., has R$_f$0.28 in the same system and is identified as the 6S isomer.

II. Next, the formula-X title compounds are prepared, first the less polar (6R) compound. Continuing with the less polar formula-LXIII iodo compound of I above combined with other lots of the same material (0.37 g.) in 20 ml. of methanol, the solution is treated with about 0.8 ml. of tributyltin chloride, stirred for 5 min., and then with 0.37 grams of sodium borohydride added (cautiously) over 10 min. The mixture is stirred at about 25° C. for 1.5 hr., then diluted with 125 ml. of brine and extracted with ethyl acetate. The organic phase is washed with brine, dried, and concentrated. The residue is chromatographed, eluting with acetone (30%)-methylene chloride to yield the formula-X less polar title compound, namely (6R)-16-phenoxy-17,18,19,20-tetranor-PGI$_1$, methyl ester, 0.24 g. It has R$_f$0.20 (TLC on silica gel in acetone (30%)-methylene chloride).

The corresponding more polar (6S) formula-X compound is prepared similarly, following the procedure of II but replacing the iodo compound with the more polar formula-LXIII iodo compound of I above (0.40 g.).

There is obtained, after chromatography, the more polar title compound, 0.28 g., having $R_f$ 0.19 (TLC on silica gel in acetone (30%)-methylene chloride), mass spectral lines (TMS derivative) at 441.2498, 454, 423, and 351, and NMR peaks (in $CCl_4$) at 6.68–7.4, 5.6, 4.34, 3.7–4.05, and 3.55 δ. It is named (6S)-16-phenoxy-17,18,19,20-tetranor-$PGI_1$, methyl ester.

EXAMPLE 65

9-Deoxy-6ξ,9α-epoxy-16-phenoxy-17,18,19,20-tetranor-$PGF_1$, less polar and more polar isomers (Formula X: $R_1$ is hydrogen).

The methyl esters are hydrolyzed to the acids. The less polar formula-X compound (Example 64, 0.15 g.) in 6 ml. of methanol is treated with 3 ml. of water and 0.3 gram of sodium carbonate and the mixture is stirred at about 25° C. for about 16 hr. The mixture is filtered through Celite ® (a calcium aluminosilicate filter medium) and concentrated. The residue is acidified with 1N potassium hydrogen sulfate, diluted with 20 ml. of brine, and extracted with ethyl acetate. The organic phase is washed with brine, dried, and concentrated. The residue, an oil, 0.18 g., is chromatographed, eluting with acetone (25–35%)-methylene chloride, to yield the less polar formula-X title compound, 0.11 g., having NMR peaks at 6.73–7.5, 5.67–5.9, 4.38, and 3.5–4.7 δ (in acetone). The compound is named (6R)-16-phenoxy-17,18,19,20,-tetranor-$PGI_1$.

Following the above procedure but starting with the more polar formula-X methyl ester (Example 64, 0.52 g.) and using 0.8 gram of sodium carbonate, there is obtained the corresponding more polar formula-X title compound, 0.38 g., having mass spectral lines at 591.3005, 573, 512, 499, 409, and 243, and NMR peaks at 6.75–7.5, 5.3–5.83, 4.17–4.64, and 3.3–4.17 δ (in $CDCl_3$). The compound is named (6S)-16-phenoxy-17,18,19,20-tetranor-$PGI_1$.

EXAMPLE 66

9-Deoxy-6ξ,9α-epoxy-15epi-16-phenoxy-17,18,19,20-tetranor-$PGF_1$, Methyl ester, less polar and more polar isomers (Formula X: Q is

).

Following the procedures of Example 64 but replacing that starting material with 15-epi-16-phenoxy-17,18,19,20-tetranor-$PGF_{2\alpha}$, methyl ester, there are obtained the corresponding 5-iodo compounds which on reduction yield the title compounds, namely (6R,15S)-16-phenoxy-17,18,19,20-tetranor-$PGI_1$, methyl ester and (6S,15S)-16-phenoxy-17,18,19,20-tetranor-$PGI_1$, methyl ester.

EXAMPLE 67

9-Deoxy-6, 9α-epoxy-15-epi-16-phenoxy-17,18,19,20-tetranor-$PGF_1$, less polar and more polar isomers.

Following the procedures of Example 65, the methyl esters of Example 66 are hydrolyzed to the title compounds, namely (6R,15S)-16-phenoxy-17,18,19,20-tetranor-$PGI_1$ and (6S,15S)-16-phenoxy-17,18,19,20-tetranor-$PGI_1$.

I claim:
1. A cyclic ether of the formula

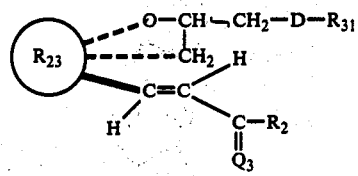

wherein D is (1) a valence bond; (2) —$(CH_2)_d$— where $d$ is 1, 2, 3, 4, or 5; (3) —CH=CH—A— where A is a valence bond or —$(CH_2)_h$— where $h$ is 1, 2, or 3; or (4) —$CH_2$—O—$CH_2$—Y— where Y is a valence bond or —$(CH_2)_k$— where $k$ is 1 or 2; wherein $R_2$ is

wherein $C_gH_{2g}$ is alkylene of 1 to 9 carbon atoms, inclusive, with 1 to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro; or

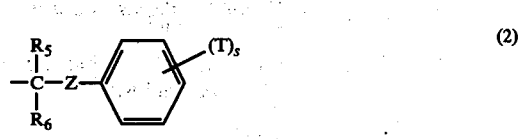

wherein $R_5$ and $R_6$ are as defined above with the proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between —$CR_5R_6$— and the phenyl ring; wherein T is alkyl of one to 4 carbon atoms, inclusive, fluoro, chloro, trifluoromethyl, or —$OR_7$ wherein $R_7$ is alkyl of 1 to 4 carbon atoms, inclusive, and $s$ is 0, 1, 2 or 3, with the proviso that not more than two T's are other than alkyl and when $s$ is 2 or 3 the T's are either the same or different;

wherein $Q_3$ is

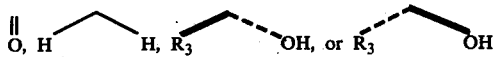

wherein $R_3$ is hydrogen or alkyl of one to 4 carbon atoms, inclusive;

wherein $R_{23}$ is

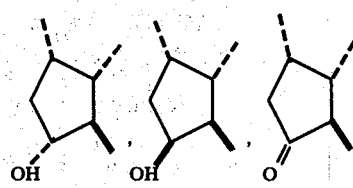

-continued

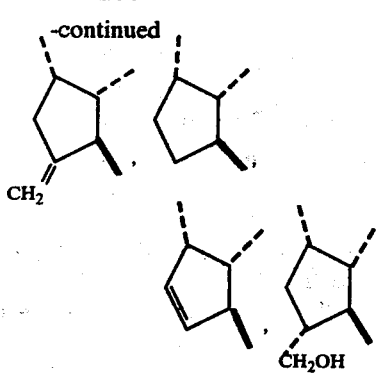

wherein R₃₁ is
(1) —COOR₃₂
(2) —CH₂N(R₁₈)₂

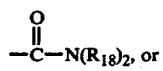 (3)

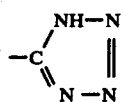 (4)

wherein R₃₂ is
wherein R₃₂ is
(a) cycloalkyl of 3 to 10 carbon atoms, inclusive,
(b) aralkyl of 7 to 12 carbon atoms, inclusive
(c) phenyl,
(d) phenyl substituted with 1, 2, or 3 chloro or alkyl of one to 4 carbon atoms, inclusive,

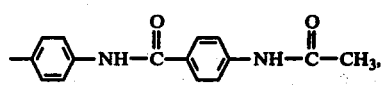 (e)

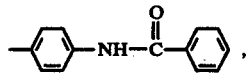 (f)

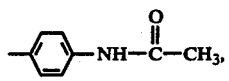 (g)

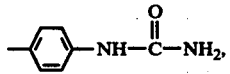 (h)

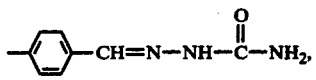 (i)

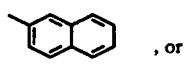, or (j)

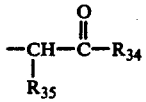 (k)

wherein R₃₄ is phenyl, p-bromophenyl, p-biphenylyl, p-nitrophenyl, p-benzamido phenyl, or 2-naphthyl, wherein R₃₅ is hydrogen or benzoyl, and wherein R₁₈ is hydrogen, alkyl of one to 12 carbon atoms, inclusive, benzyl, or phenyl, being the same or different; wherein ∼ indicates attachment in alpha or beta configuration; including the lower alkanoates thereof.

2. A compound according to claim 1 wherein Q₃ is

wherein R₃ is as defined in claim 1.

3. A compound according to claim 2 wherein R₃ is hydrogen and R₂₃ is

4. A compound according to claim 3 wherein D is a valence bond or —(CH₂)₃— wherein d is 1, 2, 3, 4, or 5.

5. A compound according to claim 4 wherein D is trimethylene.

6. A compound according to claim 5 wherein R₂ is n-pentyl.

7. A compound according to claim 6 wherein R₃₁ is

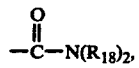

wherein R₁₈ is hydrogen, alkyl of 1 to 12 carbon atoms, inclusive, benzyl, or phenyl, being the same or different.

8. A compound according to claim 7 wherein one R₁₈ is hydrogen, methyl, or phenyl and the other R₁₈ is hydrogen.

9. 9-Deoxy-6ξ,9α-epoxy-PGF₁, amide, less polar and more polar isomers, compounds according to claim 8.

10. (6S)-PGI₁, amide, a compound according to claim 9.

11. (6R)-PGI₁, amide, a compound according to claim 9.

12. 9-Deoxy-6ξ,9α-epoxy-PGF₁, methylamide, less polar and more polar isomers, compounds according to claim 8.

13. (6S)-PGI₁, methylamide, a compound according to claim 12.

14. (6R)-PGI₁, methylamide, a compound according to claim 12.

15. 9-Deoxy-6ξ,9α-epoxy-PGF₁, anilide, less polar and more polar isomers, compounds according to claim 8.

16. (6S)-PGI₁, anilide, a compound according to claim 15.

17. (6R)-PGI₁, anilide, a compound according to claim 15.

18. 9-Deoxy-6ξ,9α-epoxy-PGF₁, n-butylamide, less polar and more polar isomers, compounds according to claim 7.

19. 9-Deoxy-6ξ,9α-epoxy-PGF₁, benzylamide, less polar and more polar isomers, compounds according to claim 7.

20. A compound according to claim 6 wherein R₃₁ is —COOR₃₂ wherein R₃₂ is

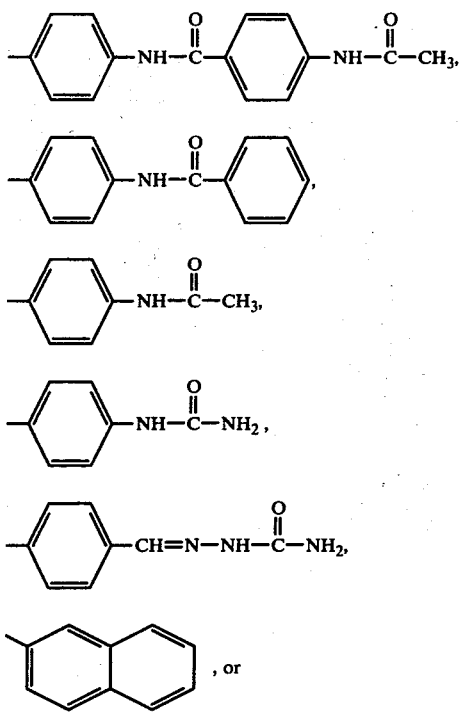

(a)

(b)

(c)

(d)

(e)

(f)

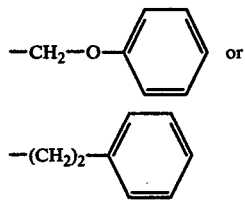, or (g) p-phenylphenacyl.

21. A compound according to claim 5 wherein $R_2$ is

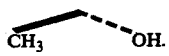 or

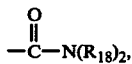

22. A compound according to claim 2 wherein $Q_3$ is

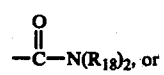

23. A compound according to claim 22 wherein $R_{31}$ is

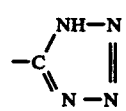

wherein $R_{18}$ is hydrogen, alkyl of 1 to 12 carbon atoms, inclusive, benzyl, or phenyl, being the same or different.

24. A compound according to claim 23 wherein one $R_{18}$ is hydrogen, methyl, or phenyl and the other $R_{18}$ is hydrogen.

25. 9-Deoxy-6ξ,9α-epoxy-15(S)-15-methyl-PGF$_1$, amide, less polar and more polar isomers, compounds according to claim 24.

26. (6S,15S)-15-Methyl-PGI$_1$, amide, a compound according to claim 25.

27. (6R,15S)-15-Methyl-PGI$_1$, amide, a compound according to claim 25.

28. A cyclic ether of the formula

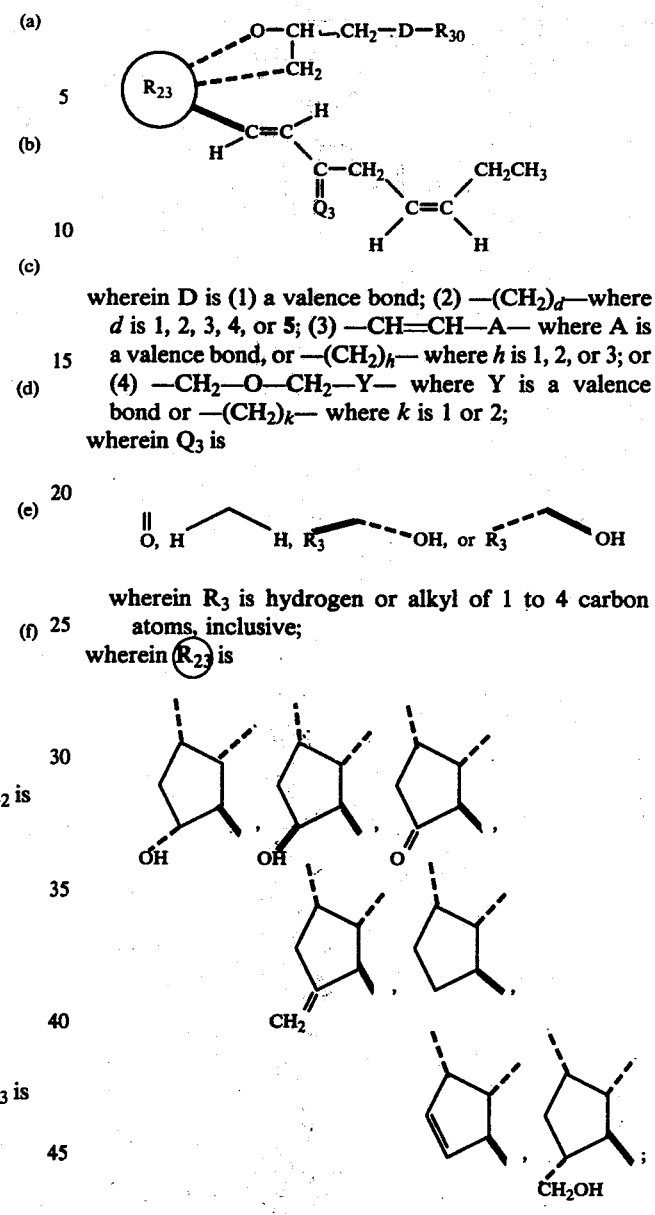

wherein D is (1) a valence bond; (2) —(CH$_2$)$_d$— where d is 1, 2, 3, 4, or 5; (3) —CH=CH—A— where A is a valence bond, or —(CH$_2$)$_h$— where h is 1, 2, or 3; or (4) —CH$_2$—O—CH$_2$—Y— where Y is a valence bond or —(CH$_2$)$_k$— where k is 1 or 2;

wherein $Q_3$ is wherein $R_3$ is hydrogen or alkyl of 1 to 4 carbon atoms, inclusive;

wherein $R_{23}$ is wherein $R_{30}$ is (1) —COOR$_{19}$ (2) —CH$_2$N(R$_{18}$)$_2$ (3)

(4)

wherein $R_{19}$ is (a) alkyl of 1 to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with 1, 2, or 3 chloro or alkyl of 1 to 4 carbon atoms, inclusive,

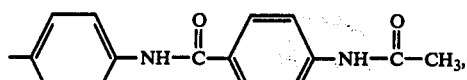 (f)

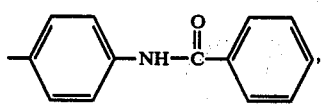 (g)

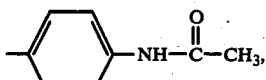 (h)

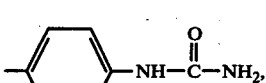 (i)

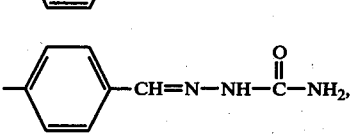 (j)

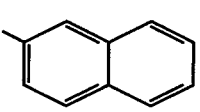 (k)

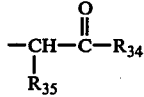

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl, (m) hydrogen; or (n) a pharmacologically acceptable cation; and wherein $R_{18}$ is hydrogen, alkyl of 1 to 12 carbon atoms, inclusive, benzyl, or phenyl, being the same or different; and wherein ~ indicates attachment in alpha or beta configuration; including the lower alkanoates thereof.

29. A compound according to claim 28 wherein $Q_3$ is

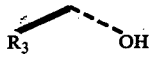

wherein $R_3$ is as defined in claim 29.

30. A compound according to claim 29 wherein $R_{23}$ is

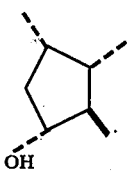

31. A compound according to claim 30 wherein D is a valence bond or $-(CH_2)_d-$ wherein d is 1, 2, 3, 4, or 5.

32. A compound according to claim 31, where, if $R_{30}$ is $-CH_2N(R_{18})_2$ or

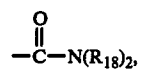

one $R_{18}$ is hydrogen, methyl, or phenyl, and the other $R_{18}$ is hydrogen, or, if $R_{30}$ is $-COOR_{19}$, $R_{19}$ is (a) hydrogen, (b) methyl, (c) ethyl,

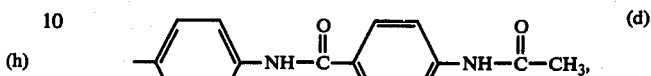 (d)

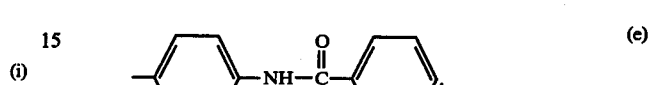 (e)

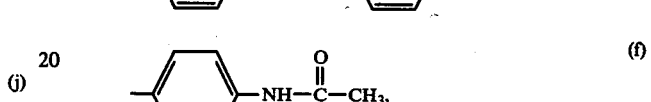 (f)

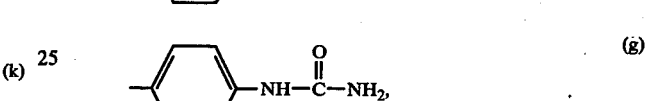 (g)

 (h)

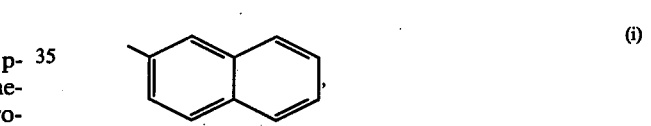 (i)

(j) p-phenylphenacyl, or (k) a pharmacologically acceptable cation.

33. A cyclic ether of the formula

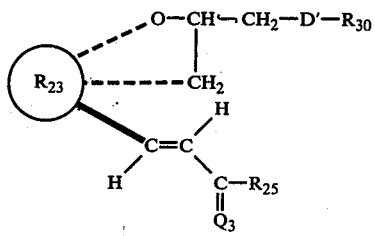

wherein D' is $-CH_2-CH=CH-A-$ or $-(CH_2)_T-CF_2-$ wherein A is a valence bond or $-(CH_2)_h-$ where h is 1, 2, or 3; and wherein t is 2, 3, or 4;

wherein $Q_3$ is

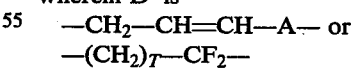

wherein $R_3$ is hydrogen or alkyl of 1 to 4 carbon atoms, inclusive, wherein $R_{23}$ is wherein R$_{25}$ is $$-\underset{R_6}{\overset{R_5}{C}}-C_gH_{2g}-CH_3 \quad (1)$$

wherein C$_g$H$_{2g}$ is alkylene of 1 to 9 carbon atoms, inclusive, with 1 to 5 carbon atoms, inclusive, in the chain between —CR$_5$R$_6$— and terminal methyl, wherein R$_5$ and R$_6$ are hydrogen, alkyl of 1 to 4 carbon atoms, inclusive, or fluoro, being the same or different, with the proviso that one of R$_5$ and R$_6$ is fluoro only when the other is hydrogen or fluoro;

(2)

wherein R$_5$ and R$_6$ are as defined above with the proviso that neither R$_5$ nor R$_6$ is fluoro when Z is oxa (—O—); wherein Z represents an oxa atom (—O—) or C$_j$H$_{2j}$, wherein C$_j$H$_{2j}$ is a valence bond or alkylene of 1 to 9 carbon atoms, inclusive, with 1 to 6 carbon atoms, inclusive between —CR$_5$R$_6$— and the phenyl ring; wherein T is alkyl of one to 4 carbon atoms, inclusive, fluoro, chloro, trifluoromethyl, or —OR$_7$— wherein R$_7$ is alkyl of one to 4 carbon atoms, inclusive, and s is 0, 1, 2, or 3, with the proviso that not more than two T's are other than alkyl and when s is 2 or 3 and T's are either the same or different; or (3)

wherein R$_{30}$ is
(1) —COOR$_{19}$
(2) —CH$_2$N(R$_{18}$)$_2$ $$-\overset{O}{\underset{\|}{C}}-N(R_{18})_2, \text{ or} \quad (3)$$

(4)

wherein R$_{19}$ is
(a) alkyl of one to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with 1, 2, or 3 chloro or alkyl of 1 to 4 carbon atoms, inclusive, (f)

(g)

(h)

(i)

(j)

(k)

$$-\underset{R_{35}}{\overset{}{CH}}-\overset{O}{\underset{\|}{C}}-R_{34} \quad (l)$$

wherein R$_{34}$ is phenyl, p-bromophenyl, p-biphenylyl, p-nitrophenyl, p-benzamidophenyl, or 2-naphthyl, and wherein R$_{35}$ is hydrogen or benzoyl,
(m) hydrogen; or
(n) a pharmacologically acceptable cation; and wherein R$_{18}$ is hydrogen, alkyl of one to 12 carbon atoms, inclusive, benzyl, or phenyl, being the same or different; and wherein $\sim$ indicates attachment in alpha or beta configuration; including the lower alkanoates thereof.

34. A compound according to claim 33 wherein Q$_3$ is wherein R$_3$ is as defined in claim 35.

35. A compound according to claim 34 wherein R$_{23}$ is

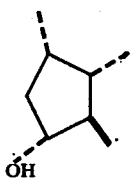

36. A compound according to claim 35 wherein D' is —(CH₂)ₜ—CF₂ where t is 2, 3, or 4.

37. A compound according to claim 36 wherein t is 2, and where, if R₃₀ is —CH₂N(R₁₈)₂ or

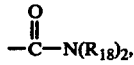

one R₁₈ is hydrogen, methyl, or phenyl, and the other R₁₈ is hydrogen, or, if R₃₀ is —COOR₁₉, R₁₉ is (a) hydrogen, (b) methyl, (c) ethyl,

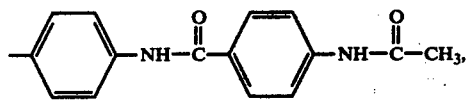 (d)

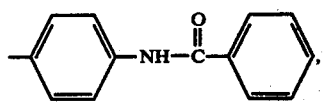 (e)

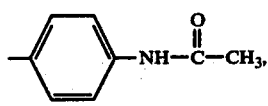 (f)

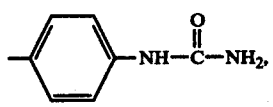 (g)

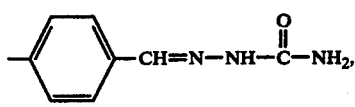 (h)

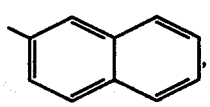 (i)

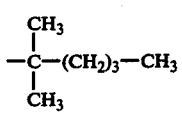

(j) p-phenylphenacyl, or
(k) a pharmacologically acceptable cation.

38. A compound according to claim 37 wherein R₂₅ is n-pentyl.

39. A compound according to claim 37 wherein R₂₅ is $$-\underset{\underset{CH_3}{|}}{\overset{\overset{CH_3}{|}}{C}}-(CH_2)_3-CH_3$$

40. A compound according to claim 37 wherein R₂₅ is

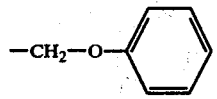

41. A compound according to claim 37 wherein R₂₅ is

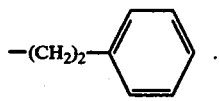

42. A compound according to claim 35 wherein D' is —CH₂—CH=CH—A— wherein A is a valence bond or —(CH₂)ₕ wherein h is 1, 2, or 3.

43. A compound according to claim 42 wherein A is a valance bond, and where, if R₃₀ is —CH₂N(R₁₈) or

one R₁₈ is hydrogen, methyl, or phenyl, and the other R₁₈ is hydrogen, or, if R₃₀ is —COOR₁₉, R₁₉ is (a) hydrogen, (b) methyl, (c) ethyl,

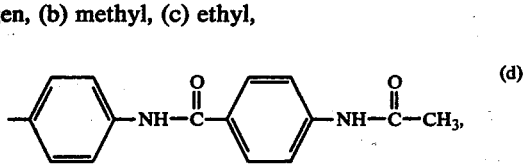 (d)

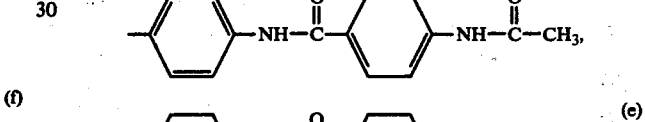 (e)

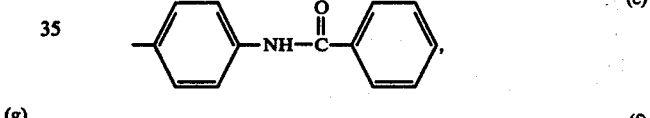 (f)

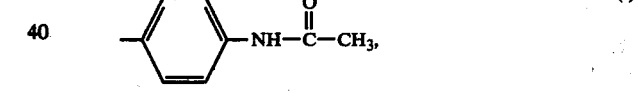 (g)

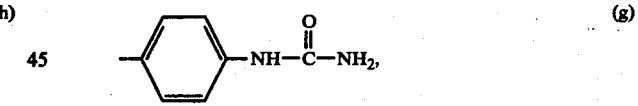 (h)

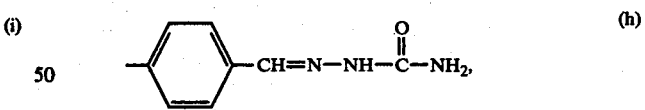 (i)

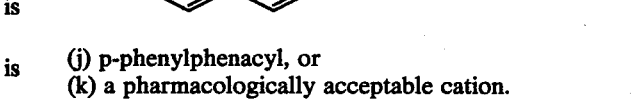

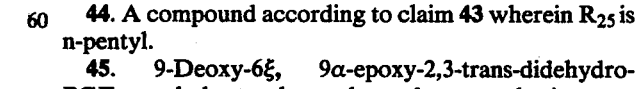

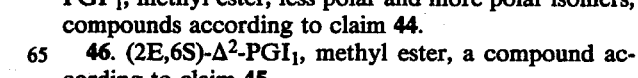

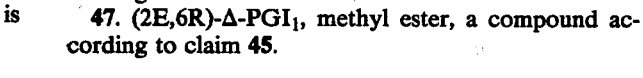

(j) p-phenylphenacyl, or
(k) a pharmacologically acceptable cation.

44. A compound according to claim 43 wherein R₂₅ is n-pentyl.

45. 9-Deoxy-6ξ, 9α-epoxy-2,3-trans-didehydro-PGF₁, methyl ester, less polar and more polar isomers, compounds according to claim 44.

46. (2E,6S)-Δ²-PGI₁, methyl ester, a compound according to claim 45.

47. (2E,6R)-Δ-PGI₁, methyl ester, a compound according to claim 45.

48. A compound according to claim 46 wherein $R_{25}$ is

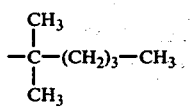

49. 9-Deoxy-6ξ,9α-epoxy-2,3-trans-didehydro-16,16-dimethyl-PGF$_1$, methyl ester, less polar and more polar isomers, compounds according to claim 48.

50. (2E, 6S)-16,16-Dimethyl-Δ$^2$-PGI, methyl ester, a compound according to claim 49.

51. (2E,6R)-16,16-Dimethyl-Δ$^2$-PGI$_1$, methyl ester, a compound according to claim 49.

52. 9-Deoxy-6ξ,9α-epoxy-2,3-trans-didehydro-16,16-dimethyl-PGF$_1$, less polar and more polar isomers, compounds according to claim 48.

53. (2E,6s)-16,16-dimethyl-Δ$^2$-PGI$_1$, a compound according to claim 52.

54. (2E,6R)-16,16-dimethyl-Δ$^2$-PGI$_1$, a compound according to claim 52.

55. A compound according to claim 43 wherein $R_{25}$ is

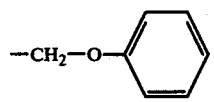

56. A comound according to claim 43 wherein $R_{25}$ is

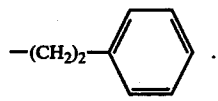

57. A cyclic ether of the formula

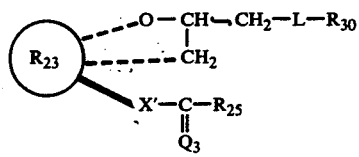

wherein L is (1) a valence bond, (2) —(CH$_2$)$_d$— wherein $d$ is 1 to 5 inclusive, (3) —(CH$_2$)$_t$—CF$_2$— wherein $t$ is 2, 3, or 4, (4) —CH$_2$—CH=CH—A— wherein A is a valence bond or —(CH$_2$)$_h$— wherein $h$ is 1, 2, or 3, or (5) —CH$_2$—O—CH$_2$—Y— wherein Y is a valence bond or —(CH$_2$)$_k$— wherein $k$ is 1 or 2; wherein Q$_3$ is

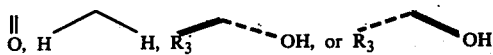

wherein R$_3$ is hydrogen or alkyl of 1 to 4 carbon atoms, inclusive;
wherein R$_{23}$ is

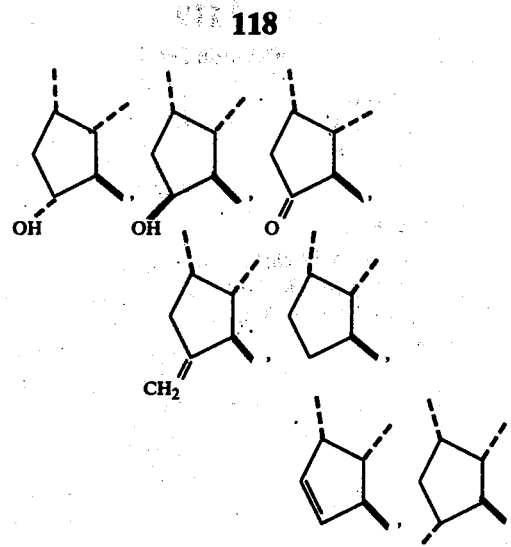

wherein $R_{25}$ is

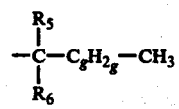

(1)

wherein $C_gH_{2g}$ is alkylene of 1 to 9 carbon atoms, inclusive, with 1 to 5 carbon atoms, inclusive, in the chain between —CR$_5$R$_6$— and terminal methyl, wherein R$_5$ and R$_6$ are hydrogen, alkyl of 1 to 4 carbon atoms, inclusive, or fluoro, being the same or different, with the proviso that one of R$_5$ and R$_6$ is fluoro only when the other is hydrogen or fluoro;

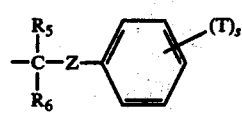

(2)

wherein R$_5$ and R$_6$ are as defined above with the proviso that neither R$_5$ nor R$_6$ is fluoro when Z is oxa (—O—); wherein Z represents an oxa atom (—O—) or C$_j$H$_{2j}$, wherein C$_j$H$_{2j}$ is a valence bond or alkylene of 1 to 9 carbon atoms, inclusive, with 1 to 6 carbon atoms, inclusive between —CR$_5$R$_6$— and the phenyl ring; wherein T is alkyl of 1 to 4 carbon atoms, inclusive, fluoro, chloro, trifluoromethyl, or —OR$_7$— wherein R$_7$ is alkyl of 1 to 4 carbon atoms, inclusive, and $s$ is 0, 1, 2, or 3, with the proviso that not more than two T's are other than alkyl and when s is 2 or 3 the T's are either the same or different; or

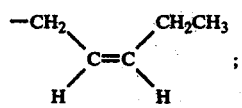

(3)

wherein R$_{30}$ is
(1) —COOR$_{19}$
(2) —(CH$_2$N(R$_{18}$)$_2$

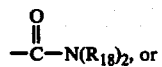

(3)

—C—N(R$_{18}$)$_2$, or

-continued

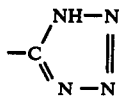 (4)

wherein R₁₉ is
(a) alkyl of 1 to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with 1, 2, or 3 chloro or alkyl of 1 to 4 carbon atoms, inclusive,

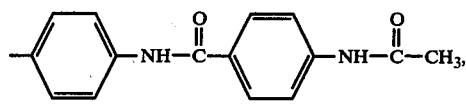 (f)

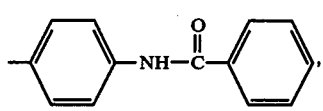 (g)

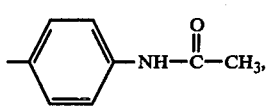 (h)

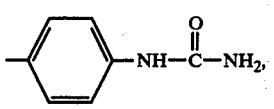 (i)

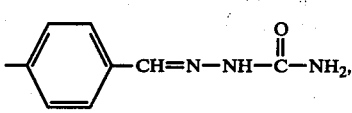 (j)

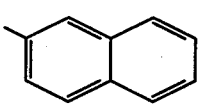 (k)

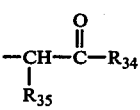 (l)

wherein $R_{34}$ is phenyl, p-bromophenyl, p-biphenylyl, p-nitrophenyl, p-benzamidophenyl, or 2-napththyl, and wherein $R_{35}$ is hydrogen or benzoyl,
(m) hydrogen, or
(n) a pharmacologically acceptable cation; and wherein $R_{18}$ hydrogen, alkyl of 1 to 12 carbon atoms, inclusive, benzyl, or phenyl, being the same or different;
wherein X' is cis—CH=CH—, —C≡C—, or —CH₂CH₂—; and wherein ~ indicates attachment in alpha or beta configuration; including the lower alkanoates thereof.

58. A compound according to claim 57 wherein X' is cis—CH=CH—.

59. A compound according to claim 57 wherein X' is —C≡C—.

60. A compound according to claim 59 wherein Q₃ is

wherein R₃ is as defined in claim 61.

61. A compound according to claim 60 wherein R₂₃ is

62. A compound according to claim 61 wherein L is trimethylene, and where, if R₃₀ is —CH₂N(R₁₈)₂ or

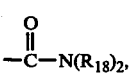

one R₁₈ is hydrogen, methyl, or phenyl, and the other R₁₈ is hydrogen, or, if R₃₀ is —COOR₁₉, R₁₉ is (a) hydrogen, (b) methyl, (c) ethyl,

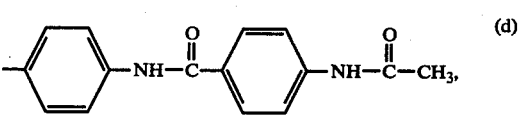 (d)

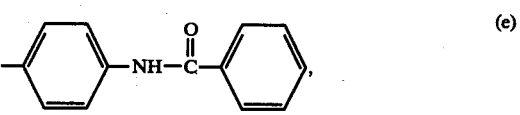 (e)

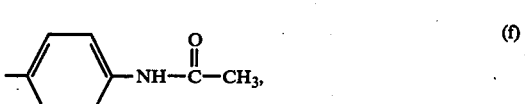 (f)

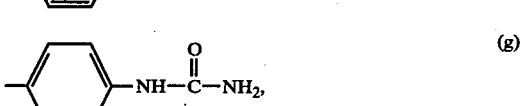 (g)

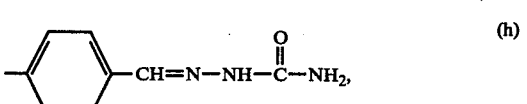 (h)

 (i)

(j) p-phenylphenacyl, or
(k) a pharmacologically acceptable cation.

63. A compound according to claim 62 wherein R₂₅ is n-pentyl.

64. 9-Deoxy-6δ,9α-epoxy-13,14-didehydro-PGF₁, methyl ester, less polar and more polar isomers, compounds according to claim 63.

65. (6S)-13,14-Didehydro-PGI₁, methyl ester, a compound according to claim 64.

66. (6R)-13,14-Didehydro-PGI₁, methyl ester, a compound according to claim 64.

67. 9-Deoxy-6δ,9α-epoxy-13,14-didehydro-PGF₁, less polar and more polar isomers, compounds according to claim 63.

68. (6S)-13,14-Didehydro-PGI₁, a compound according to claim 67.

69. (6R)-13,14-Didehydro-PGI₁, a compound according to claim 67.

70. A compound according to claim 59 wherein Q₃ is

wherein R₃ is as defined in claim 57.

71. A compound according to claim 70 wherein R₂₃ is

72. A compound according to claim 71 wherein L is trimethylene, and where, if R₃₀ is —CH₂N(R₁₈)₂ or

one R₁₈ is hydrogen, methyl, or phenyl, and the other R₁₈ is hydrogen, or if R₃₀ is —COOR₁₉, R₁₉ is (a) hydrogen, (b) methyl, (c) ethyl,

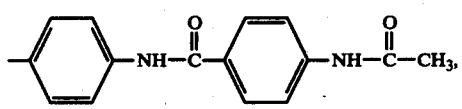 (d)

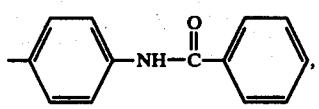 (e)

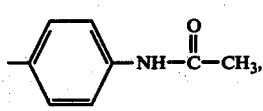 (f)

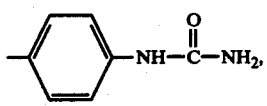 (g)

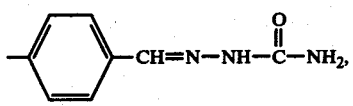 (h)

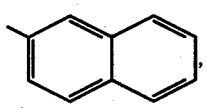 (i)

(j) p-phenylphenacyl, or (k) a pharmacologically acceptable cation.

73. A compound according to claim 72 wherein R₂₅ is n-pentyl.

74. 9-Deoxy-6δ,9α-epoxy-13,14-didehydro-(15R)-PGF₁, methyl ester, less polar and more polar isomers, compounds according to claim 73.

75. (6S,15R)-13,14-Didehydro-PGF₁, methyl ester, a compound according to claim 74.

76. (6R,15R)-13,14-Didehydro-PGF₁, methyl ester, a compound according to claim 74.

77. 9-Deoxy-6ξ,9α-epoxy-13,14-didehydro-(15R)-PGF₁, less polar and more polar isomers, compounds according to claim 73.

78. (6S,15R)-13,14-Didehydro-PGF₁, a compound according to claim 77.

79. (6R,15R)-13,14-Didehydro-PGF₁, a compound according to claim 77.

80. A compound according to claim 57 wherein X' is —CH₂CH₂—.

81. A compound according to claim 80 wherein Q₃ is

wherein R₃ is defined as in claim 57.

82. A compound according to claim 81 wherein R₂₃ is

83. A compound according to claim 82 wherein L is —(CH₂)$_d$— wherein $d$ is 1 to 5, inclusive.

84. A compound according to claim 83 wherein L is trimethylene and where, if R₃₀ is —CH₂N(R₁₈)₂ or

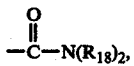

one R₁₈ is hydrogen, methyl, or phenyl, and the other R₁₈ is hydrogen, or if R₃₀ is —COOR₁₉, R₁₉ is (a) hydrogen, (b) methyl, (c) ethyl,

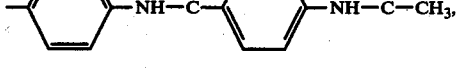 (d)

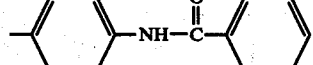 (e)

 (f)

 (g)

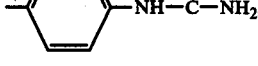 (h)

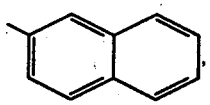

(j) p-phenylphenacyl, or
(k) a pharmacologically acceptable cation.

85. A compound according to claim 84 wherein $R_{25}$ is n-pentyl.

86. 9-Deoxy-6ξ,9α-epoxy-13,14-dihydro-PGF$_1$, methyl ester, less polar and more polar isomers, compounds according to claim 85.

87. (6S)-13,14-Dihydro-PGI$_1$, methyl ester, a compound according to claim 86.

88. (6R)-13,14-Dihydro-PGI$_1$, methyl ester, a compound according to claim 86.

89. 9-Deoxy-6ξ,9α-epoxy-13,14-dihydro-PGF$_1$, less polar and more polar isomers, compounds according to claim 85.

90. (6S)-13,14-Dihydro-PGI$_1$, a compound according to claim 89.

91. (6R)-13,14-Dihydro-PGI$_1$, a compound according to claim 89.

92. A compound according to claim 84 wherein $R_{25}$ is

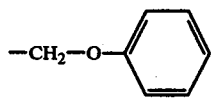

93. A compound according to claim 84 wherein $R_{25}$ is

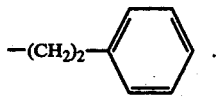

94. A compound according to claim 82 wherein L is —(CH$_2$)$_t$—CF$_2$ wherein $t$ is 2, 3, or 4.

95. A compound according to claim 94 wherein $t$ is 2, and where, if $R_{30}$ is —CH$_2$N(R$_{18}$)$_2$ or

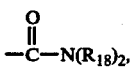

one $R_{18}$ is hydrogen, methyl, or phenyl, and the other $R_{18}$ is hydrogen, or if $R_{30}$ is —COOR$_{19}$, $R_{19}$ is (a) hydrogen, (b) methyl, (c) ethyl,

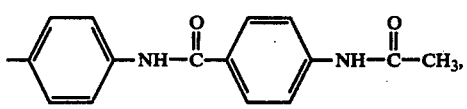 (d)

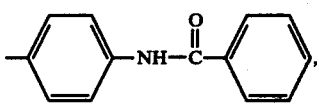 (e)

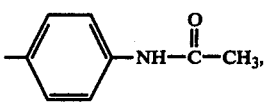 (f)

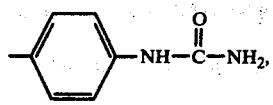 (g)

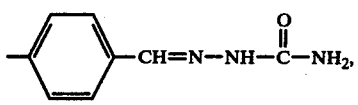 (h)

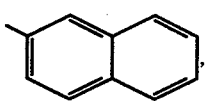 (i)

(j) p-phenylphenacyl, or
(k) a pharmacologically acceptable cation.

96. A compound according to claim 95 wherein $R_{25}$ is n-pentyl.

97. 2,2-Difluoro-9-deoxy-6ξ,9α-epoxy-13,14-dihydro-PGF$_1$, methyl ester, less polar and more polar compounds according to claim 96.

98. 2,2-Difluoro-9-deoxy-6ξ,9α-epoxy-13,14-dihydro-PGF$_1$, sodium salt, less polar and more polar compounds according to claim 96.

99. 2,2-Difluoro-9-deoxy-6ξ,9α-epoxy-13,14-dihydro-PGF$_1$, amide, less polar and more polar compounds according to claim 96.

100. A compound according to claim 95 wherein $R_{25}$ is

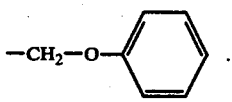

101. 2,2-Difluoro-9-deoxy-6ξ,9α-epoxy-13,14-dihydro-16-phenoxy-17,18,19,20-tetranor-PGF$_1$, methyl ester, less polar and more polar compounds according to claim 100.

102. 2,2-Difluoro-9-deoxy-6ξ,9α-deoxy-13,14-dihydro-16-phenoxy-17,18,19,20-tetranor-PGF$_1$, sodium salt, less polar and more polar compounds according to claim 100.

103. 2,2-Difluoro-9-deoxy-6ξ,9α-epoxy-13,14-dihydro-16-phenoxy-17,18,19,20-tetranor-PGF$_1$, amide, less polar and more polar compounds according to claim 100.

104. A compound according to claim 95 wherein $R_{25}$ is

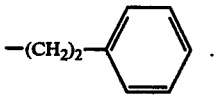

105. 2,2-Difluoro-9-deoxy-6ξ, 9α-epoxy-13,14-dihydro-17-phenyl-18,19,20-trinor-PGF$_1$, methyl ester, less polar and more polar compounds according to claim 104.

106. 2,2-Difluoro-9-deoxy-6ξ,9α-epoxy-13,14-dihydro-17-phenyl-18,19,20-trinor-PGF$_1$, sodium salt, less polar and more polar compounds according to claim 104.

107. 2,2-Difluoro-9-deoxy-6ξ,9α-epoxy-13,14-dihydro-17-phenyl-18,19,20-trinor-PGF₁, amide, less polar and more polar compounds according claim 104.

108. A compound according to claim 82 wherein L is —CH₂-CH=CH—A— wherein A is a valence bond or —(CH₂)ₕ— wherein h is 1, 2, or 3.

109. A compound according to claim 108 wherein A is a valence bond and where, if R₃₀ is —CH₂N(R₁₈)₂ or

one R₁₈ is hydrogen, methyl, or phenyl, and the other R₁₈ is hydrogen, or if R₃₀ is —COOR₁₉, R₁₉ is (a) hydrogen, (b) methyl, (c) ethyl,

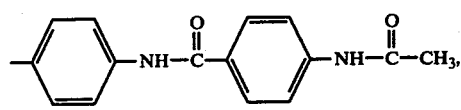 (d)

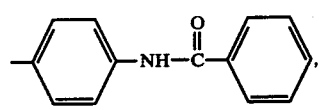 (e)

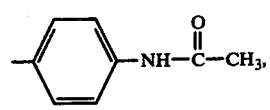 (f)

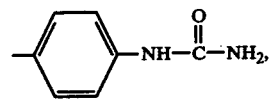 (g)

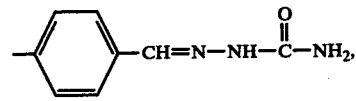 (h)

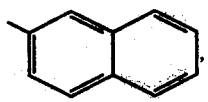 (i)

(j) p-phenylphenacyl, or
(k) a pharmacologically acceptable salt.

110. A compound according to claim 109 wherein R₂₅ is n-pentyl.

111. A compound according to claim 109 wherein R₂₅ is

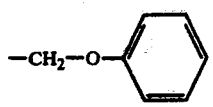

112. A compound according to claim 109 wherein R₂₅ is

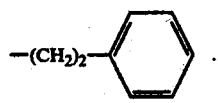

113. A compound according to claim 80 wherein Q₃ is

114. 9-Deoxy-6ξ,9α-epoxy-13,14-dihydro-15-deoxy-PGF₁, methyl ester, less polar and more polar compounds according to claim 113.

115. (6S)-13,14-Dihydro-15-deoxy-PGI₁, methyl ester, a compound according to claim 114.

116. (6R)-13,14-Dihydro-15-deoxy-PGI₁, methyl ester, a compound according to claim 114.

* * * * *

Notice of Adverse Decision in Interference

In Interference No. 100,364, involving Patent No. 4,125,712, U. F. Axen, CENTAIN 5,6-DIHYDRO-PROSTACYCLIN ANALOGS, final judgment adverse to the patentees was rendered Mar. 26, 1981, as to claims 57-93.

[*Official Gazette June 2, 1981.*]